US008546107B2

(12) United States Patent
Freeman et al.

(10) Patent No.: US 8,546,107 B2
(45) Date of Patent: Oct. 1, 2013

(54) EPIDERMAL GROWTH FACTOR RECEPTOR MUTATIONS

(75) Inventors: Daniel J Freeman, Thousand Oaks, CA (US); Todd Juan, Newbury Park, CA (US); Robert Radinsky, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/184,474

(22) Filed: Jul. 15, 2011

(65) Prior Publication Data

US 2012/0328620 A1 Dec. 27, 2012

Related U.S. Application Data

(62) Division of application No. 11/361,711, filed on Feb. 23, 2006, now Pat. No. 7,981,605.

(60) Provisional application No. 60/656,263, filed on Feb. 24, 2005.

(51) Int. Cl.
*C07K 14/71* (2006.01)
*C12P 21/04* (2006.01)

(52) U.S. Cl.
USPC .......... 435/69.7; 530/350

(58) Field of Classification Search
None
See application file for complete search history.

(56) References Cited

U.S. PATENT DOCUMENTS

| | | | | |
|---|---|---|---|---|
| 5,710,010 | A * | 1/1998 | Vogelstein et al. | 435/7.23 |
| 5,985,553 | A * | 11/1999 | King et al. | 435/6.16 |
| 7,294,468 | B2 | 11/2007 | Bell et al. | |
| 7,442,507 | B2 * | 10/2008 | Polsky et al. | 435/6.14 |
| 7,560,111 | B2 | 7/2009 | Kao et al. | |
| 2005/0272083 | A1 | 12/2005 | Seshagiri | |
| 2005/0277118 | A1 * | 12/2005 | Roth et al. | 435/6 |
| 2008/0306054 | A1 | 12/2008 | Chessari et al. | |

FOREIGN PATENT DOCUMENTS

| | | | |
|---|---|---|---|
| WO | WO 91/03489 | A1 | 3/1991 |
| WO | WO 01/68711 | A1 | 9/2001 |
| WO | WO 2007/001868 | A1 | 1/2007 |

OTHER PUBLICATIONS

Tsavachidou et al., Cancer Research, 64:5556-5559, 2004.*
Argeta, The Oncologist; 2002; V.7 Suppl. 4, 31-39.
Blencke, J of Biological Chemistry 2003, 278(17):15435-15440.
Blencke et al., Chemistry and Biology, 2004, 11, 691-701.
Cohen, Clinical Colorectal Cancer, 2003; 2(4), 246-251.
Doody, Molecular Cancer Ther. 2007; 6(10) 2642-2651.
Foon, Int J Radiation Oncology, Biology, Physics, 2004; 58(3), 984-990.
Freeman, Mol. Cancer Therapy 2009; 8(6).
Gazdar, Trends in Molecular Medicine, 2004, 10:481-486.
Herbst, Int J Radiation Oncology, Biology, Physics, 2004, 59(2) Supp.: 21-26.
Huang, Clinical Cancer Research, 2004, 10: 8195-8203.
Kancha, et al. Clinical Cancer Research, 2009, 15(2) 460-467.
Marchetti, J of Clinical Oncology, 2005, 23: 857-865.
Pao, PLoS Medicine, 2004, Geb. 2005; 2(3), e73,0225-0235.
Pallis, EU J of Chemistry 2009; 45, 2473-2487.
Roskoski, Biochemical and Biophysical Reseach Communications; 2004; V. 319, 1-11.
Saito, Endocrinology; 2004; 145(9), 4232-4243.
Snyder, Clnical Colorectal Cancer, 2005, 5(Supp. 2): S71-S80.
Torring, BJU International, 2002; V89, 583-390.
Witton, J of Pathology; 2003 V200, 290-297.
Allison, "Is personalized medicine finally arriving?" *Nat. Biotech.*, 26: 509-517 (2008).
Amler et al., "Predicting clinical benefit in non-small-cell lung cancer patients treated with epidermal growth factor tyrosine kinase inhibitors." *Cold Spring Harbor Symp. Quant. Biol.*, 70: 483-488 (2005).
Baselga et al., "Determinants of *RAS*istance to anti-epidermal growth factor receptor agents," *J. Clin. Oncol.*, 26: 1582-1584 (2008).
Eberhard et al., "Correlation of mutations in EGFR with clinical outcomes in NSCLC patients treated with erlotinib," *EJC Supplements*, Proceedings of the 16$^{th}$ EORTC-NCI-AACR *Symposium on Molecular Targets and Cancer Therapeutics*. 2: 124 (2004).
Eberhard et al., "Mutations in EGFR, HER2, KRAS and BRAF in NSCLC: Prevalences and correlations with clinical outcomes in patients treated with carboplatin and paclitaxel with or without erlotinib," *Lung Cancer*, 49:S62 (2005).
Finocchiaro et al., "EGFR, HER2 and Kras as predictive factors for cetuximab sensitivity in colorectal cancer," *ASCO*, Abstract No. 4021 (2007).
Moroni et al., "Gene copy of number for epidermal growth factor receptor (EGFR) and clinical response to antiEGFR treatment in colorectal cancer: a cohort study," *Lancet Oncol.*, 6: 279-286 (2005).
Moroni et al., "Somatic mutation of EGFR catalytic domain and treatment with gefitinib in colorectal cancer," *Ann. Onc.*, 16: 1846-1849 (2005).
Sartore-Bianchi et al., "Anti-EGFR monoclonal antibodies in the treatment of non-small cell lung cancer," *Ann. Onc.*, 17(suppl. 2): ii49-ii51 (2006).
Barber et al., "Somatic mutations of *EGFR* in colorectal cancers and glioblastomas," *N. Engl. J. Med*, 351:2883 (2004).
Eberhard et al., "Mutations in the epidermal growth factor receptor and in KRAS are predictive and prognostic indicators in patients with non-small-cell lung cancer treated with chemotherapy alone and in combination with erlotinib," *J. of Clin. Oncol.*, 23:5900-5909 (2005).
Gandara et al., "Epidermal growth factor receptor tyrosine kinase inhibitors plus chemotherapy: case closed or is the jury still out?" *J. of Clin. Oncol.*, 23:5856-5858 (2005).

(Continued)

*Primary Examiner* — Marianne P Allen
(74) *Attorney, Agent, or Firm* — Scott N. Bernstein

(57) ABSTRACT

Mutations of the epidermal growth factor receptor (EGFr), of phosphatidylinositol 3'-kinase ("PI3K"), and of B-Raf are described. Methods of treating tumors containing mutated EGFr with human monoclonal antibodies against EGFr are described. Methods and kits for ascertaining the presence of one or more mutant EGFr, mutant PI3K, and/or mutant B-Raf in a sample and for treating disorders or conditions related to the presence of mutant EGFr, mutant PI3K, and/or mutant B-Raf are also described. Methods of treating tumors containing mutant EGFr, mutant PI3K, and/or mutant B-Raf are also described.

7 Claims, 50 Drawing Sheets

(56) References Cited

OTHER PUBLICATIONS

Hirsh et al., "Biomarkers for prediction of sensitivity to EGFR inhibitors in non-small cell lung cancer," *Curr. Opin. Oncol.*, 17:118-122 (2005).

Hirsh et al., "Epidermal growth factor receptor in non-small-cell lung carcinomas: correlation between gene copy number and protein expression and impact on prognosis," *J. of Clin. Oncol.*, 21: 3798-3807 (2003).

Kobayashi et al., "*EGFR* mutation and resistance of non-small-cell lung cancer to gefitinib," *N. Engl. J. Med.*, 352:786-792 (2005).

Lynch et al., "Activating mutations in the epidermal growth factor receptor underlying responsiveness of non-small-cell lung cancer to gefitinib," *N. Engl. J. Med.*, 350:2129-2139 (2004).

Lynch et al., "A phase II trial of cetuximab as therapy for recurrent non-small cell lung cancer (NSCLC)." *J. of Clin. Oncol., 2004 ASCO Ann. Meeting Proc.*, 22(14S):7084 (2004).

Paez et al., "EGFR mutations in lung cancer: correlation with clinical response to gefitinib therapy," *Science*, 304:1497-1500 (2004).

Pao et al., "EGF receptor gene mutations are common in lung cancers from "never smokers" and are associated with sensitivity of tumors to gefitinib and erlotinib," *PNAS*, 101: 13306-13311 (2004).

Stephens et al., "Intragenic ERBB2 kinase mutations in tumours," *Nature*, 431:525-526 (2004).

Wang et al., "Prevalence of somatic alterations in the colorectal cancer cell genome," *PNAS*, 99:3076-3080 (2002).

* cited by examiner

FIGURE 1

| ATB # | EGFR E18 | EGFR E19 | EGFR E20 | EGFR E21 | EGFR E23 | PIK3 E09 | PIK3 E20 | b-raf E15 |
|---|---|---|---|---|---|---|---|---|
| 16914 | WT (9) | WT (21) | N.D. | WT (8) | WT (6) | TBD | TBD | TBD |
| 16917 | N.D. | WT (12) | N.D. | WT (17) | WT (6) | TBD | TBD | TBD |
| 16928 | WT (8) | WT (38) | WT (14) | WT (46) | WT (17) | TBD | TBD | TBD |
| 16935 | WT (3) | WT (23) | C781R (9/35) | WT (36) | V948A (12/30) | TBD | TBD | TBD |
| 16941 | WT (15) | WT (16) | N.D. | N.D. | N.D. | TBD | TBD | TBD |
| 17093 | WT (62) | WT (9) | HIS insert (2/28) | WT (2) | N.D. | TBD | TBD | TBD |
| 17183 | WT (69) | WT (45) | WT (7) | Q849R (3 of 38) | WT (36) | E545A (1 of 11) | N.D. | WT (11) |
| 17255 | WT (80) | WT (36) | WT (66) | WT (12) | WT (21) | WT (8) | WT (2) | WT (9) |
| 17258 | WT (89) | WT (18) | WT (11) | WT (5) | WT (3) | WT (14) | N.D. | WT (82) |
| 17261 | WT (197) | WT (22) | N.D. | WT (6) | WT (12) | WT (13) | WT (2) | WT (16) |
| 17282 | WT (69) | WT (44) | WT (56) | WT (75) | WT (63) | E545A (4 of 32) | WT (5) | WT (49) |
| 17291 | WT (96) | WT (23) | WT (62) | WT (25) | WT (23) | E545A (16 of 148) | WT (3) | WT (19) |
| 17327 | Q701H (11/195) | WT (2) | WT (107) | WT (23) | WT (15) | WT (3) | N.D. | WT (6) |
| 17330 | WT (89) | WT (31) | WT (39) | WT (114) | WT (27) | E545A (7 of 30) | WT (7) | WT (39) |
| 17363 | L688P (19/69) | 15-bp del (4/26) | WT (40) | WT (24) | WT (21) | WT (29) | WT (33) | WT (5) |
| 17366 | WT (39) | WT (26) | T790M (27/140) | WT (5) | WT (3) | WT (26) | N.D. | N.D. |
| 17369 | WT (128) | WT (22) | WT (34) | WT (29) | WT (49) | N.D. | WT (4) | TBD |
| 17372 | WT (30) | WT (109) | WT (17) | WT (36) | F910L (7 of 84) | E545A (5 of 23) | WT (1) | WT (122) |
| 17891 | WT (34) | K745N (5 of 44) | WT (6) | WT (43) | WT (128) | E545A (38 of 160) | N.D. | V599E (7/44) |
| 17897 | WT (142) | WT (48) | WT (29) | WT (64) | WT (49) | E545A (2 of 31) | N.D. | V599E (7/71) |

FIGURE 2

| ATB # | EGFR E18 | EGFR E19 | EGFR E20 | EGFR E21 | EGFR E23 | PIK3 E9 | PIK3 E20 | b-raf E15 |
|---|---|---|---|---|---|---|---|---|
| 17380 | WT (67) | WT (113) | WT (169) | NO PCR PRODUCT | WT (34) | E545A (9/145) | N.D. | TBD |
| 17383 | WT (47) | WT (56) | WT (82) | WT (34) | WT (101) | E545A (3 of 106) | WT (49) | TBD |
| 17389 | WT (78) | WT (41) | WT (208) | WT (17) | WT (39) | E545A (3 of 11) | WT (7) | TBD |
| 17392 | WT (199) | WT (90) | WT (38) | WT (43) | WT (55) | E545A (1 of 14) | WT (13) | TBD |
| 17395 | WT (225) | N.D. | WT (191) | WT (19) | WT (5) | WT (8) | WT (3) | TBD |
| 17398 | WT (76) | WT (70) | WT (138) | WT (26) | WT (22) | E545A (1 of 20) | WT (13) | TBD |
| 17407 | WT (94) | WT (8) | WT (57) | WT (45) | WT (6) | E545A (8 of 151) | WT (4) | TBD |
| 17410 | WT (141) | WT (68) | WT (37) | WT (41) | WT (51) | E545A (1 of 15) | WT (142) | TBD |
| 17413 | WT (143) | WT (29) | WT (43) | WT (33) | WT (17) | WT (17) | WT (16) | TBD |
| 17419 | WT (99) | WT (48) | WT (58) | WT (30) | WT (2) | E545A (1 of 17) | WT (21) | TBD |
| 17422 | | | | | | | | |
| 17425 | WT (77) | WT (77) | WT (56) | WT (34) | WT (23) | E545A (1 of 39) | H1047 (42 of 110) | TBD |
| 17437 | WT (93) | WT (20) | WT (46) | WT (38) | WT (54) | NO PCR PRODUCT | WT (8) | TBD |
| 17440 | WT (132) | WT (103) | WT (20) | WT (45) | WT (37) | E545A (2 of 37) | N.D. | TBD |
| 17446 | WT (31) | WT (50) | WT (40) | WT (29) | WT (8) | E542K (1 of 25) | WT (23) | TBD |
| 17458 | WT (192) | WT (32) | WT (40) | WT (41) | WT (32) | E545A (1 of 19) | WT (3) | TBD |
| 17464 | WT (221) | NO PCR PRODUCT | N.D. | WT (33) | WT (5) | E542K (4 of 46) | WT (76) | TBD |
| 17467 | WT (115) | WT (34) | WT (61) | WT (39) | WT (10) | E545A (5 of 46) | N.D. | TBD |
| 17470 | WT (79) | WT (54) | WT (134) | WT (20) | WT (107) | E545A (4 of 51) | NO PCR PRODUCT | TBD |
| 17473 | WT (66) | WT (112) | WT (16) | WT (13) | WT (31) | E542K (1 of 32) | WT (5) | TBD |

FIGURE 3: Results of Expanded Mutational Analysis of NSCLC Patient Tumor Samples

| ATB Number | EGFR Exon18 | EGFR Exon19 | EGFR Exon20 | EGFR Exon21 | EGFR Exon23 | b-raf Exon11 | b-raf Exon15 |
|---|---|---|---|---|---|---|---|
| 17096 | WT (36) | WT (75) | WT (41) | WT (43) | WT (49) | WT (54) | WT (84) |
| 17099 | WT (52) | WT (107) | WT (39) | L858R (13 of 81) | WT (59) | WT (43) | WT (49) |
| 17102 | WT (73) | 15bp deletion (43 of 63) | WT (85) | WT (26) | WT (17) | WT (21) | WT (77) |
| 17105 | WT (50) | WT (22) | WT (89) | WT (18) | WT (37) | WT (46) | WT (10) |
| 17108 | WT (94) | WT (9) | WT (60) | WT (42) | WT (43) | WT (30) | WT (116) |
| 17111 | WT (30) | WT (51) | WT (7) | WT (20) | WT (54) | WT (49) | WT (138) |
| 17114 | WT (35) | WT (90) | WT (51) | WT (36) | WT (27) | WT (66) | WT (26) |
| 17117 | WT (20) | WT (2) | WT (24) | WT (47) | WT (34) | WT (79) | WT (53) |
| 17120 | WT (90) | WT (130) | WT (13) | No product | WT (56) | WT (47) | WT (44) |
| 17123 | WT (87) | WT (33) | No product | No product | WT (21) | No product | WT (32) |
| 17126 | WT (29) | WT (31) | WT (69) | WT (28) | WT (25) | WT (57) | WT (30) |
| 17129 | L688P (15 of 145) | WT (40) | WT (9 of 95) | WT (64) | WT (25) | WT (38) | WT (55) |
| 17132 | WT (24) | WT (23) | WT (91) | WT (12) | WT (74) | WT (47) | WT (62) |
| 17135 | WT (87) | No product | No product | WT (4) | WT (90) | WT (9) | WT (58) |
| 17138 | WT (23) | No product | WT (33) | WT (35) | WT (24) | WT (7) | WT (46) |
| 17141 | L688P (11 of 148) | No product | WT (17) | WT (18) | WT (26) | WT (20) | WT (116) |
| 17144 | WT (93) | WT (22) | WT (63) | WT (49) | WT (6) | No product | WT (16) |
| 17147 | WT (19) | WT (6) | WT (29) | WT (49) | WT (31) | WT (65) | WT (163) |
| 17150 | WT (29) | N.D. | N.D. | WT (22) | WT (9) | WT (74) | WT (102) |
| 17153 | WT (21) | WT (81) | WT (90) | WT (25) | WT (52) | WT (23) | WT (10) |
| 17156 | WT (92) | No product | No product | No product | WT (3) | No product | WT (8) |
| 17165 | WT (89) | N.D. | WT (100) | WT (69) | WT (30) | WT (14) | WT (7) |
| 17171 | WT (24) | WT (8) | WT (40) | WT (36) | N.D. | WT (71) | WT (89) |
| 17174 | L688P (12 of 68) | No product | WT (5) | N.D. | WT (21) | WT (92) | WT (12) |
| 17186 | WT (67) | WT (20) | No product | WT (13) | WT (10) | WT (54) | WT (66) |
| 17192 | WT (19) | N.D. | WT (90) | WT (5) | WT (3) | WT (116) | WT (5) |
| 17207 | WT (13) | WT (20) | WT (33) | WT (30) | WT (19) | WT (56) | WT (84) |
| 17231 | WT (92) | No product | WT (131) | No product | WT (20) | WT (8) | No product |
| 17240 | WT (2) | WT (6) | WT (94) | WT (30) | WT (6) | WT (85) | K601E (19 of 184) |
| 17246 | WT (34) | WT (9) | WT (40) | WT (38) | WT (3) | WT (54) | WT (70) |
| 17273 | WT (8) | WT (32) | WT (44) | WT (19) | WT (39) | WT (47) | WT (44) |
| 17285 | L688P (4 of 103) | WT (27) | WT (25) | L828 Stop (8 of 185) | WT (20) | WT (28) | WT (28) |
| 17303 | WT (16) | No product | WT (26) | WT (28) | WT (17) | WT (75) | WT (73) |
| 17306 | WT (88) | WT (13) | WT (37) | WT (102) | WT(10) | WT (23) | No product |
| 17315 | WT (29) | No product | WT (92) | WT (95) | WT (28) | WT (31) | WT (24) |
| 17324 | WT (91) | N.D. | WT (25) | L858R (35 of 238) | WT (2) | WT (71) | N.D. |
| 17333 | No product | N.D. | No product | WT (82) | WT (17) | WT (84) | WT (4) |
| 17339 | WT (33) | WT (18) | No product | L828 Stop (6 of 132) | N.D. | WT (93) | WT (71) |
| 17360 | WT (62) | WT (2) | No product | WT (53) | WT (89) | WT (15) | WT (2) |

*Clinically Observed EGFr Mutation- Differential Sensitivity to Iressa and Panitumumab (in vitro)*

EGFr gene mutation (T790M) found in a NSCLC patient that responded to Paclitaxel / Carboplatin + panitumumab combination therapy

FIGURE 5A

Exon20.txt x His

```
                      .         .         .         .         .
   1 GAAGCCTACGTGATGGCCAGCGTGGACA...ACCCCCACGTGTGCCGCCT 47
     ||||||||||||||||||||||||||||   |||||||||||||||||||
   1 GAAGCCTACGTGATGGCCAGCGTGGACAACCACCCCCACGTGTGCCGCCT 50

                      .         .         .         .         .
  48 GCTGGGCATCTGCCTCACCTCCACCGTGCAACTCATCACGCAGCTCATGC 97
     ||||||||||||||||||||||||||||||||||||||||||||||||||
  51 GCTGGGCATCTGCCTCACCTCCACCGTGCAACTCATCACGCAGCTCATGC 100

                      .         .         .         .         .
  98 CCTTCGGCTGCCTCCTGGACTATGTCCGGGAACACAAAGACAATATTGGC 147
     ||||||||||||||||||||||||||||||||||||||||||||||||||
 101 CCTTCGGCTGCCTCCTGGACTATGTCCGGGAACACAAAGACAATATTGGC 150

                      .         .         .
 148 TCCCAGTACCTGCTCAACTGGTGTGTGCAGATCGCAAAG 186 SEQ ID NO: 52
     |||||||||||||||||||||||||||||||||||||||
 151 TCCCAGTACCTGCTCAACTGGTGTGTGCAGATCGCAAAG 189 SEQ ID NO: 59
```

Exon20.pep x His.pep

```
                      .         .         .         .         .
   1 EAYVMASVDN.PHVCRLLGICLTSTVQLITQLMPFGCLLDYVREHKDNIG 49
     |||||||||| |||||||||||||||||||||||||||||||||||||||
   1 EAYVMASVDNHPHVCRLLGICLTSTVQLITQLMPFGCLLDYVREHKDNIG 50

                      .
  50 SQYLLNWCVQIAK 62 SEQ ID NO: 62
     |||||||||||||
  51 SQYLLNWCVQIAK 63 SEQ ID NO: 21
```

FIGURE 5B

Exon20.txt x T790M.txt

```
                .         .         .         .         .
  1 GAAGCCTACGTGATGGCCAGCGTGGACAACCCCCACGTGTGCCGCCTGCT 50
    ||||||||||||||||||||||||||||||||||||||||||||||||||
  1 GAAGCCTACGTGATGGCCAGCGTGGACAACCCCCACGTGTGCCGCCTGCT 50
                .         .         .         .         .
 51 GGGCATCTGCCTCACCTCCACCGTGCAACTCATCACGCAGCTCATGCCCT 100
    |||||||||||||||||||||||||||||||||||| |||||||||||||
 51 GGGCATCTGCCTCACCTCCACCGTGCAACTCATCATGCAGCTCATGCCCT 100
                .         .         .         .         .
101 TCGGCTGCCTCCTGGACTATGTCCGGGAACACAAAGACAATATTGGCTCC 150
    ||||||||||||||||||||||||||||||||||||||||||||||||||
101 TCGGCTGCCTCCTGGACTATGTCCGGGAACACAAAGACAATATTGGCTCC 150
                .         .         .
151 CAGTACCTGCTCAACTGGTGTGTGCAGATCGCAAAG 186 SEQ ID NO: 63
    ||||||||||||||||||||||||||||||||||||
151 CAGTACCTGCTCAACTGGTGTGTGCAGATCGCAAAG 186 SEQ ID NO: 64
```

Exon20.pep x T790M.pep

```
                .         .         .         .         .
  1 EAYVMASVDNPHVCRLLGICLTSTVQLITQLMPFGCLLDYVREHKDNIGS 50
    |||||||||||||||||||||||||||| |||||||||||||||||||||
  1 EAYVMASVDNPHVCRLLGICLTSTVQLIMQLMPFGCLLDYVREHKDNIGS 50
                .
 51 QYLLNWCVQIAK 62 SEQ ID NO: 65
    ||||||||||||
 51 QYLLNWCVQIAK 62 SEQ ID NO: 66
```

FIGURE 5C

Exon18.txt x Q701H.txt

```
              .         .         .         .         .
  1 CTTGTGGAGCCTCTTACACCCAGTGGAGAAGCTCCCAACCAAGCTCTCTT 50
    |||||||||||||||||||||||||||||||||||||||||| ||||||||
  1 CTTGTGGAGCCTCTTACACCCAGTGGAGAAGCTCCCAACCACGCTCTCTT 50
              .         .         .         .         .
 51 GAGGATCTTGAAGGAAACTGAATTCAAAAAGATCAAAGTGCTGGGCTCCG 100
    ||||||||||||||||||||||||||||||||||||||||||||||||||
 51 GAGGATCTTGAAGGAAACTGAATTCAAAAAGATCAAAGTGCTGGGCTCCG 100
              .         .
101 GTGCGTTCGGCACGGTGTATAAG 123 SEQ ID NO: 67
    |||||||||||||||||||||||
101 GTGCGTTCGGCACGGTGTATAAG 123 SEQ ID NO: 68
```

Exon18.pep x Q701H.pep

```
              .         .         .         .
  1 LVEPLTPSGEAPNQALLRILKETEFKKIKVLGSGAFGTVYK 41 SEQ ID NO: 69
    ||||||||||||| |||||||||||||||||||||||||||
  1 LVEPLTPSGEAPNHALLRILKETEFKKIKVLGSGAFGTVYK 41 SEQ ID NO: 70
```

FIGURE 5D

Exon18.txt x L688P.txt

```
                 .         .         .         .         .
  1 CTTGTGGAGCCTCTTACACCCAGTGGAGAAGCTCCCAACCAAGCTCTCTT 50
    | |||||||||||||||||||||||||||||||||||||||||||||||||
  1 CCTGTGGAGCCTCTTACACCCAGTGGAGAAGCTCCCAACCAAGCTCTCTT 50
                 .         .         .         .         .
 51 GAGGATCTTGAAGGAAACTGAATTCAAAAAGATCAAAGTGCTGGGCTCCG 100
    ||||||||||||||||||||||||||||||||||||||||||||||||||
 51 GAGGATCTTGAAGGAAACTGAATTCAAAAAGATCAAAGTGCTGGGCTCCG 100
                 .         .
101 GTGCGTTCGGCACGGTGTATAAG 123 SEQ ID NO: 71
    |||||||||||||||||||||||
101 GTGCGTTCGGCACGGTGTATAAG 123 SEQ ID NO: 72
```

Exon18.pep x L688P.pep

```
                 .         .         .         .
  1 LVEPLTPSGEAPNQALLRILKETEFKKIKVLGSGAFGTVYK 41 SEQ ID NO: 73
     ||||||||||||||||||||||||||||||||||||||||
  1 PVEPLTPSGEAPNQALLRILKETEFKKIKVLGSGAFGTVYK 41 SEQ ID NO: 74
```

FIGURE 5E

```
PI3K-Exon9.txt x E545A.txt

              .         .         .         .         .
  1 GTAACAGACTAGCTAGAGACAATGAATTAAGGGAAAATGACAAAGAACAG 50
    ||||||||||||||||||||||||||||||||||||||||||||||||||
  1 GTAACAGACTAGCTAGAGACAATGAATTAAGGGAAAATGACAAAGAACAG 50
              .         .         .         .         .
 51 CTCAAAGCAATTTCTACACGAGATCCTCTCTCTGAAATCACTGAGCAGGA 100
    |||||||||||||||||||||||||||||||||||||||||||| ||||||
 51 CTCAAAGCAATTTCTACACGAGATCCTCTCTCTGAAATCACTGCGCAGGA 100
              .         .
101 GAAAGATTTTCTATGGAGTCACAG.... 124 SEQ ID NO: 75
    |||||||||||||||||  |||||
101 GAAAGATTTTCTATGGAC.CACAGGTAA 127 SEQ ID NO: 76


PI3K-Exon9.pep x E545A.pep

              .         .         .         .
  1 NRLARDNELRENDKEQLKAISTRDPLSEITEQEKDFLWSH. 40 SEQ ID NO: 77
    |||||||||||||||||||||||||||||| |||||||.
  1 NRLARDNELRENDKEQLKAISTRDPLSEITAQEKDFLWTTG 41 SEQ ID NO: 78
```

FIGURE 5F

PI3K-Exon20.txt x H1047L.txt

```
    1 GTTTCAGGAGATGTGTTACAAGGCTTATCTAGCTATTCGACAGCATGCCA 50
      ||||||||||||||||||||||||||||||||||||||||||||||||||
    1 GTTTCAGGAGATGTGTTACAAGGCTTATCTAGCTATTCGACAGCATGCCA 50

   51 ATCTCTTCATAAATCTTTTCTCAATGATGCTTGGCTCTGGAATGCCAGAA 100
      ||||||||||||||||||||||||||||||||||||||||||||||||||
   51 ATCTCTTCATAAATCTTTTCTCAATGATGCTTGGCTCTGGAATGCCAGAA 100

  101 CTACAATCTTTTGATGACATTGCATACATTCGAAAGACCCTAGCCTTAGA 150
      ||||||||||||||||||||||||||||||||||||||||||||||||||
  101 CTACAATCTTTTGATGACATTGCATACATTCGAAAGACCCTAGCCTTAGA 150

  151 TAAAACTGAGCAAGAGGCTTTGGAGTATTTCATGAAACAAATGAATGATG 200
      ||||||||||||||||||||||||||||||||||||||||||||||||||
  151 TAAAACTGAGCAAGAGGCTTTGGAGTATTTCATGAAACAAATGAATGATG 200

  201 CACATCATGGTGGCTGGACAACAAAAATGGATTGGATCTTCCACACAATT 250
      ||| ||||||||||||||||||||||||||||||||||||||||||||||
  201 CACTTCATGGTGGCTGGACAACAAAAATGGATTGGATCTTCCACACAATT 250

  251 AAACAGCATGCATTGAACTGA 271 SEQ ID NO: 79
      |||||||||||||||||||||
  251 AAACAGCATGCATTGAACTGA 271 SEQ ID NO: 80
```

PI3K-Exon20.pep x H1047L.pep

```
    1 FQEMCYKAYLAIRQHANLFINLFSMMLGSGMPELQSFDDIAYIRKTLALD 50
      ||||||||||||||||||||||||||||||||||||||||||||||||||
    1 FQEMCYKAYLAIRQHANLFINLFSMMLGSGMPELQSFDDIAYIRKTLALD 50

   51 KTEQEALEYFMKQMNDAHHGGWTTKMDWIFHTIKQHALN* 90 SEQ ID NO: 81
      ||||||||||||||||| ||||||||||||||||||||||
   51 KTEQEALEYFMKQMNDALHGGWTTKMDWIFHTIKQHALN* 90 SEQ ID NO: 82
```

FIGURE 6A

(SEQ ID NO: 55) Wild-type EGFR cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTTGGAGGACCGTCGCTTGG 2500
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA 2600
AGAATACCATGCAGAAGGAGGCAAAGTGCCTATCAAGTGGATGGCATTGGAATCAATTTTACACAGAATCTATACCCACCAGAGTGATGTCTGGAGCTAC 2700
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC 2800
CTCAGCCACCCATATGTACCATCGATGTCTACATGATCATGGTCAAGTGCTGGATGATAGACGCAGATAGTCGCCCAAAGTTCCGTGAGTTGATCATCGA 2900
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC 3000
CTGATGGATGAAGAAGACATGGACGACGTGGTGGATGCCGACGAGTACCTCATCCCACAGCAGGGCTTCTTCAGCAGCCCCTCCACGTCACGGACTCCCC 3100
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA 3200
GCGATACAGCTCAGACCCCACAGGCGCCTTGACTGAGGACAGCATAGACGACACCTTCCTCCCAGTGCCTGAATACATAAACCAGTCCGTTCCCAAAAGG 3300
CCCGCTGGCTCTGTGCAGAATCCTGTCTATCACAATCAGCCTCTGAACCCCGCGCCCAGCAGAGACCCACACTACCAGGACCCCCACAGCACTGCAGTGG 3400
GCAACCCCGAGTATCTCAACACTGTCCAGCCCACCTGTGTCAACAGCACATTCGACAGCCCTGCCCACTGGGCCCAGAAAGGCAGCCACCAAATTAGCCT 3500
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC 3600
GCGCCACAAAGCAGTGAATTTATTGGAGCATGA 3633
```

FIGURE 6B (SEQ ID NO: 1) Wild-type EGFR amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
QALLRILKET EFKKIKVLGS GAFGTVYKGL WIPEGEKVKI PVAIKELREA 750
TSPKANKEIL DEAYVMASVD NPHVCRLLGI CLTSTVQLIT QLMPFGCLLD 800
YVREHKDNIG SQYLLNWCVQ IAKGMNYLED RRLVHRDLAA RNVLVKTPQH 850
VKITDFGLAK LLGAEEKEYH AEGGKVPIKW MALESILHRI YTHQSDVWSY 900
GVTVWELMTF GSKPYDGIPA SEISSILEKG ERLPQPPICT IDVYMIMVKC 950
WMIDADSRPK FRELIIEFSK MARDPQRYLV IQGDERMHLP SPTDSNFYRA 1000
LMDEEDMDDV VDADEYLIPQ QGFFSSPSTS RTPLLSSLSA TSNNSTVACI 1050
DRNGLQSCPI KEDSFLQRYS SDPTGALTED SIDDTFLPVP EYINQSVPKR 1100
PAGSVQNPVY HNQPLNPAPS RDPHYQDPHS TAVGNPEYLN TVQPTCVNST 1150
FDSPAHWAQK GSHQISLDNP DYQQDFFPKE AKPNGIFKGS TAENAEYLRV 1200
APQSSEFIGA                                             1210
```

FIGURE 6C

(SEQ ID NO: 41) EGFR(L688P) cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCCTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTTGGAGGACCGTCGCTTGG 2500
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA 2600
AGAATACCATGCAGAAGGAGGCAAAGTGCCTATCAAGTGGATGGCATTGGAATCAATTTTACACAGAATCTATACCCACCAGAGTGATGTCTGGAGCTAC 2700
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC 2800
CTCAGCCACCCATATGTACCATCGATGTCTACATGATCATGGTCAAGTGCTGGATGATAGACGCAGATAGTCGCCCAAAGTTCCGTGAGTTGATCATCGA 2900
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC 3000
CTGATGGATGAAGAAGACATGGACGACGTGGTGGATGCCGACGAGTACCTCATCCCACAGCAGGGCTTCTTCAGCAGCCCCTCCACGTCACGGACTCCCC 3100
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA 3200
GCGATACAGCTCAGACCCCACAGGCGCCTTGACTGAGGACAGCATAGACGACACCTTCCTCCCAGTGCCTGAATACATAAACCAGTCCGTTCCCAAAAGG 3300
CCCGCTGGCTCTGTGCAGAATCCTGTCTATCACAATCAGCCTCTGAACCCCGCGCCCAGCAGAGACCCACACTACCAGGACCCCCACAGCACTGCAGTGG 3400
GCAACCCCGAGTATCTCAACACTGTCCAGCCCACCTGTGTCAACAGCACATTCGACAGCCCTGCCCACTGGGCCCAGAAAGGCAGCCACCAAATTAGCCT 3500
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC 3600
GCGCCACAAAGCAGTGAATTTATTGGAGCATGA 3633
```

FIGURE 6D

(SEQ ID NO: 2) EGFR(L688P) amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQEREPVE PLTPSGEAPN 700
QALLRILKET EFKKIKVLGS GAFGTVYKGL WIPEGEKVKI PVAIKELREA 750
TSPKANKEIL DEAYVMASVD NPHVCRLLGI CLTSTVQLIT QLMPFGCLLD 800
YVREHKDNIG SQYLLNWCVQ IAKGMNYLED RRLVHRDLAA RNVLVKTPQH 850
VKITDFGLAK LLGAEEKEYH AEGGKVPIKW MALESILHRI YTHQSDVWSY 900
GVTVWELMTF GSKPYDGIPA SEISSILEKG ERLPQPPICT IDVYMIMVKC 950
WMIDADSRPK FRELIIEFSK MARDPQRYLV IQGDERMHLP SPTDSNFYRA 1000
LMDEEDMDDV VDADEYLIPQ QGFFSSPSTS RTPLLSSLSA TSNNSTVACI 1050
DRNGLQSCPI KEDSFLQRYS SDPTGALTED SIDDTFLPVP EYINQSVPKR 1100
PAGSVQNPVY HNQPLNPAPS RDPHYQDPHS TAVGNPEYLN TVQPTCVNST 1150
FDSPAHWAQK GSHQISLDNP DYQQDFFPKE AKPNGIFKGS TAENAEYLRV 1200
APQSSEFIGA                                             1210
```

FIGURE 6E

(SEQ ID NO: 40) EGFR(Q701H) cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CACGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTTGGAGGACCGTCGCTTGG 2500
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA 2600
AGAATACCATGCAGAAGGAGGCAAAGTGCCTATCAAGTGGATGGCATTGGAATCAATTTTACACAGAATCTATACCCACCAGAGTGATGTCTGGAGCTAC 2700
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC 2800
CTCAGCCACCCATATGTACCATCGATGTCTACATGATCATGGTCAAGTGCTGGATGATAGACGCAGATAGTCGCCCAAAGTTCCGTGAGTTGATCATCGA 2900
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC 3000
CTGATGGATGAAGAAGACATGGACGACGTGGTGGATGCCGACGAGTACCTCATCCCACAGCAGGGCTTCTTCAGCAGCCCCTCCACGTCACGGACTCCCC 3100
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA 3200
GCGATACAGCTCAGACCCCACAGGCGCCTTGACTGAGGACAGCATAGACGACACCTTCCTCCCAGTGCCTGAATACATAAACCAGTCCGTTCCCAAAAGG 3300
CCCGCTGGCTCTGTGCAGAATCCTGTCTATCACAATCAGCCTCTGAACCCCGCGCCCAGCAGAGACCCACACTACCAGGACCCCCACAGCACTGCAGTGG 3400
GCAACCCCGAGTATCTCAACACTGTCCAGCCCACCTGTGTCAACAGCACATTCGACAGCCCTGCCCACTGGGCCCAGAAAGGCAGCCACCAAATTAGCCT 3500
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC 3600
GCGCCACAAAGCAGTGAATTTATTGGAGCATGA 3633
```

FIGURE 6F

(SEQ ID NO: 3) EGFR(Q701H) amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
HALLRILKET EFKKIKVLGS GAFGTVYKGL WIPEGEKVKI PVAIKELREA 750
TSPKANKEIL DEAYVMASVD NPHVCRLLGI CLTSTVQLIT QLMPFGCLLD 800
YVREHKDNIG SQYLLNWCVQ IAKGMNYLED RRLVHRDLAA RNVLVKTPQH 850
VKITDFGLAK LLGAEEKEYH AEGGKVPIKW MALESILHRI YTHQSDVWSY 900
GVTVWELMTF GSKPYDGIPA SEISSILEKG ERLPQPPICT IDVYMIMVKC 950
WMIDADSRPK FRELIIEFSK MARDPQRYLV IQGDERMHLP SPTDSNFYRA 1000
LMDEEDMDDV VDADEYLIPQ QGFFSSPSTS RTPLLSSLSA TSNNSTVACI 1050
DRNGLQSCPI KEDSFLQRYS SDPTGALTED SIDDTFLPVP EYINQSVPKR 1100
PAGSVQNPVY HNQPLNPAPS RDPHYQDPHS TAVGNPEYLN TVQPTCVNST 1150
FDSPAHWAQK GSHQISLDNP DYQQDFFPKE AKPNGIFKGS TAENAEYLRV 1200
APQSSEFIGA                                             1210
```

FIGURE 6G (SEQ ID NO: 42) EGFR 15-bp deletion cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAAACATCTCCGAAAGCCAACAAGGAAATCCTCGATGAAGCCTACGTGATGGCCAGCGTGGACAACCC 2300
CCACGTGTGCCGCCTGCTGGGCATCTGCCTCACCTCCACCGTGCAACTCATCACGCAGCTCATGCCCTTCGGCTGCCTCCTGGACTATGTCCGGGAACAC 2400
AAAGACAATATTGGCTCCCAGTACCTGCTCAACTGGTGTGTGCAGATCGCAAAGGGCATGAACTACTTGGAGGACCGTCGCTTGGTGCACCGCGACCTGG 2500
CAGCCAGGAACGTACTGGTGAAAACACCGCAGCATGTCAAGATCACAGATTTTGGGCTGGCCAAACTGCTGGGTGCGGAAGAGAAAGAATACCATGCAGA 2600
AGGAGGCAAAGTGCCTATCAAGTGGATGGCATTGGAATCAATTTTACACAGAATCTATACCCACCAGAGTGATGTCTGGAGCTACGGGGTGACCGTTTGG 2700
GAGTTGATGACCTTTGGATCCAAGCCATATGACGGAATCCCTGCCAGCGAGATCTCCTCCATCCTGGAGAAAGGAGAACGCCTCCCTCAGCCACCCATAT 2800
GTACCATCGATGTCTACATGATCATGGTCAAGTGCTGGATGATAGACGCAGATAGTCGCCCAAAGTTCCGTGAGTTGATCATCGAATTCTCCAAAATGGC 2900
CCGAGACCCCCAGCGCTACCTTGTCATTCAGGGGGATGAAAGAATGCATTTGCCAAGTCCTACAGACTCCAACTTCTACCGTGCCCTGATGGATGAAGAA 3000
GACATGGACGACGTGGTGGATGCCGACGAGTACCTCATCCCACAGCAGGGCTTCTTCAGCAGCCCCTCCACGTCACGGACTCCCCTCCTGAGCTCTCTGA 3100
GTGCAACCAGCAACAATTCCACCGTGGCTTGCATTGATAGAAATGGGCTGCAAAGCTGTCCCATCAAGGAAGACAGCTTCTTGCAGCGATACAGCTCAGA 3200
CCCCACAGGCGCCTTGACTGAGGACAGCATAGACGACACCTTCCTCCCAGTGCCTGAATACATAAACCAGTCCGTTCCCAAAAGGCCCGCTGGCTCTGTG 3300
CAGAATCCTGTCTATCACAATCAGCCTCTGAACCCCGCGCCCAGCAGAGACCCACACTACCAGGACCCCCACAGCACTGCAGTGGGCAACCCCGAGTATC 3400
TCAACACTGTCCAGCCCACCTGTGTCAACAGCACATTCGACAGCCCTGCCCACTGGGCCCAGAAAGGCAGCCACCAAATTAGCCTGGACAACCCTGACTA 3500
CCAGCAGGACTTCTTTCCCAAGGAAGCCAAGCCAAATGGCATCTTTAAGGGCTCCACAGCTGAAAATGCAGAATACCTAAGGGTCGCGCCACAAAGCAGT 3600
GAATTTATTGGAGCATGA 3618
```

FIGURE 6H

(SEQ ID NO: 4) EGFR 15bp deletion amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
QALLRILKET EFKKIKVLGS GAFGTVYKGL WIPEGEKVKI PVAIKTSPKA 750
NKEILDEAYV MASVDNPHVC RLLGICLTST VQLITQLMPF GCLLDYVREH 800
KDNIGSQYLL NWCVQIAKGM NYLEDRRLVH RDLAARNVLV KTPQHVKITD 850
FGLAKLLGAE EKEYHAEGGK VPIKWMALES ILHRIYTHQS DVWSYGVTVW 900
ELMTFGSKPY DGIPASEISS ILEKGERLPQ PPICTIDVYM IMVKCWMIDA 950
DSRPKFRELI IEFSKMARDP QRYLVIQGDE RMHLPSPTDS NFYRALMDEE 1000
DMDDVVDADE YLIPQQGFFS SPSTSRTPLL SSLSATSNNS TVACIDRNGL 1050
QSCPIKEDSF LQRYSSDPTG ALTEDSIDDT FLPVPEYINQ SVPKRPAGSV 1100
QNPVYHNQPL NPAPSRDPHY QDPHSTAVGN PEYLNTVQPT CVNSTFDSPA 1150
HWAQKGSHQI SLDNPDYQQD FFPKEAKPNG IFKGSTAENA EYLRVAPQSS 1200
EFIGA                                                  1205
```

FIGURE 6I

(SEQ ID NO: 43) EGFR(K745N) cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAATGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTTGGAGGACCGTCGCTTGG 2500
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA 2600
AGAATACCATGCAGAAGGAGGCAAAGTGCCTATCAAGTGGATGGCATTGGAATCAATTTTACACAGAATCTATACCCACCAGAGTGATGTCTGGAGCTAC 2700
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC 2800
CTCAGCCACCCATATGTACCATCGATGTCTACATGATCATGGTCAAGTGCTGGATGATAGACGCAGATAGTCGCCCAAAGTTCCGTGAGTTGATCATCGA 2900
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC 3000
CTGATGGATGAAGAAGACATGGACGACGTGGTGGATGCCGACGAGTACCTCATCCCACAGCAGGGCTTCTTCAGCAGCCCCTCCACGTCACGGACTCCCC 3100
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA 3200
GCGATACAGCTCAGACCCCACAGGCGCCTTGACTGAGGACAGCATAGACGACACCTTCCTCCCAGTGCCTGAATACATAAACCAGTCCGTTCCCAAAAGG 3300
CCCGCTGGCTCTGTGCAGAATCCTGTCTATCACAATCAGCCTCTGAACCCCGCGCCCAGCAGAGACCCACACTACCAGGACCCCCACAGCACTGCAGTGG 3400
GCAACCCCGAGTATCTCAACACTGTCCAGCCCACCTGTGTCAACAGCACATTCGACAGCCCTGCCCACTGGGCCCAGAAAGGCAGCCACCAAATTAGCCT 3500
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC 3600
GCGCCACAAAGCAGTGAATTTATTGGAGCATGA 3633
```

FIGURE 6J

(SEQ ID NO: 5) EGFR(K745N) amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
QALLRILKET EFKKIKVLGS GAFGTVYKGL WIPEGEKVKI PVAINELREA 750
TSPKANKEIL DEAYVMASVD NPHVCRLLGI CLTSTVQLIT QLMPFGCLLD 800
YVREHKDNIG SQYLLNWCVQ IAKGMNYLED RRLVHRDLAA RNVLVKTPQH 850
VKITDFGLAK LLGAEEKEYH AEGGKVPIKW MALESILHRI YTHQSDVWSY 900
GVTVWELMTF GSKPYDGIPA SEISSILEKG ERLPQPPICT IDVYMIMVKC 950
WMIDADSRPK FRELIIEFSK MARDPQRYLV IQGDERMHLP SPTDSNFYRA 1000
LMDEEDMDDV VDADEYLIPQ QGFFSSPSTS RTPLLSSLSA TSNNSTVACI 1050
DRNGLQSCPI KEDSFLQRYS SDPTGALTED SIDDTFLPVP EYINQSVPKR 1100
PAGSVQNPVY HNQPLNPAPS RDPHYQDPHS TAVGNPEYLN TVQPTCVNST 1150
FDSPAHWAQK GSHQISLDNP DYQQDFFPKE AKPNGIFKGS TAENAEYLRV 1200
APQSSEFIGA                                             1210
```

FIGURE 6K

(SEQ ID NO: 44) EGFR(C781R) cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCCGCCTCACCTCCACCGTGCAACTCATCACGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTTGGAGGACCGTCGCTTGG 2500
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA 2600
AGAATACCATGCAGAAGGAGGCAAAGTGCCTATCAAGTGGATGGCATTGGAATCAATTTTACACAGAATCTATACCCACCAGAGTGATGTCTGGAGCTAC 2700
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC 2800
CTCAGCCACCCATATGTACCATCGATGTCTACATGATCATGGTCAAGTGCTGGATGATAGACGCAGATAGTCGCCCAAAGTTCCGTGAGTTGATCATCGA 2900
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC 3000
CTGATGGATGAAGAAGACATGGACGACGTGGTGGATGCCGACGAGTACCTCATCCCACAGCAGGGCTTCTTCAGCAGCCCCTCCACGTCACGGACTCCCC 3100
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA 3200
GCGATACAGCTCAGACCCCACAGGCGCCTTGACTGAGGACAGCATAGACGACACCTTCCTCCCAGTGCCTGAATACATAAACCAGTCCGTTCCCAAAAGG 3300
CCCGCTGGCTCTGTGCAGAATCCTGTCTATCACAATCAGCCTCTGAACCCCGCGCCCAGCAGAGACCCACACTACCAGGACCCCCACAGCACTGCAGTGG 3400
GCAACCCCGAGTATCTCAACACTGTCCAGCCCACCTGTGTCAACAGCACATTCGACAGCCCTGCCCACTGGGCCCAGAAAGGCAGCCACCAAATTAGCCT 3500
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC 3600
GCGCCACAAAGCAGTGAATTTATTGGAGCATGA 3633
```

FIGURE 6L

(SEQ ID NO: 6) EGFR(C781R) amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
QALLRILKET EFKKIKVLGS GAFGTVYKGL WIPEGEKVKI PVAIKELREA 750
TSPKANKEIL DEAYVMASVD NPHVCRLLGI RLTSTVQLIT QLMPFGCLLD 800
YVREHKDNIG SQYLLNWCVQ IAKGMNYLED RRLVHRDLAA RNVLVKTPQH 850
VKITDFGLAK LLGAEEKEYH AEGGKVPIKW MALESILHRI YTHQSDVWSY 900
GVTVWELMTF GSKPYDGIPA SEISSILEKG ERLPQPPICT IDVYMIMVKC 950
WMIDADSRPK FRELIIEFSK MARDPQRYLV IQGDERMHLP SPTDSNFYRA 1000
LMDEEDMDDV VDADEYLIPQ QGFFSSPSTS RTPLLSSLSA TSNNSTVACI 1050
DRNGLQSCPI KEDSFLQRYS SDPTGALTED SIDDTFLPVP EYINQSVPKR 1100
PAGSVQNPVY HNQPLNPAPS RDPHYQDPHS TAVGNPEYLN TVQPTCVNST 1150
FDSPAHWAQK GSHQISLDNP DYQQDFFPKE AKPNGIFKGS TAENAEYLRV 1200
APQSSEFIGA                                             1210
```

FIGURE 6M

(SEQ ID NO: 46) EGFR HIS insertion after amino acid position 771 cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCACCCCCACGTGTGCCGCCTGCTGGGCATCTGCCTCACCTCCACCGTGCAACTCATCACGCAGCTCATGCCCTTCGGCTGCCTCCTG 2400
GACTATGTCCGGGAACACAAAGACAATATTGGCTCCCAGTACCTGCTCAACTGGTGTGTGCAGATCGCAAAGGGCATGAACTACTTGGAGGACCGTCGCT 2500
TGGTGCACCGCGACCTGGCAGCCAGGAACGTACTGGTGAAAACACCGCAGCATGTCAAGATCACAGATTTTGGGCTGGCCAAACTGCTGGGTGCGGAAGA 2600
GAAAGAATACCATGCAGAAGGAGGCAAAGTGCCTATCAAGTGGATGGCATTGGAATCAATTTTACACAGAATCTATACCCACCAGAGTGATGTCTGGAGC 2700
TACGGGGTGACCGTTTGGGAGTTGATGACCTTTGGATCCAAGCCATATGACGGAATCCCTGCCAGCGAGATCTCCTCCATCCTGGAGAAAGGAGAACGCC 2800
TCCCTCAGCCACCCATATGTACCATCGATGTCTACATGATCATGGTCAAGTGCTGGATGATAGACGCAGATAGTCGCCCAAAGTTCCGTGAGTTGATCAT 2900
CGAATTCTCCAAAATGGCCCGAGACCCCCAGCGCTACCTTGTCATTCAGGGGGATGAAAGAATGCATTTGCCAAGTCCTACAGACTCCAACTTCTACCGT 3000
GCCCTGATGGATGAAGAAGACATGGACGACGTGGTGGATGCCGACGAGTACCTCATCCCACAGCAGGGCTTCTTCAGCAGCCCCTCCACGTCACGGACTC 3100
CCCTCCTGAGCTCTCTGAGTGCAACCAGCAACAATTCCACCGTGGCTTGCATTGATAGAAATGGGCTGCAAAGCTGTCCCATCAAGGAAGACAGCTTCTT 3200
GCAGCGATACAGCTCAGACCCCACAGGCGCCTTGACTGAGGACAGCATAGACGACACCTTCCTCCCAGTGCCTGAATACATAAACCAGTCCGTTCCCAAA 3300
AGGCCCGCTGGCTCTGTGCAGAATCCTGTCTATCACAATCAGCCTCTGAACCCCGCGCCCAGCAGAGACCCACACTACCAGGACCCCCACAGCACTGCAG 3400
TGGGCAACCCCGAGTATCTCAACACTGTCCAGCCCACCTGTGTCAACAGCACATTCGACAGCCCTGCCCACTGGGCCCAGAAAGGCAGCCACCAAATTAG 3500
CCTGGACAACCCTGACTACCAGCAGGACTTCTTTCCCAAGGAAGCCAAGCCAAATGGCATCTTTAAGGGCTCCACAGCTGAAAATGCAGAATACCTAAGG 3600
GTCGCGCCACAAAGCAGTGAATTTATTGGAGCATGA 3636
```

FIGURE 6N

(SEQ ID NO: 7) EGFR HIS insertion after amino acid position 771 amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
QALLRILKET EFKKIKVLGS GAFGTVYKGL WIPEGEKVKI PVAIKELREA 750
TSPKANKEIL DEAYVMASVD NHPHVCRLLG ICLTSTVQLI TQLMPFGCLL 800
DYVREHKDNI GSQYLLNWCV QIAKGMNYLE DRRLVHRDLA ARNVLVKTPQ 850
HVKITDFGLA KLLGAEEKEY HAEGGKVPIK WMALESILHR IYTHQSDVWS 900
YGVTVWELMT FGSKPYDGIP ASEISSILEK GERLPQPPIC TIDVYMIMVK 950
CWMIDADSRP KFRELIIEFS KMARDPQRYL VIQGDERMHL PSPTDSNFYR 1000
ALMDEEDMDD VVDADEYLIP QQGFFSSPST SRTPLLSSLS ATSNNSTVAC 1050
IDRNGLQSCP IKEDSFLQRY SSDPTGALTE DSIDDTFLPV PEYINQSVPK 1100
RPAGSVQNPV YHNQPLNPAP SRDPHYQDPH STAVGNPEYL NTVQPTCVNS 1150
TFDSPAHWAQ KGSHQISLDN PDYQQDFFPK EAKPNGIFKG STAENAEYLR 1200
VAPQSSEFIG A                                           1211
```

FIGURE 60

(SEQ ID NO: 45) EGFR(T790M) cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCTGCCTCACCTCCACCGTGCAACTCATCATGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTTGGAGGACCGTCGCTTGG 2500
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA 2600
AGAATACCATGCAGAAGGAGGCAAAGTGCCTATCAAGTGGATGGCATTGGAATCAATTTTACACAGAATCTATACCCACCAGAGTGATGTCTGGAGCTAC 2700
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC 2800
CTCAGCCACCCATATGTACCATCGATGTCTACATGATCATGGTCAAGTGCTGGATGATAGACGCAGATAGTCGCCCAAAGTTCCGTGAGTTGATCATCGA 2900
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC 3000
CTGATGGATGAAGAAGACATGGACGACGTGGTGGATGCCGACGAGTACCTCATCCCACAGCAGGGCTTCTTCAGCAGCCCCTCCACGTCACGGACTCCCC 3100
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA 3200
GCGATACAGCTCAGACCCCACAGGCGCCTTGACTGAGGACAGCATAGACGACACCTTCCTCCCAGTGCCTGAATACATAAACCAGTCCGTTCCCAAAAGG 3300
CCCGCTGGCTCTGTGCAGAATCCTGTCTATCACAATCAGCCTCTGAACCCCGCGCCCAGCAGAGACCCACACTACCAGGACCCCCACAGCACTGCAGTGG 3400
GCAACCCCGAGTATCTCAACACTGTCCAGCCCACCTGTGTCAACAGCACATTCGACAGCCCTGCCCACTGGGCCCAGAAAGGCAGCCACCAAATTAGCCT 3500
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC 3600
GCGCCACAAAGCAGTGAATTTATTGGAGCATGA 3633
```

FIGURE 6P

(SEQ ID NO: 8) EGFR(T790M) amino acid

```
MRPSGTAGAA LLALLAALCP ASRALEEKKV CQGTSNKLTQ LGTFEDHFLS 50
LQRMFNNCEV VLGNLEITYV QRNYDLSFLK TIQEVAGYVL IALNTVERIP 100
LENLQIIRGN MYYENSYALA VLSNYDANKT GLKELPMRNL QEILHGAVRF 150
SNNPALCNVE SIQWRDIVSS DFLSNMSMDF QNHLGSCQKC DPSCPNGSCW 200
GAGEENCQKL TKIICAQQCS GRCRGKSPSD CCHNQCAAGC TGPRESDCLV 250
CRKFRDEATC KDTCPPLMLY NPTTYQMDVN PEGKYSFGAT CVKKCPRNYV 300
VTDHGSCVRA CGADSYEMEE DGVRKCKKCE GPCRKVCNGI GIGEFKDSLS 350
INATNIKHFK NCTSISGDLH ILPVAFRGDS FTHTPPLDPQ ELDILKTVKE 400
ITGFLLIQAW PENRTDLHAF ENLEIIRGRT KQHGQFSLAV VSLNITSLGL 450
RSLKEISDGD VIISGNKNLC YANTINWKKL FGTSGQKTKI ISNRGENSCK 500
ATGQVCHALC SPEGCWGPEP RDCVSCRNVS RGRECVDKCK LLEGEPREFV 550
ENSECIQCHP ECLPQAMNIT CTGRGPDNCI QCAHYIDGPH CVKTCPAGVM 600
GENNTLVWKY ADAGHVCHLC HPNCTYGCTG PGLEGCPTNG PKIPSIATGM 650
VGALLLLLVV ALGIGLFMRR RHIVRKRTLR RLLQERELVE PLTPSGEAPN 700
QALLRILKET EFKKIKVLGS GAFGTVYKGL WIPEGEKVKI PVAIKELREA 750
TSPKANKEIL DEAYVMASVD NPHVCRLLGI CLTSTVQLIM QLMPFGCLLD 800
YVREHKDNIG SQYLLNWCVQ IAKGMNYLED RRLVHRDLAA RNVLVKTPQH 850
VKITDFGLAK LLGAEEKEYH AEGGKVPIKW MALESILHRI YTHQSDVWSY 900
GVTVWELMTF GSKPYDGIPA SEISSILEKG ERLPQPPICT IDVYMIMVKC 950
WMIDADSRPK FRELIIEFSK MARDPQRYLV IQGDERMHLP SPTDSNFYRA 1000
LMDEEDMDDV VDADEYLIPQ QGFFSSPSTS RTPLLSSLSA TSNNSTVACI 1050
DRNGLQSCPI KEDSFLQRYS SDPTGALTED SIDDTFLPVP EYINQSVPKR 1100
PAGSVQNPVY HNQPLNPAPS RDPHYQDPHS TAVGNPEYLN TVQPTCVNST 1150
FDSPAHWAQK GSHQISLDNP DYQQDFFPKE AKPNGIFKGS TAENAEYLRV 1200
APQSSEFIGA                                         1210
```

FIGURE 6Q

(SEQ ID NO: 56) EGFR L828stop cDNA

```
ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA 100
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT 200
TACCTATGTGCAGAGGAATTATGATCTTTCCTTCTTAAAGACCATCCAGGAGGTGGCTGGTTATGTCCTCATTGCCCTCAACACAGTGGAGCGAATTCCT 300
TTGGAAAACCTGCAGATCATCAGAGGAAATATGTACTACGAAAATTCCTATGCCTTAGCAGTCTTATCTAACTATGATGCAAATAAAACCGGACTGAAGG 400
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT 500
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG 600
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA 700
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT 800
CATGCTCTACAACCCCACCACGTACCAGATGGATGTGAACCCCGAGGGCAAATACAGCTTTGGTGCCACCTGCGTGAAGAAGTGTCCCCGTAATTATGTG 900
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC 1000
GCAAAGTGTGTAACGGAATAGGTATTGGTGAATTTAAAGACTCACTCTCCATAAATGCTACGAATATTAAACACTTCAAAAACTGCACCTCCATCAGTGG 1100
CGATCTCCACATCCTGCCGGTGGCATTTAGGGGTGACTCCTTCACACATACTCCTCCTCTGGATCCACAGGAACTGGATATTCTGAAAACCGTAAAGGAA 1200
ATCACAGGGTTTTTGCTGATTCAGGCTTGGCCTGAAAACAGGACGGACCTCCATGCCTTTGAGAACCTAGAAATCATACGCGGCAGGACCAAGCAACATG 1300
GTCAGTTTTCTCTTGCAGTCGTCAGCCTGAACATAACATCCTTGGGATTACGCTCCCTCAAGGAGATAAGTGATGGAGATGTGATAATTTCAGGAAACAA 1400
AAATTTGTGCTATGCAAATACAATAAACTGGAAAAAACTGTTTGGGACCTCCGGTCAGAAAACCAAAATTATAAGCAACAGAGGTGAAAACAGCTGCAAG 1500
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG 1600
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT 1700
GAACATCACCTGCACAGGACGGGGACCAGACAACTGTATCCAGTGTGCCCACTACATTGACGGCCCCCACTGCGTCAAGACCTGCCCGGCAGGAGTCATG 1800
GGAGAAAACAACACCCTGGTCTGGAAGTACGCAGACGCCGGCCATGTGTGCCACCTGTGCCATCCAAACTGCACCTACGGATGCACTGGGCCAGGTCTTG 1900
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT 2000
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC 2100
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG 2200
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC 2300
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC 2400
TATGTCCGGGAACACAAAGACAATATTGGCTCCCAGTACCTGCTCAACTGGTGTGTGCAGATCGCAAAGGGCATGAACTACTAG 2484
```

FIGURE 6R

(SEQ ID NO: 9) EGFR L828stop amino acid

MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCKLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNY

FIGURE 6S

(SEQ ID NO: 47) EGFR(Q849R) cDNA

ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT
TACCTATGTGCAGAGGAATTATGATCTTTCCTTCTTAAAGACCATCCAGGAGGTGGCTGGTTATGTCCTCATTGCCCTCAACACAGTGGAGCGAATTCCT
TTGGAAAACCTGCAGATCATCAGAGGAAATATGTACTACGAAAATTCCTATGCCTTAGCAGTCTTATCTAACTATGATGCAAATAAAACCGGACTGAAGG
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT
CATGCTCTACAACCCCACCACGTACCAGATGGATGTGAACCCCGAGGGCAAATACAGCTTTGGTGCCACCTGCGTGAAGAAGTGTCCCCGTAATTATGTG
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC
GCAAAGTGTGTAACGGAATAGGTATTGGTGAATTTAAAGACTCACTCTCCATAAATGCTACGAATATTAAACACTTCAAAAACTGCACCTCCATCAGTGG
CGATCTCCACATCCTGCCGGTGGCATTTAGGGGTGACTCCTTCACACATACTCCTCCTCTGGATCCACAGGAACTGGATATTCTGAAAACCGTAAAGGAA
ATCACAGGGTTTTTGCTGATTCAGGCTTGGCCTGAAAACAGGACGGACCTCCATGCCTTTGAGAACCTAGAAATCATACGCGGCAGGACCAAGCAACATG
GTCAGTTTTCTCTTGCAGTCGTCAGCCTGAACATAACATCCTTGGGATTACGCTCCCTCAAGGAGATAAGTGATGGAGATGTGATAATTTCAGGAAACAA
AAATTTGTGCTATGCAAATACAATAAACTGGAAAAAACTGTTTGGGACCTCCGGTCAGAAAACCAAAATTATAAGCAACAGAGGTGAAAACAGCTGCAAG
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT
GAACATCACCTGCACAGGACGGGGACCAGACAACTGTATCCAGTGTGCCCACTACATTGACGGCCCCCACTGCGTCAAGACCTGCCCGGCAGGAGTCATG
GGAGAAAACAACACCCTGGTCTGGAAGTACGCAGACGCCGGCCATGTGTGCCACCTGTGCCATCCAAACTGCACCTACGGATGCACTGGGCCAGGTCTTG
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC
TATGTCCGGGAACACAAAGACAATATTGGCTCCCAGTACCTGCTCAACTGGTGTGTGCAGATCGCAAAGGGCATGAACTACTTGGAGGACCGTCGCTTGG
TGCACCGCGACCTGGCAGCCAGGAACGTACTGGTGAAAACACCGCGGCATGTCAAGATCACAGATTTTGGGCTGGCCAAACTGCTGGGTGCGGAAGAGAA
AGAATACCATGCAGAAGGAGGCAAAGTGCCTATCAAGTGGATGGCATTGGAATCAATTTTACACAGAATCTATACCCACCAGAGTGATGTCTGGAGCTAC
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC
CTCAGCCACCCATATGTACCATCGATGTCTACATGATCATGGTCAAGTGCTGGATGATAGACGCAGATAGTCGCCCAAAGTTCCGTGAGTTGATCATCGA
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC
CTGATGGATGAAGAAGACATGGACGACGTGGTGGATGCCGACGAGTACCTCATCCCACAGCAGGGCTTCTTCAGCAGCCCCTCCACGTCACGGACTCCCC
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA
GCGATACAGCTCAGACCCCACAGGCGCCTTGACTGAGGACAGCATAGACGACACCTTCCTCCCAGTGCCTGAATACATAAACCAGTCCGTTCCCAAAAGG
CCCGCTGGCTCTGTGCAGAATCCTGTCTATCACAATCAGCCTCTGAACCCCGCGCCCAGCAGAGACCCACACTACCAGGACCCCCACAGCACTGCAGTGG
GCAACCCCGAGTATCTCAACACTGTCCAGCCCACCTGTGTCAACAGCACATTCGACAGCCCTGCCCACTGGGCCCAGAAAGGCAGCCACCAAATTAGCCT
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC
GCGCCACAAAGCAGTGAATTTATTGGAGCATGA

FIGURE 6T

(SEQ ID NO: 10) EGFR(Q849R) amino acid

```
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCKLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPRH
VKITDFGLAKLLGAEEKEYHAEGGKVPIKWMALESILHRIYTHQSDVWSY
GVTVWELMTFGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA
```

FIGURE 6U (SEQ ID NO: 61) EGFR(L858R) cDNA

ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT
TACCTATGTGCAGAGGAATTATGATCTTTCCTTCTTAAAGACCATCCAGGAGGTGGCTGGTTATGTCCTCATTGCCCTCAACACAGTGGAGCGAATTCCT
TTGGAAAACCTGCAGATCATCAGAGGAAATATGTACTACGAAAATTCCTATGCCTTAGCAGTCTTATCTAACTATGATGCAAATAAAACCGGACTGAAGG
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT
CATGCTCTACAACCCCACCACGTACCAGATGGATGTGAACCCCGAGGGCAAATACAGCTTTGGTGCCACCTGCGTGAAGAAGTGTCCCCGTAATTATGTG
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC
GCAAAGTGTGTAACGGAATAGGTATTGGTGAATTTAAAGACTCACTCTCCATAAATGCTACGAATATTAAACACTTCAAAAACTGCACCTCCATCAGTGG
CGATCTCCACATCCTGCCGGTGGCATTTAGGGGTGACTCCTTCACACATACTCCTCCTCTGGATCCACAGGAACTGGATATTCTGAAAACCGTAAAGGAA
ATCACAGGGTTTTTGCTGATTCAGGCTTGGCCTGAAAACAGGACGGACCTCCATGCCTTTGAGAACCTAGAAATCATACGCGGCAGGACCAAGCAACATG
GTCAGTTTTCTCTTGCAGTCGTCAGCCTGAACATAACATCCTTGGGATTACGCTCCCTCAAGGAGATAAGTGATGGAGATGTGATAATTTCAGGAAACAA
AAATTTGTGCTATGCAAATACAATAAACTGGAAAAAACTGTTTGGGACCTCCGGTCAGAAAACCAAAATTATAAGCAACAGAGGTGAAAACAGCTGCAAG
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT
GAACATCACCTGCACAGGACGGGGACCAGACAACTGTATCCAGTGTGCCCACTACATTGACGGCCCCCACTGCGTCAAGACCTGCCCGGCAGGAGTCATG
GGAGAAAACAACACCCTGGTCTGGAAGTACGCAGACGCCGGCCATGTGTGCCACCTGTGCCATCCAAACTGCACCTACGGATGCACTGGGCCAGGTCTTG
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC
TATGTCCGGGAACACAAAGACAATATTGGCTCCCAGTACCTGCTCAACTGGTGTGTGCAGATCGCAAAGGGCATGAACTACTTGGAGGACCGTCGCTTGG
TGCACCGCGACCTGGCAGCCAGGAACGTACTGGTGAAAACACCGCAGCATGTCAAGATCACAGATTTTGGGCGGGCCAAACTGCTGGGTGCGGAAGAGAA
AGAATACCATGCAGAAGGAGGCAAAGTGCCTATCAAGTGGATGGCATTGGAATCAATTTTACACAGAATCTATACCCACCAGAGTGATGTCTGGAGCTAC
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC
CTCAGCCACCCATATGTACCATCGATGTCTACATGATCATGGTCAAGTGCTGGATGATAGACGCAGATAGTCGCCCAAAGTTCCGTGAGTTGATCATCGA
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC
CTGATGGATGAAGAAGACATGGACGACGTGGTGGATGCCGACGAGTACCTCATCCCACAGCAGGGCTTCTTCAGCAGCCCCTCCACGTCACGGACTCCCC
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA
GCGATACAGCTCAGACCCCACAGGCGCCTTGACTGAGGACAGCATAGACGACACCTTCCTCCCAGTGCCTGAATACATAAACCAGTCCGTTCCCAAAAGG
CCCGCTGGCTCTGTGCAGAATCCTGTCTATCACAATCAGCCTCTGAACCCCGCGCCCAGCAGAGACCCACACTACCAGGACCCCCACAGCACTGCAGTGG
GCAACCCCGAGTATCTCAACACTGTCCAGCCCACCTGTGTCAACAGCACATTCGACAGCCCTGCCCACTGGGCCCAGAAAGGCAGCCACCAAATTAGCCT
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC
GCGCCACAAAGCAGTGAATTTATTGGAGCATGA

FIGURE 6V

(SEQ ID NO: 11) EGFR(L858R) amino acid

MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCKLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGRAKLLGAEEKEYHAEGGKVPIKWMALESILHRIYTHQSDVWSY
GVTVWELMTFGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA

FIGURE 6W

(SEQ ID NO: 49) EGFR(F910L) cDNA

ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT
TACCTATGTGCAGAGGAATTATGATCTTTCCTTCTTAAAGACCATCCAGGAGGTGGCTGGTTATGTCCTCATTGCCCTCAACACAGTGGAGCGAATTCCT
TTGGAAAACCTGCAGATCATCAGAGGAAATATGTACTACGAAAATTCCTATGCCTTAGCAGTCTTATCTAACTATGATGCAAATAAAACCGGACTGAAGG
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT
CATGCTCTACAACCCCACCACGTACCAGATGGATGTGAACCCCGAGGGCAAATACAGCTTTGGTGCCACCTGCGTGAAGAAGTGTCCCCGTAATTATGTG
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC
GCAAAGTGTGTAACGGAATAGGTATTGGTGAATTTAAAGACTCACTCTCCATAAATGCTACGAATATTAAACACTTCAAAAACTGCACCTCCATCAGTGG
CGATCTCCACATCCTGCCGGTGGCATTTAGGGGTGACTCCTTCACACATACTCCTCCTCTGGATCCACAGGAACTGGATATTCTGAAAACCGTAAAGGAA
ATCACAGGGTTTTTGCTGATTCAGGCTTGGCCTGAAAACAGGACGGACCTCCATGCCTTTGAGAACCTAGAAATCATACGCGGCAGGACCAAGCAACATG
GTCAGTTTTCTCTTGCAGTCGTCAGCCTGAACATAACATCCTTGGGATTACGCTCCCTCAAGGAGATAAGTGATGGAGATGTGATAATTTCAGGAAACAA
AAATTTGTGCTATGCAAATACAATAAACTGGAAAAAACTGTTTGGGACCTCCGGTCAGAAAACCAAAATTATAAGCAACAGAGGTGAAAACAGCTGCAAG
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT
GAACATCACCTGCACAGGACGGGGACCAGACAACTGTATCCAGTGTGCCCACTACATTGACGGCCCCCACTGCGTCAAGACCTGCCCGGCAGGAGTCATG
GGAGAAAACAACACCCTGGTCTGGAAGTACGCAGACGCCGGCCATGTGTGCCACCTGTGCCATCCAAACTGCACCTACGGATGCACTGGGCCAGGTCTTG
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC
TATGTCCGGGAACACAAAGACAATATTGGCTCCCAGTACCTGCTCAACTGGTGTGTGCAGATCGCAAAGGGCATGAACTACTTGGAGGACCGTCGCTTGG
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA
AGAATACCATGCAGAAGGAGGCAAAGTGCCTATCAAGTGGATGGCATTGGAATCAATTTTACACAGAATCTATACCCACCAGAGTGATGTCTGGAGCTAC
GGGGTGACCGTTTGGGAGTTGATGACCCTTGGATCCAAGCCATATGACGGAATCCCTGCCAGCGAGATCTCCTCCATCCTGGAGAAAGGAGAACGCCTCC
CTCAGCCACCCATATGTACCATCGATGTCTACATGATCATGGTCAAGTGCTGGATGATAGACGCAGATAGTCGCCCAAAGTTCCGTGAGTTGATCATCGA
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC
CTGATGGATGAAGAAGACATGGACGACGTGGTGGATGCCGACGAGTACCTCATCCCACAGCAGGGCTTCTTCAGCAGCCCCTCCACGTCACGGACTCCCC
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA
GCGATACAGCTCAGACCCCACAGGCGCCTTGACTGAGGACAGCATAGACGACACCTTCCTCCCAGTGCCTGAATACATAAACCAGTCCGTTCCCAAAAGG
CCCGCTGGCTCTGTGCAGAATCCTGTCTATCACAATCAGCCTCTGAACCCCGCGCCCAGCAGAGACCCACACTACCAGGACCCCCACAGCACTGCAGTGG
GCAACCCCGAGTATCTCAACACTGTCCAGCCCACCTGTGTCAACAGCACATTCGACAGCCCTGCCCACTGGGCCCAGAAAGGCAGCCACCAAATTAGCCT
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC
GCGCCACAAAGCAGTGAATTTATTGGAGCATGA

FIGURE 6X

(SEQ ID NO: 12) EGFR(F910L) amino acid

MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCKLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
GVTVWELMTLGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA

FIGURE 6Y (SEQ ID NO: 48) EGFR(V948A) cDNA

ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCA
CGAGTAACAAGCTCACGCAGTTGGGCACTTTTGAAGATCATTTTCTCAGCCTCCAGAGGATGTTCAATAACTGTGAGGTGGTCCTTGGGAATTTGGAAAT
TACCTATGTGCAGAGGAATTATGATCTTTCCTTCTTAAAGACCATCCAGGAGGTGGCTGGTTATGTCCTCATTGCCCTCAACACAGTGGAGCGAATTCCT
TTGGAAAACCTGCAGATCATCAGAGGAAATATGTACTACGAAAATTCCTATGCCTTAGCAGTCTTATCTAACTATGATGCAAATAAAACCGGACTGAAGG
AGCTGCCCATGAGAAATTTACAGGAAATCCTGCATGGCGCCGTGCGGTTCAGCAACAACCCTGCCCTGTGCAACGTGGAGAGCATCCAGTGGCGGGACAT
AGTCAGCAGTGACTTTCTCAGCAACATGTCGATGGACTTCCAGAACCACCTGGGCAGCTGCCAAAAGTGTGATCCAAGCTGTCCCAATGGGAGCTGCTGG
GGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACA
ACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACT
CATGCTCTACAACCCCACCACGTACCAGATGGATGTGAACCCCGAGGGCAAATACAGCTTTGGTGCCACCTGCGTGAAGAAGTGTCCCCGTAATTATGTG
GTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCC
GCAAAGTGTGTAACGGAATAGGTATTGGTGAATTTAAAGACTCACTCTCCATAAATGCTACGAATATTAAACACTTCAAAAACTGCACCTCCATCAGTGG
CGATCTCCACATCCTGCCGGTGGCATTTAGGGGTGACTCCTTCACACATACTCCTCCTCTGGATCCACAGGAACTGGATATTCTGAAAACCGTAAAGGAA
ATCACAGGGTTTTTGCTGATTCAGGCTTGGCCTGAAAACAGGACGGACCTCCATGCCTTTGAGAACCTAGAAATCATACGCGGCAGGACCAAGCAACATG
GTCAGTTTTCTCTTGCAGTCGTCAGCCTGAACATAACATCCTTGGGATTACGCTCCCTCAAGGAGATAAGTGATGGAGATGTGATAATTTCAGGAAACAA
AAATTTGTGCTATGCAAATACAATAAACTGGAAAAAACTGTTTGGGACCTCCGGTCAGAAAACCAAAATTATAAGCAACAGAGGTGAAAACAGCTGCAAG
GCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGG
AATGCGTGGACAAGTGCAAGCTTCTGGAGGGTGAGCCAAGGGAGTTTGTGGAGAACTCTGAGTGCATACAGTGCCACCCAGAGTGCCTGCCTCAGGCCAT
GAACATCACCTGCACAGGACGGGGACCAGACAACTGTATCCAGTGTGCCCACTACATTGACGGCCCCCACTGCGTCAAGACCTGCCCGGCAGGAGTCATG
GGAGAAAACAACACCCTGGTCTGGAAGTACGCAGACGCCGGCCATGTGTGCCACCTGTGCCATCCAAACTGCACCTACGGATGCACTGGGCCAGGTCTTG
AAGGCTGTCCAACGAATGGGCCTAAGATCCCGTCCATCGCCACTGGGATGGTGGGGGCCCTCCTCTTGCTGCTGGTGGTGGCCCTGGGGATCGGCCTCTT
CATGCGAAGGCGCCACATCGTTCGGAAGCGCACGCTGCGGAGGCTGCTGCAGGAGAGGGAGCTTGTGGAGCCTCTTACACCCAGTGGAGAAGCTCCCAAC
CAAGCTCTCTTGAGGATCTTGAAGGAAACTGAATTCAAAAAGATCAAAGTGCTGGGCTCCGGTGCGTTCGGCACGGTGTATAAGGGACTCTGGATCCCAG
AAGGTGAGAAAGTTAAAATTCCCGTCGCTATCAAGGAATTAAGAGAAGCAACATCTCCGAAAGCCAACAAGGAAATCCTCGATGAAGCCTACGTGATGGC
CAGCGTGGACAACCCCCACGTGTGCCGCCTGCTGGGCATCTGCCTCACCTCCACCGTGCAACTCATCACGCAGCTCATGCCCTTCGGCTGCCTCCTGGAC
TATGTCCGGGAACACAAAGACAATATTGGCTCCCAGTACCTGCTCAACTGGTGTGTGCAGATCGCAAAGGGCATGAACTACTTGGAGGACCGTCGCTTGG
TGCACCGCGACCTGGCAGCCAGGAACGTACTGGTGAAAACACCGCAGCATGTCAAGATCACAGATTTTGGGCTGGCCAAACTGCTGGGTGCGGAAGAGAA
AGAATACCATGCAGAAGGAGGCAAAGTGCCTATCAAGTGGATGGCATTGGAATCAATTTTACACAGAATCTATACCCACCAGAGTGATGTCTGGAGCTAC
GGGGTGACCGTTTGGGAGTTGATGACCTTTGGATCCAAGCCATATGACGGAATCCCTGCCAGCGAGATCTCCTCCATCCTGGAGAAAGGAGAACGCCTCC
CTCAGCCACCCATATGTACCATCGATGTCTACATGATCATGGCCAAGTGCTGGATGATAGACGCAGATAGTCGCCCAAAGTTCCGTGAGTTGATCATCGA
ATTCTCCAAAATGGCCCGAGACCCCCAGCGCTACCTTGTCATTCAGGGGGATGAAAGAATGCATTTGCCAAGTCCTACAGACTCCAACTTCTACCGTGCC
CTGATGGATGAAGAAGACATGGACGACGTGGTGGATGCCGACGAGTACCTCATCCCACAGCAGGGCTTCTTCAGCAGCCCCTCCACGTCACGGACTCCCC
TCCTGAGCTCTCTGAGTGCAACCAGCAACAATTCCACCGTGGCTTGCATTGATAGAAATGGGCTGCAAAGCTGTCCCATCAAGGAAGACAGCTTCTTGCA
GCGATACAGCTCAGACCCCACAGGCGCCTTGACTGAGGACAGCATAGACGACACCTTCCTCCCAGTGCCTGAATACATAAACCAGTCCGTTCCCAAAAGG
CCCGCTGGCTCTGTGCAGAATCCTGTCTATCACAATCAGCCTCTGAACCCCGCGCCCAGCAGAGACCCACACTACCAGGACCCCCACAGCACTGCAGTGG
GCAACCCCGAGTATCTCAACACTGTCCAGCCCACCTGTGTCAACAGCACATTCGACAGCCCTGCCCACTGGGCCCAGAAAGGCAGCCACCAAATTAGCCT
GGACAACCCTGACTACCAGCAGGACTTCTTTCCCAAGGAAGCCAAGCCAAATGGCATCTTTAAGGGCTCCACAGCTGAAAATGCAGAATACCTAAGGGTC
GCGCCACAAAGCAGTGAATTTATTGGAGCATGA

FIGURE 6Z

(SEQ ID NO: 13) EGFR(V948A) amino acid

MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCKLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
GVTVWELMTFGSKPYDGIPASEISSILEKGERLPQPPICTIDVYMIMAKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA

FIGURE 7A

(SEQ ID NO: 58) Wild-type PI3K cDNA

ATGCCTCCAAGACCATCATCAGGTGAACTGTGGGGCATCCACTTGATGCCCCCAAGAATCCTAGTAGAATGTTTACTACCAAATGGAATGATAGTGACTT
TAGAATGCCTCCGTGAGGCTACATTAATAACCATAAAGCATGAACTATTTAAAGAAGCAAGAAAATACCCCCTCCATCAACTTCTTCAAGATGAATCTTC
TTACATTTTCGTAAGTGTTACCCAAGAAGCAGAAAGGGAAGAATTTTTTGATGAAACAAGACGACTTTGTGACCTTCGGCTTTTTCAACCCTTTTTAAAA
GTAATTGAACCAGTAGGCAACCGTGAAGAAAAGATCCTCAATCGAGAAATTGGTTTTGCTATCGGCATGCCAGTGTGTGAATTTGATATGGTTAAAGATC
CAGAAGTACAGGACTTCCGAAGAAATATTCTGAACGTTTGTAAAGAAGCTGTGGATCTTAGGGACCTCAATTCACCTCATAGTAGAGCAATGTATGTCTA
TCCTCCAAATGTAGAATCTTCACCAGAATTGCCAAAGCACATATATAATAAATTAGATAAAGGGCAAATAATAGTGGTGATCTGGGTAATAGTTTCTCCA
AATAATGACAAGCAGAAGTATACTCTGAAAATCAACCATGACTGTGTACCAGAACAAGTAATTGCTGAAGCAATCAGGAAAAAAACTCGAAGTATGTTGC
TATCCTCTGAACAACTAAAACTCTGTGTTTTAGAATATCAGGGCAAGTATATTTTAAAAGTGTGTGGATGTGATGAATACTTCCTAGAAAAATATCCTCT
GAGTCAGTATAAGTATATAAGAAGCTGTATAATGCTTGGGAGGATGCCCAATTTGATGTTGATGGCTAAAGAAAGCCTCTATTCTCAACTGCCAATGGAC
TGTTTTACAATGCCATCTTATTCCAGACGCATTTCCACAGCTACACCATATATGAATGGAGAAACATCTACAAAATCCCTTTGGGTTATAAATAGTGCAC
TCAGAATAAAAATTCTTTGTGCAACCTACGTGAATGTAAATATTCGAGACATTGATAAGATCTATGTTCGAACAGGTATCTACCATGGAGGAGAACCCTT
ATGTGACAATGTGAACACTCAAAGAGTACCTTGTTCCAATCCCAGGTGGAATGAATGGCTGAATTATGATATATACATTCCTGATCTTCCTCGTGCTGCT
CGACTTTGCCTTTCCATTTGCTCTGTTAAAGGCCGAAAGGGTGCTAAAGAGGAACACTGTCCATTGGCATGGGGAAATATAAACTTGTTTGATTACACAG
ACACTCTAGTATCTGGAAAAATGGCTTTGAATCTTTGGCCAGTACCTCATGGACTAGAAGATTTGCTGAACCCTATTGGTGTTACTGGATCAAATCCAAA
TAAAGAAACTCCATGCTTAGAGTTGGAGTTTGACTGGTTCAGCAGTGTGGTAAAGTTCCCAGATATGTCAGTGATTGAAGAGCATGCCAATTGGTCTGTA
TCCCGAGAAGCAGGATTTAGCTATTCCCACGCAGGACTGAGTAACAGACTAGCTAGAGACAATGAATTAAGGGAAAATGACAAAGAACAGCTCAAAGCAA
TTTCTACACGAGATCCTCTCTCTGAAATCACTGAGCAGGAGAAAGATTTTCTATGGAGTCACAGACACTATTGTGTAACTATCCCCGAAATTCTACCCAA
ATTGCTTCTGTCTGTTAAATGGAATTCTAGAGATGAAGTAGCCCAGATGTATTGCTTGGTAAAAGATTGGCCTCCAATCAAACCTGAACAGGCTATGGAA
CTTCTGGACTGTAATTACCCAGATCCTATGGTTCGAGGTTTTGCTGTTCGGTGCTTGGAAAAATATTTAACAGATGACAAACTTTCTCAGTATTTAATTC
AGCTAGTACAGGTCCTAAAATATGAACAATATTTGGATAACTTGCTTGTGAGATTTTTACTGAAGAAAGCATTGACTAATCAAAGGATTGGGCACTTTTT
CTTTTGGCATTTAAAATCTGAGATGCACAATAAAACAGTTAGCCAGAGGTTTGGCCTGCTTTTGGAGTCCTATTGTCGTGCATGTGGGATGTATTTGAAG
CACCTGAATAGGCAAGTCGAGGCAATGGAAAAGCTCATTAACTTAACTGACATTCTCAAACAGGAGAAGAAGGATGAAACACAAAAGGTACAGATGAAGT
TTTTAGTTGAGCAAATGAGGCGACCAGATTTCATGGATGCTCTACAGGGCTTTCTGTCTCCTCTAAACCCTGCTCATCAACTAGGAAACCTCAGGCTTGA
AGAGTGTCGAATTATGTCCTCTGCAAAAAGGCCACTGTGGTTGAATTGGGAGAACCCAGACATCATGTCAGAGTTACTGTTTCAGAACAATGAGATCATC
TTTAAAAATGGGGATGATTTACGGCAAGATATGCTAACACTTCAAATTATTCGTATTATGGAAAATATCTGGCAAAATCAAGGTCTTGATCTTCGAATGT
TACCTTATGGTTGTCTGTCAATCGGTGACTGTGTGGGACTTATTGAGGTGGTGCGAAATTCTCACACTATTATGCAAATTCAGTGCAAAGGCGGCTTGAA
AGGTGCACTGCAGTTCAACAGCCACACACTACATCAGTGGCTCAAAGACAAGAACAAAGGAGAAATATATGATGCAGCCATTGACCTGTTTACACGTTCA
TGTGCTGGATACTGTGTAGCTACCTTCATTTTGGGAATTGGAGATCGTCACAATAGTAACATCATGGTGAAAGACGATGGACAGCTGTTTCATATAGATT
TTGGACACTTTTTGGATCACAAGAAGAAAAAATTTGGTTATAAACGAGAACGTGTGCCATTTGTTTTGACACAGGATTTCTTAATAGTGATTAGTAAAGG
AGCCCAAGAATGCACAAAGACAAGAGAATTTGAGAGGTTTCAGGAGATGTGTTACAAGGCTTATCTAGCTATTCGACAGCATGCCAATCTCTTCATAAAT
CTTTTCTCAATGATGCTTGGCTCTGGAATGCCAGAACTACAATCTTTTGATGACATTGCATACATTCGAAAGACCCTAGCCTTAGATAAAACTGAGCAAG
AGGCTTTGGAGTATTTCATGAAACAAATGAATGATGCACATCATGGTGGCTGGACAACAAAAATGGATTGGATCTTCCACACAATTAAACAGCATGCATT
GAACTGA

FIGURE 7B

(SEQ ID NO: 14) Wild-type PI3K amino acid

MPPRPSSGELWGIHLMPPRILVECLLPNGMIVTLECLREATLITIKHELF
KEARKYPLHQLLQDESSYIFVSVTQEAEREEFFDETRRLCDLRLFQPFLK
VIEPVGNREEKILNREIGFAIGMPVCEFDMVKDPEVQDFRRNILNVCKEA
VDLRDLNSPHSRAMYVYPPNVESSPELPKHIYNKLDKGQIIVVIWVIVSP
NNDKQKYTLKINHDCVPEQVIAEAIRKKTRSMLLSSEQLKLCVLEYQGKY
ILKVCGCDEYFLEKYPLSQYKYIRSCIMLGRMPNLMLMAKESLYSQLPMD
CFTMPSYSRRISTATPYMNGETSTKSLWVINSALRIKILCATYVNVNIRD
IDKIYVRTGIYHGGEPLCDNVNTQRVPCSNPRWNEWLNYDIYIPDLPRAA
RLCLSICSVKGRKGAKEEHCPLAWGNINLFDYTDTLVSGKMALNLWPVPH
GLEDLLNPIGVTGSNPNKETPCLELEFDWFSSVVKFPDMSVIEEHANWSV
SREAGFSYSHAGLSNRLARDNELRENDKEQLKAISTRDPLSEITEQEKDF
LWSHRHYCVTIPEILPKLLLSVKWNSRDEVAQMYCLVKDWPPIKPEQAME
LLDCNYPDPMVRGFAVRCLEKYLTDDKLSQYLIQLVQVLKYEQYLDNLLV
RFLLKKALTNQRIGHFFFWHLKSEMHNKTVSQRFGLLLESYCRACGMYLK
HLNRQVEAMEKLINLTDILKQEKKDETQKVQMKFLVEQMRRPDFMDALQG
FLSPLNPAHQLGNLRLEECRIMSSAKRPLWLNWENPDIMSELLFQNNEII
FKNGDDLRQDMLTLQIIRIMENIWQNQGLDLRMLPYGCLSIGDCVGLIEV
VRNSHTIMQIQCKGGLKGALQFNSHTLHQWLKDKNKGEIYDAAIDLFTRS
CAGYCVATFILGIGDRHNSNIMVKDDGQLFHIDFGHFLDHKKKKFGYKRE
RVPFVLTQDFLIVISKGAQECTKTREFERFQEMCYKAYLAIRQHANLFIN
LFSMMLGSGMPELQSFDDIAYIRKTLALDKTEQEALEYFMKQMNDAHHGG
WTTKMDWIFHTIKQHALN

FIGURE 7C

(SEQ ID NO: 53) PI3K (E542K) cDNA

ATGCCTCCAAGACCATCATCAGGTGAACTGTGGGGCATCCACTTGATGCCCCCAAGAATCCTAGTAGAATGTTTACTACCAAATGGAATGATAGTGACTT
TAGAATGCCTCCGTGAGGCTACATTAATAACCATAAAGCATGAACTATTTAAAGAAGCAAGAAAATACCCCCTCCATCAACTTCTTCAAGATGAATCTTC
TTACATTTTCGTAAGTGTTACCCAAGAAGCAGAAAGGGAAGAATTTTTTGATGAAACAAGACGACTTTGTGACCTTCGGCTTTTTCAACCCTTTTTAAAA
GTAATTGAACCAGTAGGCAACCGTGAAGAAAAGATCCTCAATCGAGAAATTGGTTTTGCTATCGGCATGCCAGTGTGTGAATTTGATATGGTTAAAGATC
CAGAAGTACAGGACTTCCGAAGAAATATTCTGAACGTTTGTAAAGAAGCTGTGGATCTTAGGGACCTCAATTCACCTCATAGTAGAGCAATGTATGTCTA
TCCTCCAAATGTAGAATCTTCACCAGAATTGCCAAAGCACATATATAATAAATTAGATAAAGGGCAAATAATAGTGGTGATCTGGGTAATAGTTTCTCCA
AATAATGACAAGCAGAAGTATACTCTGAAAATCAACCATGACTGTGTACCAGAACAAGTAATTGCTGAAGCAATCAGGAAAAAAACTCGAAGTATGTTGC
TATCCTCTGAACAACTAAAACTCTGTGTTTTAGAATATCAGGGCAAGTATATTTTAAAAGTGTGTGGATGTGATGAATACTTCCTAGAAAAATATCCTCT
GAGTCAGTATAAGTATATAAGAAGCTGTATAATGCTTGGGAGGATGCCCAATTTGATGTTGATGGCTAAAGAAAGCCTCTATTCTCAACTGCCAATGGAC
TGTTTTACAATGCCATCTTATTCCAGACGCATTTCCACAGCTACACCATATATGAATGGAGAAACATCTACAAAATCCCTTTGGGTTATAAATAGTGCAC
TCAGAATAAAAATTCTTTGTGCAACCTACGTGAATGTAAATATTCGAGACATTGATAAGATCTATGTTCGAACAGGTATCTACCATGGAGGAGAACCCTT
ATGTGACAATGTGAACACTCAAAGAGTACCTTGTTCCAATCCCAGGTGGAATGAATGGCTGAATTATGATATATACATTCCTGATCTTCCTCGTGCTGCT
CGACTTTGCCTTTCCATTTGCTCTGTTAAAGGCCGAAAGGGTGCTAAAGAGGAACACTGTCCATTGGCATGGGGAAATATAAACTTGTTTGATTACACAG
ACACTCTAGTATCTGGAAAAATGGCTTTGAATCTTTGGCCAGTACCTCATGGACTAGAAGATTTGCTGAACCCTATTGGTGTTACTGGATCAAATCCAAA
TAAAGAAACTCCATGCTTAGAGTTGGAGTTTGACTGGTTCAGCAGTGTGGTAAAGTTCCCAGATATGTCAGTGATTGAAGAGCATGCCAATTGGTCTGTA
TCCCGAGAAGCAGGATTTAGCTATTCCCACGCAGGACTGAGTAACAGACTAGCTAGAGACAATGAATTAAGGGAAAATGACAAAGAACAGCTCAAAGCAA
TTTCTACACGAGATCCTCTCTCTAAAATCACTGAGCAGGAGAAAGATTTTCTATGGAGTCACAGACACTATTGTGTAACTATCCCCGAAATTCTACCCAA
ATTGCTTCTGTCTGTTAAATGGAATTCTAGAGATGAAGTAGCCCAGATGTATTGCTTGGTAAAAGATTGGCCTCCAATCAAACCTGAACAGGCTATGGAA
CTTCTGGACTGTAATTACCCAGATCCTATGGTTCGAGGTTTTGCTGTTCGGTGCTTGGAAAAATATTTAACAGATGACAAACTTTCTCAGTATTTAATTC
AGCTAGTACAGGTCCTAAAATATGAACAATATTTGGATAACTTGCTTGTGAGATTTTTACTGAAGAAAGCATTGACTAATCAAAGGATTGGGCACTTTTT
CTTTTGGCATTTAAAATCTGAGATGCACAATAAAACAGTTAGCCAGAGGTTTGGCCTGCTTTTGGAGTCCTATTGTCGTGCATGTGGGATGTATTTGAAG
CACCTGAATAGGCAAGTCGAGGCAATGGAAAAGCTCATTAACTTAACTGACATTCTCAAACAGGAGAAGAAGGATGAAACACAAAAGGTACAGATGAAGT
TTTTAGTTGAGCAAATGAGGCGACCAGATTTCATGGATGCTCTACAGGGCTTTCTGTCTCCTCTAAACCCTGCTCATCAACTAGGAAACCTCAGGCTTGA
AGAGTGTCGAATTATGTCCTCTGCAAAAAGGCCACTGTGGTTGAATTGGGAGAACCCAGACATCATGTCAGAGTTACTGTTTCAGAACAATGAGATCATC
TTTAAAAATGGGGATGATTTACGGCAAGATATGCTAACACTTCAAATTATTCGTATTATGGAAAATATCTGGCAAAATCAAGGTCTTGATCTTCGAATGT
TACCTTATGGTTGTCTGTCAATCGGTGACTGTGTGGGACTTATTGAGGTGGTGCGAAATTCTCACACTATTATGCAAATTCAGTGCAAAGGCGGCTTGAA
AGGTGCACTGCAGTTCAACAGCCACACACTACATCAGTGGCTCAAAGACAAGAACAAAGGAGAAATATATGATGCAGCCATTGACCTGTTTACACGTTCA
TGTGCTGGATACTGTGTAGCTACCTTCATTTTGGGAATTGGAGATCGTCACAATAGTAACATCATGGTGAAAGACGATGGACAGCTGTTTCATATAGATT
TTGGACACTTTTTGGATCACAAGAAGAAAAAATTTGGTTATAAACGAGAACGTGTGCCATTTGTTTTGACACAGGATTTCTTAATAGTGATTAGTAAAGG
AGCCCAAGAATGCACAAAGACAAGAGAATTTGAGAGGTTTCAGGAGATGTGTTACAAGGCTTATCTAGCTATTCGACAGCATGCCAATCTCTTCATAAAT
CTTTTCTCAATGATGCTTGGCTCTGGAATGCCAGAACTACAATCTTTTGATGACATTGCATACATTCGAAAGACCCTAGCCTTAGATAAAACTGAGCAAG
AGGCTTTGGAGTATTTCATGAAACAAATGAATGATGCACATCATGGTGGCTGGACAACAAAAATGGATTGGATCTTCCACACAATTAAACAGCATGCATT
GAACTGA

FIGURE 7D

(SEQ ID NO: 15) PI3K (E542K) amino acid

MPPRPSSGELWGIHLMPPRILVECLLPNGMIVTLECLREATLITIKHELF
KEARKYPLHQLLQDESSYIFVSVTQEAEREEFFDETRRLCDLRLFQPFLK
VIEPVGNREEKILNREIGFAIGMPVCEFDMVKDPEVQDFRRNILNVCKEA
VDLRDLNSPHSRAMYVYPPNVESSPELPKHIYNKLDKGQIIVVIWVIVSP
NNDKQKYTLKINHDCVPEQVIAEAIRKKTRSMLLSSEQLKLCVLEYQGKY
ILKVCGCDEYFLEKYPLSQYKYIRSCIMLGRMPNLMLMAKESLYSQLPMD
CFTMPSYSRRISTATPYMNGETSTKSLWVINSALRIKILCATYVNVNIRD
IDKIYVRTGIYHGGEPLCDNVNTQRVPCSNPRWNEWLNYDIYIPDLPRAA
RLCLSICSVKGRKGAKEEHCPLAWGNINLFDYTDTLVSGKMALNLWPVPH
GLEDLLNPIGVTGSNPNKETPCLELEFDWFSSVVKFPDMSVIEEHANWSV
SREAGFSYSHAGLSNRLARDNELRENDKEQLKAISTRDPLSKITEQEKDF
LWSHRHYCVTIPEILPKLLLSVKWNSRDEVAQMYCLVKDWPPIKPEQAME
LLDCNYPDPMVRGFAVRCLEKYLTDDKLSQYLIQLVQVLKYEQYLDNLLV
RFLLKKALTNQRIGHFFFWHLKSEMHNKTVSQRFGLLLESYCRACGMYLK
HLNRQVEAMEKLINLTDILKQEKKDETQKVQMKFLVEQMRRPDFMDALQG
FLSPLNPAHQLGNLRLEECRIMSSAKRPLWLNWENPDIMSELLFQNNEII
FKNGDDLRQDMLTLQIIRIMENIWQNQGLDLRMLPYGCLSIGDCVGLIEV
VRNSHTIMQIQCKGGLKGALQFNSHTLHQWLKDKNKGEIYDAAIDLFTRS
CAGYCVATFILGIGDRHNSNIMVKDDGQLFHIDFGHFLDHKKKKFGYKRE
RVPFVLTQDFLIVISKGAQECTKTREFERFQEMCYKAYLAIRQHANLFIN
LFSMMLGSGMPELQSFDDIAYIRKTLALDKTEQEALEYFMKQMNDAHHGG
WTTKMDWIFHTIKQHALN

FIGURE 7E

(SEQ ID NO: 50) PI3K (E545A) cDNA

ATGCCTCCAAGACCATCATCAGGTGAACTGTGGGGCATCCACTTGATGCCCCCAAGAATCCTAGTAGAATGTTTACTACCAAATGGAATGATAGTGACTT
TAGAATGCCTCCGTGAGGCTACATTAATAACCATAAAGCATGAACTATTTAAAGAAGCAAGAAAATACCCCCTCCATCAACTTCTTCAAGATGAATCTTC
TTACATTTTCGTAAGTGTTACCCAAGAAGCAGAAAGGGAAGAATTTTTTGATGAAACAAGACGACTTTGTGACCTTCGGCTTTTTCAACCCTTTTTAAAA
GTAATTGAACCAGTAGGCAACCGTGAAGAAAAGATCCTCAATCGAGAAATTGGTTTTGCTATCGGCATGCCAGTGTGTGAATTTGATATGGTTAAAGATC
CAGAAGTACAGGACTTCCGAAGAAATATTCTGAACGTTTGTAAAGAAGCTGTGGATCTTAGGGACCTCAATTCACCTCATAGTAGAGCAATGTATGTCTA
TCCTCCAAATGTAGAATCTTCACCAGAATTGCCAAAGCACATATATAATAAATTAGATAAAGGGCAAATAATAGTGGTGATCTGGGTAATAGTTTCTCCA
AATAATGACAAGCAGAAGTATACTCTGAAAATCAACCATGACTGTGTACCAGAACAAGTAATTGCTGAAGCAATCAGGAAAAAAACTCGAAGTATGTTGC
TATCCTCTGAACAACTAAAACTCTGTGTTTTAGAATATCAGGGCAAGTATATTTTAAAAGTGTGTGGATGTGATGAATACTTCCTAGAAAAATATCCTCT
GAGTCAGTATAAGTATATAAGAAGCTGTATAATGCTTGGGAGGATGCCCAATTTGATGTTGATGGCTAAAGAAAGCCTCTATTCTCAACTGCCAATGGAC
TGTTTTACAATGCCATCTTATTCCAGACGCATTTCCACAGCTACACCATATATGAATGGAGAAACATCTACAAAATCCCTTTGGGTTATAAATAGTGCAC
TCAGAATAAAAATTCTTTGTGCAACCTACGTGAATGTAAATATTCGAGACATTGATAAGATCTATGTTCGAACAGGTATCTACCATGGAGGAGAACCCTT
ATGTGACAATGTGAACACTCAAAGAGTACCTTGTTCCAATCCCAGGTGGAATGAATGGCTGAATTATGATATATACATTCCTGATCTTCCTCGTGCTGCT
CGACTTTGCCTTTCCATTTGCTCTGTTAAAGGCCGAAAGGGTGCTAAAGAGGAACACTGTCCATTGGCATGGGGAAATATAAACTTGTTTGATTACACAG
ACACTCTAGTATCTGGAAAAATGGCTTTGAATCTTTGGCCAGTACCTCATGGACTAGAAGATTTGCTGAACCCTATTGGTGTTACTGGATCAAATCCAAA
TAAAGAAACTCCATGCTTAGAGTTGGAGTTTGACTGGTTCAGCAGTGTGGTAAAGTTCCCAGATATGTCAGTGATTGAAGAGCATGCCAATTGGTCTGTA
TCCCGAGAAGCAGGATTTAGCTATTCCCACGCAGGACTGAGTAACAGACTAGCTAGAGACAATGAATTAAGGGAAAATGACAAAGAACAGCTCAAAGCAA
TTTCTACACGAGATCCTCTCTCTGAAATCACTGCGCAGGAGAAAGATTTTCTATGGACCACAGGTAAACACTATTGTGTAACTATCCCCGAAATTCTACC
CAAATTGCTTCTGTCTGTTAAATGGAATTCTAGAGATGAAGTAGCCCAGATGTATTGCTTGGTAAAAGATTGGCCTCCAATCAAACCTGAACAGGCTATG
GAACTTCTGGACTGTAATTACCCAGATCCTATGGTTCGAGGTTTTGCTGTTCGGTGCTTGGAAAAATATTTAACAGATGACAAACTTTCTCAGTATTTAA
TTCAGCTAGTACAGGTCCTAAAATATGAACAATATTTGGATAACTTGCTTGTGAGATTTTTACTGAAGAAAGCATTGACTAATCAAAGGATTGGGCACTT
TTTCTTTTGGCATTTAAAATCTGAGATGCACAATAAAACAGTTAGCCAGAGGTTTGGCCTGCTTTTGGAGTCCTATTGTCGTGCATGTGGGATGTATTTG
AAGCACCTGAATAGGCAAGTCGAGGCAATGGAAAAGCTCATTAACTTAACTGACATTCTCAAACAGGAGAAGAAGGATGAAACACAAAAGGTACAGATGA
AGTTTTTAGTTGAGCAAATGAGGCGACCAGATTTCATGGATGCTCTACAGGGCTTTCTGTCTCCTCTAAACCCTGCTCATCAACTAGGAAACCTCAGGCT
TGAAGAGTGTCGAATTATGTCCTCTGCAAAAAGGCCACTGTGGTTGAATTGGGAGAACCCAGACATCATGTCAGAGTTACTGTTTCAGAACAATGAGATC
ATCTTTAAAAATGGGGATGATTTACGGCAAGATATGCTAACACTTCAAATTATTCGTATTATGGAAAATATCTGGCAAAATCAAGGTCTTGATCTTCGAA
TGTTACCTTATGGTTGTCTGTCAATCGGTGACTGTGTGGGACTTATTGAGGTGGTGCGAAATTCTCACACTATTATGCAAATTCAGTGCAAAGGCGGCTT
GAAAGGTGCACTGCAGTTCAACAGCCACACACTACATCAGTGGCTCAAAGACAAGAACAAAGGAGAAATATATGATGCAGCCATTGACCTGTTTACACGT
TCATGTGCTGGATACTGTGTAGCTACCTTCATTTTGGGAATTGGAGATCGTCACAATAGTAACATCATGGTGAAAGACGATGGACAGCTGTTTCATATAG
ATTTTGGACACTTTTTGGATCACAAGAAGAAAAAATTTGGTTATAAACGAGAACGTGTGCCATTTGTTTTGACACAGGATTTCTTAATAGTGATTAGTAA
AGGAGCCCAAGAATGCACAAAGACAAGAGAATTTGAGAGGTTTCAGGAGATGTGTTACAAGGCTTATCTAGCTATTCGACAGCATGCCAATCTCTTCATA
AATCTTTTCTCAATGATGCTTGGCTCTGGAATGCCAGAACTACAATCTTTTGATGACATTGCATACATTCGAAAGACCCTAGCCTTAGATAAAACTGAGC
AAGAGGCTTTGGAGTATTTCATGAAACAAATGAATGATGCACATCATGGTGGCTGGACAACAAAAATGGATTGGATCTTCCACACAATTAAACAGCATGC
ATTGAACTGA

FIGURE 7F

(SEQ ID NO: 16) PI3K (E545A) amino acid

```
MPPRPSSGELWGIHLMPPRILVECLLPNGMIVTLECLREATLITIKHELF
KEARKYPLHQLLQDESSYIFVSVTQEAEREEFFDETRRLCDLRLFQPFLK
VIEPVGNREEKILNREIGFAIGMPVCEFDMVKDPEVQDFRRNILNVCKEA
VDLRDLNSPHSRAMYVYPPNVESSPELPKHIYNKLDKGQIIVVIWVIVSP
NNDKQKYTLKINHDCVPEQVIAEAIRKKTRSMLLSSEQLKLCVLEYQGKY
ILKVCGCDEYFLEKYPLSQYKYIRSCIMLGRMPNLMLMAKESLYSQLPMD
CFTMPSYSRRISTATPYMNGETSTKSLWVINSALRIKILCATYVNVNIRD
IDKIYVRTGIYHGGEPLCDNVNTQRVPCSNPRWNEWLNYDIYIPDLPRAA
RLCLSICSVKGRKGAKEEHCPLAWGNINLFDYTDTLVSGKMALNLWPVPH
GLEDLLNPIGVTGSNPNKETPCLELEFDWFSSVVKFPDMSVIEEHANWSV
SREAGFSYSHAGLSNRLARDNELRENDKEQLKAISTRDPLSEITAQEKDF
LWTTGKHYCVTIPEILPKLLLSVKWNSRDEVAQMYCLVKDWPPIKPEQAM
ELLDCNYPDPMVRGFAVRCLEKYLTDDKLSQYLIQLVQVLKYEQYLDNLL
VRFLLKKALTNQRIGHFFFWHLKSEMHNKTVSQRFGLLLESYCRACGMYL
KHLNRQVEAMEKLINLTDILKQEKKDETQKVQMKFLVEQMRRPDFMDALQ
GFLSPLNPAHQLGNLRLEECRIMSSAKRPLWLNWENPDIMSELLFQNNEI
IFKNGDDLRQDMLTLQIIRIMENIWQNQGLDLRMLPYGCLSIGDCVGLIE
VVRNSHTIMQIQCKGGLKGALQFNSHTLHQWLKDKNKGEIYDAAIDLFTR
SCAGYCVATFILGIGDRHNSNIMVKDDGQLFHIDFGHFLDHKKKKFGYKR
ERVPFVLTQDFLIVISKGAQECTKTREFERFQEMCYKAYLAIRQHANLFI
NLFSMMLGSGMPELQSFDDIAYIRKTLALDKTEQEALEYFMKQMNDAHHG
GWTTKMDWIFHTIKQHALN
```

FIGURE 7G (SEQ ID NO: 54) PI3K (H1047L) cDNA

ATGCCTCCAAGACCATCATCAGGTGAACTGTGGGGCATCCACTTGATGCCCCCAAGAATCCTAGTAGAATGTTTACTACCAAATGGAATGATAGTGACTT
TAGAATGCCTCCGTGAGGCTACATTAATAACCATAAAGCATGAACTATTTAAAGAAGCAAGAAAATACCCCCTCCATCAACTTCTTCAAGATGAATCTTC
TTACATTTTCGTAAGTGTTACCCAAGAAGCAGAAAGGGAAGAATTTTTTGATGAAACAAGACGACTTTGTGACCTTCGGCTTTTTCAACCCTTTTTAAAA
GTAATTGAACCAGTAGGCAACCGTGAAGAAAAGATCCTCAATCGAGAAATTGGTTTTGCTATCGGCATGCCAGTGTGTGAATTTGATATGGTTAAAGATC
CAGAAGTACAGGACTTCCGAAGAAATATTCTGAACGTTTGTAAAGAAGCTGTGGATCTTAGGGACCTCAATTCACCTCATAGTAGAGCAATGTATGTCTA
TCCTCCAAATGTAGAATCTTCACCAGAATTGCCAAAGCACATATATAATAAATTAGATAAAGGGCAAATAATAGTGGTGATCTGGGTAATAGTTTCTCCA
AATAATGACAAGCAGAAGTATACTCTGAAAATCAACCATGACTGTGTACCAGAACAAGTAATTGCTGAAGCAATCAGGAAAAAAACTCGAAGTATGTTGC
TATCCTCTGAACAACTAAAACTCTGTGTTTTAGAATATCAGGGCAAGTATATTTTAAAAGTGTGTGGATGTGATGAATACTTCCTAGAAAAATATCCTCT
GAGTCAGTATAAGTATATAAGAAGCTGTATAATGCTTGGGAGGATGCCCAATTTGATGTTGATGGCTAAAGAAAGCCTCTATTCTCAACTGCCAATGGAC
TGTTTTACAATGCCATCTTATTCCAGACGCATTTCCACAGCTACACCATATATGAATGGAGAAACATCTACAAAATCCCTTTGGGTTATAAATAGTGCAC
TCAGAATAAAAATTCTTTGTGCAACCTACGTGAATGTAAATATTCGAGACATTGATAAGATCTATGTTCGAACAGGTATCTACCATGGAGGAGAACCCTT
ATGTGACAATGTGAACACTCAAAGAGTACCTTGTTCCAATCCCAGGTGGAATGAATGGCTGAATTATGATATATACATTCCTGATCTTCCTCGTGCTGCT
CGACTTTGCCTTTCCATTTGCTCTGTTAAAGGCCGAAAGGGTGCTAAAGAGGAACACTGTCCATTGGCATGGGGAAATATAAACTTGTTTGATTACACAG
ACACTCTAGTATCTGGAAAAATGGCTTTGAATCTTTGGCCAGTACCTCATGGACTAGAAGATTTGCTGAACCCTATTGGTGTTACTGGATCAAATCCAAA
TAAAGAAACTCCATGCTTAGAGTTGGAGTTTGACTGGTTCAGCAGTGTGGTAAAGTTCCCAGATATGTCAGTGATTGAAGAGCATGCCAATTGGTCTGTA
TCCCGAGAAGCAGGATTTAGCTATTCCCACGCAGGACTGAGTAACAGACTAGCTAGAGACAATGAATTAAGGGAAAATGACAAAGAACAGCTCAAAGCAA
TTTCTACACGAGATCCTCTCTCTGAAATCACTGAGCAGGAGAAAGATTTTCTATGGAGTCACAGACACTATTGTGTAACTATCCCCGAAATTCTACCCAA
ATTGCTTCTGTCTGTTAAATGGAATTCTAGAGATGAAGTAGCCCAGATGTATTGCTTGGTAAAAGATTGGCCTCCAATCAAACCTGAACAGGCTATGGAA
CTTCTGGACTGTAATTACCCAGATCCTATGGTTCGAGGTTTTGCTGTTCGGTGCTTGGAAAAATATTTAACAGATGACAAACTTTCTCAGTATTTAATTC
AGCTAGTACAGGTCCTAAAATATGAACAATATTTGGATAACTTGCTTGTGAGATTTTTACTGAAGAAAGCATTGACTAATCAAAGGATTGGGCACTTTTT
CTTTTGGCATTTAAAATCTGAGATGCACAATAAAACAGTTAGCCAGAGGTTTGGCCTGCTTTTGGAGTCCTATTGTCGTGCATGTGGGATGTATTTGAAG
CACCTGAATAGGCAAGTCGAGGCAATGGAAAAGCTCATTAACTTAACTGACATTCTCAAACAGGAGAAGAAGGATGAAACACAAAAGGTACAGATGAAGT
TTTTAGTTGAGCAAATGAGGCGACCAGATTTCATGGATGCTCTACAGGGCTTTCTGTCTCCTCTAAACCCTGCTCATCAACTAGGAAACCTCAGGCTTGA
AGAGTGTCGAATTATGTCCTCTGCAAAAAGGCCACTGTGGTTGAATTGGGAGAACCCAGACATCATGTCAGAGTTACTGTTTCAGAACAATGAGATCATC
TTTAAAAATGGGGATGATTTACGGCAAGATATGCTAACACTTCAAATTATTCGTATTATGGAAAATATCTGGCAAAATCAAGGTCTTGATCTTCGAATGT
TACCTTATGGTTGTCTGTCAATCGGTGACTGTGTGGGACTTATTGAGGTGGTGCGAAATTCTCACACTATTATGCAAATTCAGTGCAAAGGCGGCTTGAA
AGGTGCACTGCAGTTCAACAGCCACACACTACATCAGTGGCTCAAAGACAAGAACAAAGGAGAAATATATGATGCAGCCATTGACCTGTTTACACGTTCA
TGTGCTGGATACTGTGTAGCTACCTTCATTTTGGGAATTGGAGATCGTCACAATAGTAACATCATGGTGAAAGACGATGGACAGCTGTTTCATATAGATT
TTGGACACTTTTTGGATCACAAGAAGAAAAAATTTGGTTATAAACGAGAACGTGTGCCATTTGTTTTGACACAGGATTTCTTAATAGTGATTAGTAAAGG
AGCCCAAGAATGCACAAAGACAAGAGAATTTGAGAGGTTTCAGGAGATGTGTTACAAGGCTTATCTAGCTATTCGACAGCATGCCAATCTCTTCATAAAT
CTTTTCTCAATGATGCTTGGCTCTGGAATGCCAGAACTACAATCTTTTGATGACATTGCATACATTCGAAAGACCCTAGCCTTAGATAAAACTGAGCAAG
AGGCTTTGGAGTATTTCATGAAACAAATGAATGATGCACTTCATGGTGGCTGGACAACAAAAATGGATTGGATCTTCCACACAATTAAACAGCATGCATT
GAACTGA

FIGURE 7H

(SEQ ID NO: 17) PI3K (H1047L) amino acid

MPPRPSSGELWGIHLMPPRILVECLLPNGMIVTLECLREATLITIKHELF
KEARKYPLHQLLQDESSYIFVSVTQEAEREEFFDETRRLCDLRLFQPFLK
VIEPVGNREEKILNREIGFAIGMPVCEFDMVKDPEVQDFRRNILNVCKEA
VDLRDLNSPHSRAMYVYPPNVESSPELPKHIYNKLDKGQIIVVIWVIVSP
NNDKQKYTLKINHDCVPEQVIAEAIRKKTRSMLLSSEQLKLCVLEYQGKY
ILKVCGCDEYFLEKYPLSQYKYIRSCIMLGRMPNLMLMAKESLYSQLPMD
CFTMPSYSRRISTATPYMNGETSTKSLWVINSALRIKILCATYVNVNIRD
IDKIYVRTGIYHGGEPLCDNVNTQRVPCSNPRWNEWLNYDIYIPDLPRAA
RLCLSICSVKGRKGAKEEHCPLAWGNINLFDYTDTLVSGKMALNLWPVPH
GLEDLLNPIGVTGSNPNKETPCLELEFDWFSSVVKFPDMSVIEEHANWSV
SREAGFSYSHAGLSNRLARDNELRENDKEQLKAISTRDPLSEITEQEKDF
LWSHRHYCVTIPEILPKLLLSVKWNSRDEVAQMYCLVKDWPPIKPEQAME
LLDCNYPDPMVRGFAVRCLEKYLTDDKLSQYLIQLVQVLKYEQYLDNLLV
RFLLKKALTNQRIGHFFFWHLKSEMHNKTVSQRFGLLLESYCRACGMYLK
HLNRQVEAMEKLINLTDILKQEKKDETQKVQMKFLVEQMRRPDFMDALQG
FLSPLNPAHQLGNLRLEECRIMSSAKRPLWLNWENPDIMSELLFQNNEII
FKNGDDLRQDMLTLQIIRIMENIWQNQGLDLRMLPYGCLSIGDCVGLIEV
VRNSHTIMQIQCKGGLKGALQFNSHTLHQWLKDKNKGEIYDAAIDLFTRS
CAGYCVATFILGIGDRHNSNIMVKDDGQLFHIDFGHFLDHKKKKFGYKRE
RVPFVLTQDFLIVISKGAQECTKTREFERFQEMCYKAYLAIRQHANLFIN
LFSMMLGSGMPELQSFDDIAYIRKTLALDKTEQEALEYFMKQMNDALHGG
WTTKMDWIFHTIKQHALN

FIGURE 8A

(SEQ ID NO: 60) Wild-type b-RAF cDNA

ATGGCGGCGCTGAGCGGTGGCGGTGGTGGCGGCGCGGAGCCGGGCCAGGCTCTGTTCAACGGGGACATGGAGCCCGAGGCCGGCGCCGGCGCCGGCGCCG
CGGCCTCTTCGGCTGCGGACCCTGCCATTCCGGAGGAGGTGTGGAATATCAAACAAATGATTAAGTTGACACAGGAACATATAGAGGCCCTATTGGACAA
ATTTGGTGGGGAGCATAATCCACCATCAATATATCTGGAGGCCTATGAAGAATACACCAGCAAGCTAGATGCACTCCAACAAAGAGAACAACAGTTATTG
GAATCTCTGGGGAACGGAACTGATTTTTCTGTTTCTAGCTCTGCATCAATGGATACCGTTACATCTTCTTCCTCTTCTAGCCTTTCAGTGCTACCTTCAT
CTCTTTCAGTTTTTCAAAATCCCACAGATGTGGCACGGAGCAACCCCAAGTCACCACAAAAACCTATCGTTAGAGTCTTCCTGCCCAACAAACAGAGGAC
AGTGGTACCTGCAAGGTGTGGAGTTACAGTCCGAGACAGTCTAAAGAAAGCACTGATGATGAGAGGTCTAATCCCAGAGTGCTGTGCTGTTTACAGAATT
CAGGATGGAGAGAAGAAACCAATTGGTTGGGACACTGATATTTCCTGGCTTACTGGAGAAGAATTGCATGTGGAAGTGTTGGAGAATGTTCCACTTACAA
CACACAACTTTGTACGAAAAACGTTTTTCACCTTAGCATTTTGTGACTTTTGTCGAAAGCTGCTTTTCCAGGGTTTCCGCTGTCAAACATGTGGTTATAA
ATTTCACCAGCGTTGTAGTACAGAAGTTCCACTGATGTGTGTTAATTATGACCAACTTGATTTGCTGTTTGTCTCCAAGTTCTTTGAACACCACCCAATA
CCACAGGAAGAGGCGTCCTTAGCAGAGACTGCCCTAACATCTGGATCATCCCCTTCCGCACCCGCCTCGGACTCTATTGGGCCCCAAATTCTCACCAGTC
CGTCTCCTTCAAAATCCATTCCAATTCCACAGCCCTTCCGACCAGCAGATGAAGATCATCGAAATCAATTTGGGCAACGAGACCGATCCTCATCAGCTCC
CAATGTGCATATAAACACAATAGAACCTGTCAATATTGATGACTTGATTAGAGACCAAGGATTTCGTGGTGATGGAGGATCAACCACAGGTTTGTCTGCT
ACCCCCCCTGCCTCATTACCTGGCTCACTAACTAACGTGAAAGCCTTACAGAAATCTCCAGGACCTCAGCGAGAAAGGAAGTCATCTTCATCCTCAGAAG
ACAGGAATCGAATGAAAACACTTGGTAGACGGGACTCGAGTGATGATTGGGAGATTCCTGATGGGCAGATTACAGTGGGACAAAGAATTGGATCTGGATC
ATTTGGAACAGTCTACAAGGGAAAGTGGCATGGTGATGTGGCAGTGAAAATGTTGAATGTGACAGCACCTACACCTCAGCAGTTACAAGCCTTCAAAAAT
GAAGTAGGAGTACTCAGGAAAACACGACATGTGAATATCCTACTCTTCATGGGCTATTCCACAAAGCCACAACTGGCTATTGTTACCCAGTGGTGTGAGG
GCTCCAGCTTGTATCACCATCTCCATATCATTGAGACCAAATTTGAGATGATCAAACTTATAGATATTGCACGACAGACTGCACAGGGCATGGATTACTT
ACACGCCAAGTCAATCATCCACAGAGACCTCAAGAGTAATAATATATTTCTTCATGAAGACCTCACAGTAAAAATAGGTGATTTTGGTCTAGCTACAGTG
AAATCTCGATGGAGTGGGTCCCATCAGTTTGAACAGTTGTCTGGATCCATTTTGTGGATGGCACCAGAAGTCATCAGAATGCAAGATAAAAATCCATACA
GCTTTCAGTCAGATGTATATGCATTTGGAATTGTTCTGTATGAATTGATGACTGGACAGTTACCTTATTCAAACATCAACAACAGGGACCAGATAATTTT
TATGGTGGGACGAGGATACCTGTCTCCAGATCTCAGTAAGGTACGGAGTAACTGTCCAAAAGCCATGAAGAGATTAATGGCAGAGTGCCTCAAAAAGAAA
AGAGATGAGAGACCACTCTTTCCCCAAATTCTCGCCTCTATTGAGCTGCTGGCCCGCTCATTGCCAAAAATTCACCGCAGTGCATCAGAACCCTCCTTGA
ATCGGGCTGGTTTCCAAACAGAGGATTTTAGTCTATATGCTTGTGCTTCTCCAAAAACACCCATCCAGGCAGGGGGATATGGTGCGTTTCCTGTCCACTG
A

FIGURE 8B

(SEQ ID NO: 18) Wildtype b-RAF amino acid

MAALSGGGGGGAEPGQALFNGDMEPEAGAGAGAAASSAADPAIPEEVWNI
KQMIKLTQEHIEALLDKFGGEHNPPSIYLEAYEEYTSKLDALQQREQQLL
ESLGNGTDFSVSSSASMDTVTSSSSSSLSVLPSSLSVFQNPTDVARSNPK
SPQKPIVRVFLPNKQRTVVPARCGVTVRDSLKKALMMRGLIPECCAVYRI
QDGEKKPIGWDTDISWLTGEELHVEVLENVPLTTHNFVRKTFFTLAFCDF
CRKLLFQGFRCQTCGYKFHQRCSTEVPLMCVNYDQLDLLFVSKFFEHHPI
PQEEASLAETALTSGSSPSAPASDSIGPQILTSPSPSKSIPIPQPFRPAD
EDHRNQFGQRDRSSSAPNVHINTIEPVNIDDLIRDQGFRGDGGSTTGLSA
TPPASLPGSLTNVKALQKSPGPQRERKSSSSSEDRNRMKTLGRRDSSDDW
EIPDGQITVGQRIGSGSFGTVYKGKWHGDVAVKMLNVTAPTPQQLQAFKN
EVGVLRKTRHVNILLFMGYSTKPQLAIVTQWCEGSSLYHHLHIIETKFEM
IKLIDIARQTAQGMDYLHAKSIIHRDLKSNNIFLHEDLTVKIGDFGLATV
KSRWSGSHQFEQLSGSILWMAPEVIRMQDKNPYSFQSDVYAFGIVLYELM
TGQLPYSNINNRDQIIFMVGRGYLSPDLSKVRSNCPKAMKRLMAECLKKK
RDERPLFPQILASIELLARSLPKIHRSASEPSLNRAGFQTEDFSLYACAS
PKTPIQAGGYGAFPVH

FIGURE 8C

(SEQ ID NO: 51) b-RAF(V600E) cDNA

ATGGCGGCGCTGAGCGGTGGCGGTGGTGGCGGCGCGGAGCCGGGCCAGGCTCTGTTCAACGGGGACATGGAGCCCGAGGCCGGCGCCGGCGCCGGCGCCG
CGGCCTCTTCGGCTGCGGACCCTGCCATTCCGGAGGAGGTGTGGAATATCAAACAAATGATTAAGTTGACACAGGAACATATAGAGGCCCTATTGGACAA
ATTTGGTGGGGAGCATAATCCACCATCAATATATCTGGAGGCCTATGAAGAATACACCAGCAAGCTAGATGCACTCCAACAAAGAGAACAACAGTTATTG
GAATCTCTGGGGAACGGAACTGATTTTTCTGTTTCTAGCTCTGCATCAATGGATACCGTTACATCTTCTTCCTCTTCTAGCCTTTCAGTGCTACCTTCAT
CTCTTTCAGTTTTTCAAAATCCCACAGATGTGGCACGGAGCAACCCCAAGTCACCACAAAAACCTATCGTTAGAGTCTTCCTGCCCAACAAACAGAGGAC
AGTGGTACCTGCAAGGTGTGGAGTTACAGTCCGAGACAGTCTAAAGAAAGCACTGATGATGAGAGGTCTAATCCCAGAGTGCTGTGCTGTTTACAGAATT
CAGGATGGAGAGAAGAAACCAATTGGTTGGGACACTGATATTTCCTGGCTTACTGGAGAAGAATTGCATGTGGAAGTGTTGGAGAATGTTCCACTTACAA
CACACAACTTTGTACGAAAAACGTTTTTCACCTTAGCATTTTGTGACTTTTGTCGAAAGCTGCTTTTCCAGGGTTTCCGCTGTCAAACATGTGGTTATAA
ATTTCACCAGCGTTGTAGTACAGAAGTTCCACTGATGTGTGTTAATTATGACCAACTTGATTTGCTGTTTGTCTCCAAGTTCTTTGAACACCACCCAATA
CCACAGGAAGAGGCGTCCTTAGCAGAGACTGCCCTAACATCTGGATCATCCCCTTCCGCACCCGCCTCGGACTCTATTGGGCCCCAAATTCTCACCAGTC
CGTCTCCTTCAAAATCCATTCCAATTCCACAGCCCTTCCGACCAGCAGATGAAGATCATCGAAATCAATTTGGGCAACGAGACCGATCCTCATCAGCTCC
CAATGTGCATATAAACACAATAGAACCTGTCAATATTGATGACTTGATTAGAGACCAAGGATTTCGTGGTGATGGAGGATCAACCACAGGTTTGTCTGCT
ACCCCCCCTGCCTCATTACCTGGCTCACTAACTAACGTGAAAGCCTTACAGAAATCTCCAGGACCTCAGCGAGAAAGGAAGTCATCTTCATCCTCAGAAG
ACAGGAATCGAATGAAAACACTTGGTAGACGGGACTCGAGTGATGATTGGGAGATTCCTGATGGGCAGATTACAGTGGGACAAAGAATTGGATCTGGATC
ATTTGGAACAGTCTACAAGGGAAAGTGGCATGGTGATGTGGCAGTGAAAATGTTGAATGTGACAGCACCTACACCTCAGCAGTTACAAGCCTTCAAAAAT
GAAGTAGGAGTACTCAGGAAAACACGACATGTGAATATCCTACTCTTCATGGGCTATTCCACAAAGCCACAACTGGCTATTGTTACCCAGTGGTGTGAGG
GCTCCAGCTTGTATCACCATCTCCATATCATTGAGACCAAATTTGAGATGATCAAACTTATAGATATTGCACGACAGACTGCACAGGGCATGGATTACTT
ACACGCCAAGTCAATCATCCACAGAGACCTCAAGAGTAATAATATATTTCTTCATGAAGACCTCACAGTAAAAATAGGTGATTTTGGTCTAGCTACAGAG
AAATCTCGATGGAGTGGGTCCCATCAGTTTGAACAGTTGTCTGGATCCATTTTGTGGATGGCACCAGAAGTCATCAGAATGCAAGATAAAAATCCATACA
GCTTTCAGTCAGATGTATATGCATTTGGAATTGTTCTGTATGAATTGATGACTGGACAGTTACCTTATTCAAACATCAACAACAGGGACCAGATAATTTT
TATGGTGGGACGAGGATACCTGTCTCCAGATCTCAGTAAGGTACGGAGTAACTGTCCAAAAGCCATGAAGAGATTAATGGCAGAGTGCCTCAAAAAGAAA
AGAGATGAGAGACCACTCTTTCCCCAAATTCTCGCCTCTATTGAGCTGCTGGCCCGCTCATTGCCAAAAATTCACCGCAGTGCATCAGAACCCTCCTTGA
ATCGGGCTGGTTTCCAAACAGAGGATTTTAGTCTATATGCTTGTGCTTCTCCAAAAACACCCATCCAGGCAGGGGGATATGGTGCGTTTCCTGTCCACTG
A

FIGURE 8D

(SEQ ID NO: 19) b-RAF(V600E) amino acid

MAALSGGGGGGAEPGQALFNGDMEPEAGAGAGAAASSAADPAIPEEVWNI
KQMIKLTQEHIEALLDKFGGEHNPPSIYLEAYEEYTSKLDALQQREQQLL
ESLGNGTDFSVSSSASMDTVTSSSSSSLSVLPSSLSVFQNPTDVARSNPK
SPQKPIVRVFLPNKQRTVVPARCGVTVRDSLKKALMMRGLIPECCAVYRI
QDGEKKPIGWDTDISWLTGEELHVEVLENVPLTTHNFVRKTFFTLAFCDF
CRKLLFQGFRCQTCGYKFHQRCSTEVPLMCVNYDQLDLLFVSKFFEHHPI
PQEEASLAETALTSGSSPSAPASDSIGPQILTSPSPSKSIPIPQPFRPAD
EDHRNQFGQRDRSSSAPNVHINTIEPVNIDDLIRDQGFRGDGGSTTGLSA
TPPASLPGSLTNVKALQKSPGPQRERKSSSSSEDRNRMKTLGRRDSSDDW
EIPDGQITVGQRIGSGSFGTVYKGKWHGDVAVKMLNVTAPTPQQLQAFKN
EVGVLRKTRHVNILLFMGYSTKPQLAIVTQWCEGSSLYHHLHIIETKFEM
IKLIDIARQTAQGMDYLHAKSIIHRDLKSNNIFLHEDLTVKIGDFGLATE
KSRWSGSHQFEQLSGSILWMAPEVIRMQDKNPYSFQSDVYAFGIVLYELM
TGQLPYSNINNRDQIIFMVGRGYLSPDLSKVRSNCPKAMKRLMAECLKKK
RDERPLFPQILASIELLARSLPKIHRSASEPSLNRAGFQTEDFSLYACAS
PKTPIQAGGYGAFPVH

FIGURE 8E (SEQ ID NO: 57) b-RAF(K601E) cDNA

ATGGCGGCGCTGAGCGGTGGCGGTGGTGGCGGCGCGGAGCCGGGCCAGGCTCTGTTCAACGGGGACATGGAGCCCGAGGCCGGCGCCGGCGCCGGCGCCG
CGGCCTCTTCGGCTGCGGACCCTGCCATTCCGGAGGAGGTGTGGAATATCAAACAAATGATTAAGTTGACACAGGAACATATAGAGGCCCTATTGGACAA
ATTTGGTGGGGAGCATAATCCACCATCAATATATCTGGAGGCCTATGAAGAATACACCAGCAAGCTAGATGCACTCCAACAAAGAGAACAACAGTTATTG
GAATCTCTGGGGAACGGAACTGATTTTTCTGTTTCTAGCTCTGCATCAATGGATACCGTTACATCTTCTTCCTCTTCTAGCCTTTCAGTGCTACCTTCAT
CTCTTTCAGTTTTTCAAAATCCCACAGATGTGGCACGGAGCAACCCCAAGTCACCACAAAAACCTATCGTTAGAGTCTTCCTGCCCAACAAACAGAGGAC
AGTGGTACCTGCAAGGTGTGGAGTTACAGTCCGAGACAGTCTAAAGAAAGCACTGATGATGAGAGGTCTAATCCCAGAGTGCTGTGCTGTTTACAGAATT
CAGGATGGAGAGAAGAAACCAATTGGTTGGGACACTGATATTTCCTGGCTTACTGGAGAAGAATTGCATGTGGAAGTGTTGGAGAATGTTCCACTTACAA
CACACAACTTTGTACGAAAAACGTTTTTCACCTTAGCATTTTGTGACTTTTGTCGAAAGCTGCTTTTCCAGGGTTTCCGCTGTCAAACATGTGGTTATAA
ATTTCACCAGCGTTGTAGTACAGAAGTTCCACTGATGTGTGTTAATTATGACCAACTTGATTTGCTGTTTGTCTCCAAGTTCTTTGAACACCACCCAATA
CCACAGGAAGAGGCGTCCTTAGCAGAGACTGCCCTAACATCTGGATCATCCCCTTCCGCACCCGCCTCGGACTCTATTGGGCCCCAAATTCTCACCAGTC
CGTCTCCTTCAAAATCCATTCCAATTCCACAGCCCTTCCGACCAGCAGATGAAGATCATCGAAATCAATTTGGGCAACGAGACCGATCCTCATCAGCTCC
CAATGTGCATATAAACACAATAGAACCTGTCAATATTGATGACTTGATTAGAGACCAAGGATTTCGTGGTGATGGAGGATCAACCACAGGTTTGTCTGCT
ACCCCCCCTGCCTCATTACCTGGCTCACTAACTAACGTGAAAGCCTTACAGAAATCTCCAGGACCTCAGCGAGAAAGGAAGTCATCTTCATCCTCAGAAG
ACAGGAATCGAATGAAAACACTTGGTAGACGGGACTCGAGTGATGATTGGGAGATTCCTGATGGGCAGATTACAGTGGGACAAAGAATTGGATCTGGATC
ATTTGGAACAGTCTACAAGGGAAAGTGGCATGGTGATGTGGCAGTGAAAATGTTGAATGTGACAGCACCTACACCTCAGCAGTTACAAGCCTTCAAAAAT
GAAGTAGGAGTACTCAGGAAAACACGACATGTGAATATCCTACTCTTCATGGGCTATTCCACAAAGCCACAACTGGCTATTGTTACCCAGTGGTGTGAGG
GCTCCAGCTTGTATCACCATCTCCATATCATTGAGACCAAATTTGAGATGATCAAACTTATAGATATTGCACGACAGACTGCACAGGGCATGGATTACTT
ACACGCCAAGTCAATCATCCACAGAGACCTCAAGAGTAATAATATATTTCTTCATGAAGACCTCACAGTAAAAATAGGTGATTTTGGTCTAGCTACAGTG
GAATCTCGATGGAGTGGGTCCCATCAGTTTGAACAGTTGTCTGGATCCATTTTGTGGATGGCACCAGAAGTCATCAGAATGCAAGATAAAAATCCATACA
GCTTTCAGTCAGATGTATATGCATTTGGAATTGTTCTGTATGAATTGATGACTGGACAGTTACCTTATTCAAACATCAACAACAGGGACCAGATAATTTT
TATGGTGGGACGAGGATACCTGTCTCCAGATCTCAGTAAGGTACGGAGTAACTGTCCAAAAGCCATGAAGAGATTAATGGCAGAGTGCCTCAAAAAGAAA
AGAGATGAGAGACCACTCTTTCCCCAAATTCTCGCCTCTATTGAGCTGCTGGCCCGCTCATTGCCAAAAATTCACCGCAGTGCATCAGAACCCTCCTTGA
ATCGGGCTGGTTTCCAAACAGAGGATTTTAGTCTATATGCTTGTGCTTCTCCAAAAACACCCATCCAGGCAGGGGGATATGGTGCGTTTCCTGTCCACTG
A

FIGURE 8F

(SEQ ID NO: 20) b-RAF(K601E) amino acid

```
MAALSGGGGGGAEPGQALFNGDMEPEAGAGAGAAASSAADPAIPEEVWNI
KQMIKLTQEHIEALLDKFGGEHNPPSIYLEAYEEYTSKLDALQQREQQLL
ESLGNGTDFSVSSSASMDTVTSSSSSSLSVLPSSLSVFQNPTDVARSNPK
SPQKPIVRVFLPNKQRTVVPARCGVTVRDSLKKALMMRGLIPECCAVYRI
QDGEKKPIGWDTDISWLTGEELHVEVLENVPLTTHNFVRKTFFTLAFCDF
CRKLLFQGFRCQTCGYKFHQRCSTEVPLMCVNYDQLDLLFVSKFFEHHPI
PQEEASLAETALTSGSSPSAPASDSIGPQILTSPSPSKSIPIPQPFRPAD
EDHRNQFGQRDRSSSAPNVHINTIEPVNIDDLIRDQGFRGDGGSTTGLSA
TPPASLPGSLTNVKALQKSPGPQRERKSSSSSEDRNRMKTLGRRDSSDDW
EIPDGQITVGQRIGSGSFGTVYKGKWHGDVAVKMLNVTAPTPQQLQAFKN
EVGVLRKTRHVNILLFMGYSTKPQLAIVTQWCEGSSLYHHLHIIETKFEM
IKLIDIARQTAQGMDYLHAKSIIHRDLKSNNIFLHEDLTVKIGDFGLATV
ESRWSGSHQFEQLSGSILWMAPEVIRMQDKNPYSFQSDVYAFGIVLYELM
TGQLPYSNINNRDQIIFMVGRGYLSPDLSKVRSNCPKAMKRLMAECLKKK
RDERPLFPQILASIELLARSLPKIHRSASEPSLNRAGFQTEDFSLYACAS
PKTPIQAGGYGAFPVH
```

EPIDERMAL GROWTH FACTOR RECEPTOR MUTATIONS

This application claims the benefit of U.S. Ser. No. 11/361,711, filed Feb. 23, 2006, now U.S. Pat. No. 7,981,605, which claims the benefit of U.S. Provisional Application No. 60/656,263, filed Feb. 24, 2005 which is incorporated by reference in its entirety.

The present application is being filed along with a Sequence Listing in electronic format. The Sequence Listing is provided as a file entitled A-999-US-DIV_txt, created Aug. 9, 2012, which is 283 KB in size. The information in the electronic format of the Sequence Listing is incorporated herein by reference in its entirety.

FIELD

The present application relates to epidermal growth factor receptor ("EGFr") mutations, to polynucleotides encoding mutant EGFr polypeptides, to vectors containing those polynucleotides, cells expressing those polynucleotides, and antibodies that bind to those polypeptides. The present application also relates to phosphatidylinositol 3'-kinase ("PI3K") mutations, to polynucleotides encoding mutant PI3K polypeptides, to vectors containing those polynucleotides, cells expressing those polynucleotides, and antibodies that bind to those polypeptides. The present application also relates to B-Raf mutations, to polynucleotides encoding mutant B-Raf polypeptides, to vectors containing those polynucleotides, cells expressing those polynucleotides, and antibodies that bind to those polypeptides. The present application also relates to methods of diagnosing cancer; methods of treating cancer using compounds reactive with mutant EGFr polypeptides, mutant PI3K polypeptides, or mutant B-Raf polypeptides; and methods and kits for predicting the usefulness of anti-EGFr specific binding agents, anti-PI3K specific binding agents, or anti-B-Raf specific binding agents in the treatment of tumors.

BACKGROUND

Certain applications of monoclonal antibodies in cancer therapy rely on the ability of the antibody to specifically deliver to the cancerous tissues cytotoxic effector functions such as immune-enhancing isotypes, toxins or drugs. An alternative approach is to utilize monoclonal antibodies to directly affect the survival of tumor cells by depriving them of essential extracellular proliferation signals, such as those mediated by growth factors through their cell receptors. One of the attractive targets in this approach is the epidermal growth factor receptor (EGFr), which binds EGF and transforming growth factor α (TGFα) (see, e.g., Ullrich et al., Cell 61:203-212, 1990; Baselga et al., Pharmacol. Ther. 64: 127-154, 1994; Mendelsohn et al., in Biologic Therapy of Cancer 607-623, Philadelphia: J.B. Lippincott Co., 1995; Fan et al., Curr. Opin. Oncol. 10: 67-73, 1998). Binding of EGF or TGFα to EGFr, a 170 kDa transmembrane cell surface glycoprotein, triggers a cascade of cellular biochemical events, including EGFr autophosphorylation and internalization, which culminates in cell proliferation (see, e.g., Ullrich et al., Cell 61:203-212, 1990).

Several observations implicate EGFr in supporting development and progression of human solid tumors. EGF-r has been demonstrated to be overexpressed on many types of human solid tumors (see, e.g., Mendelsohn *Cancer Cells* 7:359 (1989), Mendelsohn *Cancer Biology* 1:339-344 (1990), Modjtahedi and Dean *Intl J. Oncology* 4:277-296 (1994)). For example, EGF-r overexpression has been observed in certain lung, breast, colon, gastric, brain, bladder, head and neck, ovarian, and prostate carcinomas (see, e.g., Modjtahedi and Dean *Intl J. Oncology* 4:277-296 (1994)). The increase in receptor levels has been reported to be associated with a poor clinical prognosis (see, e.g., Baselga et al. Pharmacol. Ther. 64: 127-154, 1994; Mendelsohn et al., Biologic Therapy of Cancer pp. 607-623, Philadelphia: J.B. Lippincott Co., 1995; Modjtahedi et al., Intl. J. of Oncology 4:277-296, 1994; Gullick, Br. Medical Bulletin, 47:87-98, 1991; Salomon et al., Crit. Rev. Oncol. Hematol. 19: 183-232, 1995). Both epidermal growth factor (EGF) and transforming growth factor-alpha (TGF-α) have been demonstrated to bind to EGF-r and to lead to cellular proliferation and tumor growth. In many cases, increased surface EGFr expression was accompanied by production of TGFα or EGF by tumor cells, suggesting the involvement of an autocrine growth control in the progression of those tumors (see, e.g., Baselga et al. Pharmacol. Ther. 64: 127-154, 1994; Mendelsohn et al., Biologic Therapy of Cancer pp. 607-623, Philadelphia: J.B. Lippincott Co., 1995; Modjtahedi et al., Intl. J. of Oncology 4:277-296, 1994; Salomon et al., Crit. Rev. Oncol. Hematol. 19: 183-232, 1995).

Thus, certain groups have proposed that antibodies against EGF, TGF-α, and EGF-r may be useful in the therapy of tumors expressing or overexpressing EGF-r (see, e.g., Mendelsohn *Cancer Cells* 7:359 (1989), Mendelsohn *Cancer Biology* 1:339-344 (1990), Modjtahedi and Dean *Int'l J. Oncology* 4:277-296 (1994), Tosi et al. *Intl J. Cancer* 62:643-650 (1995)). Indeed, it has been demonstrated that anti-EGF-r antibodies blocking EGF and TGF-α binding to the receptor appear to inhibit tumor cell proliferation. At the same time, however, anti-EGF-r antibodies have not appeared to inhibit EGF and TGF-α independent cell growth (Modjtahedi and Dean *Int'l J. Oncology* 4:277-296 (1994)).

Monoclonal antibodies specific to the human EGFr, capable of neutralizing EGF and TGFα binding to tumor cells and of inhibiting ligand-mediated cell proliferation in vitro, have been generated from mice and rats (see, e.g., Baselga et al., Pharmacol. Ther. 64: 127-154, 1994; Mendelsohn et al., in Biologic Therapy of Cancer 607-623, Philadelphia: J.B. Lippincott Co., 1995; Fan et al., Curr. Opin. Oncol. 10: 67-73, 1998; Modjtahedi et al., Intl. J. Oncology 4: 277-296, 1994). Some of those antibodies, such as the mouse 108, 225 (see, e.g., Aboud-Pirak et al., J. Natl. Cancer Inst. 80: 1605-1611, 1988) and 528 (see, e.g., Baselga et al., Pharmacol. Ther. 64: 127-154, 1994; Mendelsohn et al., in Biologic Therapy of Cancer 607-623, Philadelphia: J.B. Lippincott Co., 1995) or the rat ICR16, ICR62 and ICR64 (see, e.g., Modjtajedi et al., Intl. J. Oncology 4: 277-296, 1994; Modjtahedi et al., Br. J. Cancer 67:247-253, 1993; Modjtahedi et al., Br. J. Cancer 67: 254-261, 1993) monoclonal antibodies, were evaluated extensively for their ability to affect tumor growth in xenograft mouse models. Most of the anti-EGFr monoclonal antibodies were efficacious in preventing tumor formation in athymic mice when administered together with the human tumor cells (Baselga et al. Pharmacol. Ther. 64: 127-154, 1994; Modjtahedi et al., Br. J. Cancer 67: 254-261, 1993). When injected into mice bearing established human tumor xenografts, the mouse monoclonal antibodies 225 and 528 caused partial tumor regression and required the co-administration of chemotherapeutic agents, such as doxorubicin or cisplatin, for eradication of the tumors (Baselga et al. Pharmacol. Ther. 64: 127-154, 1994; Mendelsohn et al., in Biologic Therapy of Cancer 607-623, Philadelphia: J.B. Lippincott Co., 1995; Fan et al., Cancer Res. 53: 4637-4642, 1993; Baselga et al., J. Natl. Cancer Inst. 85: 1327-1333, 1993). A chimeric version of the 225 monoclonal antibody (C225), in which the mouse antibody variable regions are linked to human constant regions, exhibited an improved in vivo anti-tumor activity but only at high doses (see, e.g., Goldstein et al., Clinical Cancer Res. 1: 1311-1318, 1995; Prewett et al., J. Immunother. Emphasis Tumor Immunol. 19: 419-427, 1996). The rat ICR16, ICR62, and ICR64 antibodies caused regression of established tumors but not their complete eradication (Modjtahedi et al., Br. J. Cancer 67: 254-261, 1993). These results established EGFr as a promising target for antibody therapy against EGFr-expressing solid tumors and led to human clinical trials with the C225 monoclonal antibody in multiple human solid cancers (see, e.g., Baselga et al. Pharmacol. Ther. 64: 127-154, 1994; Mendelsohn et al., Biologic Therapy of Cancer pp. 607-623, Philadelphia: J.B. Lippincott Co., 1995; Modjtahedi et al., Intl. J. of Oncology 4:277-296, 1994).

Certain advances in the biological arts made it possible to produce a fully human anti-EGFr antibody. Using mice transgenic for human immunoglobulin genes (Xenomouse™ technology, Abgenix, Inc.), human antibodies specific for human EGFr were developed (see, e.g., Mendez, Nature Genetics, 15: 146-156, 1997; Jakobovits, Advanced Drug Delivery Reviews, 31(1-2): 33-42, 1998; Jakobovits, Expert Opinion on Investigational Drugs, 7(4): 607-614, 1998; Yang et al., Crit. Rev. Oncol. Hematol. 38(1):17-23, 2001; WO98/24893; WO 98/50433). One such antibody, panitumumab, a human IgG2 monoclonal antibody with an affinity of $5\times10^{-11}$ M for human EGFr, has been shown to block binding of EGF to the EGFr, to block receptor signaling, and to inhibit tumor cell activation and proliferation in vitro (see, e.g., WO98/50433; U.S. Pat. No. 6,235,883). Studies in athymic mice have demonstrated that panitumumab also has in vivo activity, not only preventing the formation of human epidermoid carcinoma A431 xenografts in athymic mice, but also eradicating already-established large A431 tumor xenografts (see, e.g., Yang et al., Crit. Rev. Oncol. Hematol. 38(1):17-23, 2001; Yang et al., Cancer Res. 59(6):1236-43, 1999). Panitumumab has been considered for the treatment of renal carcinoma, colorectal adenocarcinoma, prostate cancer, and non small cell squamous lung carcinoma, among other cancers (see, e.g., U.S. Patent Publication No. 2004/0033543), and clinical trials are underway with that antibody.

In certain cell types, the binding of growth factors, such as EGFr, prevents apoptosis by stimulation of phosphatidylinositol 3-kinase ("PI3K") and B-Raf. PI3K activation triggers a molecular cascade leading to the downregulation of the central pathways controlling programmed cell death (Yao, R., Science 267:2003-2006, 1995). Members of the Raf family also have been identified as regulators of programmed cell death in mammals (Hunter, Cell 80:225-236, 1995). In Raf knockouts, mice lacking B-Raf showed disturbances in cell survival, while mice lacking Raf-1 or A-Raf did not show such disturbances (see, e.g., Pritchard, Curr. Biol. 6:614-617, 1996; Wojnowski, Nat. Genet. 16:293-297, 1997), indicating that B-Raf may possess specific functions in cell death regulation. Both PI3K and B-Raf are of interest in cell proliferation disorders, particularly cancer.

SUMMARY

In certain embodiments, an isolated polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 is provided. In certain embodiments, an isolated polypeptide consisting of at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 is provided.

In certain embodiments, an isolated polynucleotide encoding a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 is provided. In certain embodiments, an isolated polynucleotide encoding a polypeptide consisting of at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 is provided.

In certain embodiments, an isolated polypeptide comprising at least one amino acid sequence selected from SEQ ID NO: 15, SEQ ID NO: 16, and SEQ ID NO: 17 is provided. In certain embodiments, an isolated polypeptide consisting of at least one amino acid sequence selected from SEQ ID NO: 15, SEQ ID NO: 16, and SEQ ID NO: 17 is provided.

In certain embodiments, an isolated polynucleotide encoding a polypeptide comprising at least one amino acid sequence selected from SEQ ID NO: 15, SEQ ID NO: 16, and SEQ ID NO: 17 is provided. In certain embodiments, an isolated polynucleotide encoding a polypeptide consisting of at least one amino acid sequence selected from SEQ ID NO: 15, SEQ ID NO: 16, and SEQ ID NO: 17 is provided.

In certain embodiments, an isolated polypeptide comprising at least one amino acid sequence selected from SEQ ID NO: 19 and SEQ ID NO: 20 is provided. In certain embodiments, an isolated polypeptide consisting of at least one amino acid sequence selected from SEQ ID NO: 19 and SEQ ID NO: 20 is provided.

In certain embodiments, an isolated polynucleotide encoding a polypeptide comprising at least one amino acid sequence selected from SEQ ID NO: 19 and SEQ ID NO: 20 is provided. In certain embodiments, an isolated polynucleotide encoding a polypeptide consisting of at least one amino acid sequence selected from SEQ ID NO: 19 and SEQ ID NO: 20 is provided.

In certain embodiments, a vector comprising at least one isolated polynucleotide encoding a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 is provided. In certain embodiments, a host cell comprising the vector is provided. In certain embodiments, a cell transformed with at least one isolated polynucleotide encoding a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 is provided.

In certain embodiments, a method of preparing a polypeptide is provided. In certain embodiments, the method comprises culturing a host cell comprising a vector that comprises at least one isolated polynucleotide encoding a polypeptide under conditions effective for polypeptide production. In certain embodiments, the method comprises culturing a cell comprising at least one isolated polynucleotide encoding a polypeptide under conditions effective for polypeptide production. In certain embodiments, the method further comprises isolating the polypeptide. In certain embodiments, a polypeptide prepared by the method is provided.

In certain embodiments, a fusion protein comprising an isolated polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 fused to a heterologous polypeptide is provided.

In certain embodiments, a specific binding agent which is capable of binding to an isolated polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 is provided. In certain embodiments, the specific binding agent is selected from at least one molecule selected from: an antibody, an antibody wherein the heavy chain and the light chain are connected by a linker, a single-Fv antibody, an immunologically functional immunoglobulin fragment, a Fab antibody, a Fab' antibody, a $(Fab')_2$ antibody, a monoclonal antibody, a polyclonal antibody, an anti-idiotypic antibody, a fully human antibody, a humanized antibody, a chimeric antibody, a CDR-grafted antibody, and an antibody that inhibits binding of EGF to an isolated polypeptide of comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, SEQ ID NO: 20.

In certain embodiments, a method of obtaining an antibody capable of binding at least one polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 is provided. In certain embodiments, the method comprises administering at least one polypeptide comprising at least one sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 to an animal. In certain embodiments, the method further comprises obtaining an antibody capable of binding at least one polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13 from the animal.

In certain embodiments, a transgenic non-human animal comprising at least one polynucleotide encoding at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 is provided.

In certain embodiments, a polynucleotide encoding at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 attached to a solid support is provided. In certain embodiments, a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 attached to a solid support is provided.

In certain embodiments, an array of polynucleotides comprising at least one polynucleotide encoding at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 is provided. In certain embodiments, an array of polypeptides comprising at least one polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 is provided.

In certain embodiments, a nucleic acid probe which hybridizes to a polynucleotide encoding a region of a mutant EGFr polypeptide is provided. In certain embodiments, the region comprises at least one EGFr mutation selected from L688P, Q701H, K745N, C781R, a histidine insertion between amino acids 771 and 772, T790M, L828stop, Q849R, F910L, and V948A. In certain embodiments, the nucleic acid probe hybridizes to a complement of the polynucleotide.

In certain embodiments, a method of diagnosing a disease or condition which is related to one or more EGFr mutations in a subject is provided. In certain embodiments, a method of diagnosing a susceptibility to a disease or condition which is related to one or more EGFr mutations in a subject is provided. In certain embodiments, the method comprises determining the presence or amount of expression of a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 in a sample from the subject. In certain embodiments, the method further comprises diagnosing a disease or condition which is related to one or more EGFr mutations based on the presence or amount of expression of the polypeptide. In certain embodiments, the method further comprises diagnosing a susceptibility to a disease or condition which is related to one or more EGFr mutations based on the presence or amount of expression of the polypeptide.

In certain embodiments, a method of determining the presence or absence of a polynucleotide encoding a mutant EGFr polypeptide in a sample is provided. In certain embodiments, a method of determining the presence or absence of a mutant EGFr polypeptide in a sample is provided. In certain embodiments, the method comprises exposing a sample to a probe which hybridizes to a polynucleotide encoding a region of a mutant EGFr polypeptide, wherein the region comprises at least one EGFr mutation selected from L688P, Q701H, K745N, C781R, a histidine insertion between amino acids 771 and 772, T790M, L828stop, Q849R, F910L, and V948A. In certain embodiments, the method further comprises determining the presence or absence of a polynucleotide encoding a mutant EGFr polypeptide in the sample. In certain embodiments, the method comprises determining the presence or absence of a mutant EGFr mutant EGFr polypeptide in the sample.

In certain embodiments, a method of diagnosing an EGFr-related cancer in a subject is provided. In certain embodiments, the method comprises determining the presence or absence of at least one mutant EGFr polypeptide comprising at least one mutation selected from: L688P, Q701H, K745N, C781R, a histidine insertion between amino acids 771 and 772, T790M, L828stop, Q849R, F910L, and V948A in a sample from the subject. In certain embodiments, the method comprises determining the presence or absence of at least one mutant EGFr polynucleotide encoding a polypeptide comprising at least one mutation selected from: L688P, Q701H, K745N, C781R, a histidine insertion between amino acids 771 and 772, T790M, L828stop, Q849R, F910L, and V948A in a sample from the subject. In certain embodiments, the presence of the at least mutant EGFr polypeptide diagnoses an EGFr-related cancer in the subject. In certain embodiments, the presence of the at least one mutant EGFr polynucleotide diagnoses an EGFr-related cancer in the subject.

In certain embodiments, a method of determining a likelihood of development of an EGFr-related cancer in a subject is provided. In certain embodiments, the method comprises determining the presence or absence of at least one mutant EGFr polypeptide comprising at least one mutation selected from: L688P, Q701H, K745N, C781R, a histidine insertion between amino acids 771 and 772, T790M, L828stop, Q849R, F910L, and V948A in a sample from the subject. In certain embodiments, the method comprises determining the presence or absence of at least one mutant EGFr polynucleotide encoding a polypeptide comprising at least one mutation selected from: L688P, Q701H, K745N, C781R, a histidine insertion between amino acids 771 and 772, T790M, L828stop, Q849R, F910L, and V948A in a sample from the subject. In certain embodiments, the presence of the at least mutant EGFr polypeptide is indicative of a likelihood of development of an EGFr-related cancer in the subject. In certain embodiments, the presence of the at least one mutant EGFr polynucleotide is indicative of a likelihood of development of an EGFr-related cancer in the subject.

In certain embodiments, an EGFr-related cancer is non small cell lung carcinoma.

In certain embodiments, a method of screening for a modulator of activity of at least one mutant EGFr polypeptide comprising at least one mutation selected from L688P, Q701H, K745N, C781R, a histidine insertion between amino acids 771 and 772, T790M, L828stop, Q849R, F910L, and V948A is provided. In certain embodiments, the method comprises contacting a cell with a test compound and detecting if the test compound modulates the activity of the mutant EGFr polypeptide. In certain embodiments, a compound identified by the method is provided. In certain embodiments, a method of treating a disease or condition which is related to at least one EGFr mutation selected from L688P, Q701H, K745N, C781R, a histidine insertion between amino acids 771 and 772, T790M, L828stop, Q849R, F910L, and V948A is provided. In certain embodiments, the method comprises administering the compound to a subject in need of treatment for the disease or condition which is related to at least one EGFr mutation.

In certain embodiments, a method for treating a subject for a disease or condition which is related to at least one EGFr mutation is provided. In certain embodiments, the method comprises detecting at least one EGFr mutation in a polynucleotide from the subject, wherein detection of at least one EGFr mutation indicates that the patient has an increased susceptibility for developing a disease or condition which is related to at least one EGFr mutation. In certain embodiments, the method comprises detecting at least one EGFr mutation in a polynucleotide from the subject, wherein detection of at least one EGFr mutation indicates that the patient has a disease or condition which is related to at least one EGFr mutation. In certain embodiments, the method further comprises administering an antibody to the subject that specifically binds a mutant EGFr polypeptide. In certain embodiments, the antibody is a human antibody. In certain embodiments, the antibody is panitumumab or an antigen-binding region thereof.

In certain embodiments, an EGFr mutation is selected from L688P, Q701H, K745N, C781R, a histidine insertion between amino acids 771 and 772, T790M, L828stop, Q849R, F910L, and V948A.

In certain embodiments, a disease or condition which is related to at least one EGFr mutation is non small cell lung carcinoma.

In certain embodiments, a method of treating a disease or condition which is related to at least one EGFr mutation is provided. In certain embodiments, the method comprises administering a polynucleotide antisense to the polynucleotide encoding at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 15, SEQ ID NO: 16, SEQ ID NO: 17, SEQ ID NO: 19, and SEQ ID NO: 20 to a subject in need of such treatment.

In certain embodiments, a method for establishing a mutant EGFr population profile in a specific population of individuals is provided. In certain embodiments, the method comprises determining the presence of at least one EGFr mutation in a genetic profile of the individuals in a population. In certain embodiments, the method further comprises establishing a relationship between mutant EGFr genetic profiles and specific characteristics of the individuals. In certain embodiments, the specific characteristics of the individuals include a susceptibility to developing a disease or condition which is related to an EGFr mutation. In certain embodiments, the specific characteristics of the individuals include exhibiting a disease or condition which is related to an EGFr mutation.

In certain embodiments, a method of predicting the efficacy of gefitinib treatment on a disease or condition in a subject is provided. In certain embodiments, the method comprises determining the presence or absence of EGFr mutation T790M in a mutant EGFr polypeptide of the subject. In certain embodiments, the presence of the EGFr mutation T790M in one or more mutant EGFr polypeptides indicates resistance to treatment with gefitinib.

In certain embodiments, a method of determining responsiveness to treatment with an anti-EGFr antibody in a subject suffering from cancer is provided. In certain embodiments, the method comprises determining the presence or absence of EGFr mutation T790M in the subject. In certain embodiments, the antibody is panitumumab or cetuximab.

In certain embodiments, a kit for detecting a polynucleotide encoding a mutant EGFr polypeptide in a subject is provided. In certain embodiments, the kit comprises a probe which hybridizes to a polynucleotide encoding a region of a mutant EGFr polypeptide, wherein the region comprises at least one EGFr mutation selected from L688P, Q701H, K745N, C781R, a histidine insertion between amino acids 771 and 772, T790M, L828stop, Q849R, F910L, and V948A. In certain embodiments, the kit further comprises two or more amplification primers. In certain embodiments, the kit further comprises a detection component. In certain embodiments, the kit further comprises a nucleic acid sampling component.

BRIEF DESCRIPTION OF THE FIGURES

FIG. 1 is a table showing a mutational analysis of non small cell lung carcinoma ("NSCLC") tumor samples from twenty patients, according to the work described in Example 1. EGFr exons 18, 19, 20, 21, and 23, PI3K exons 9 and 20, and B-Raf exon 15 from the genomic DNA of each tumor were amplified, sequenced, and compared to wild-type EGFr, PI3K, or B-Raf sequence.

FIG. 2 is a table showing a mutational analysis of colorectal adenocarcinoma ("CRC") tumor samples from twenty patients, according to the work described in Example 1. EGFr exons 18, 19, 20, 21, and 23, PI3K exons 9 and 20, and B-Raf exon 15 from the genomic DNA of each tumor were amplified, sequenced, and compared to wild-type EGFr, PI3K, or B-Raf sequence.

FIG. 3 is a table showing a mutational analysis of NSCLC tumor samples from thirty-nine patients, according to the work described in Example 2. EGFr exons 18, 19, 20, 21, and 23 and B-Raf exons 11 and 15 from the genomic DNA of each tumor were amplified, sequenced, and compared to wild-type EGFr or B-Raf sequence.

FIGS. 5A through 5F show alignments of certain mutant EGFr polynucleotide (SEQ ID NOs: 59, 64, 68, and 72) and polypeptide (SEQ ID NOs: 21, 66, 70, and 74) sequences and certain mutant PI3K polynucleotide (SEQ ID NOs: 76 and 80) and polypeptide (SEQ DI NOs: 78 and 82) sequences with the corresponding wild-type sequences (SEQ ID NOs: 52, 63, 67, 71, 62, 65, 69, 73, 75, 79, 77, and 81).

FIGS. 6A through 6Z show polynucleotide (SEQ ID NOs: 55, 41, 40, 42, 43, 44, 46, 45, 56, 47, 61, 49, and 48) and polypeptide (SEQ ID NOs: 1 to 13) sequences for wild-type and mutant EGFr molecules.

FIGS. 7A through 7H show polynucleotide (SEQ ID NOs: 58, 53, 50, and 54) and polypeptide (SEQ ID NOs: 14 to 17) sequences for wild-type and mutant PI3K molecules.

FIGS. 8A through 8F show polynucleotide (SEQ ID NOs: 60, 51, and 57) and polypeptide (SEQ ID NOs: 18 to 20) sequences for wild-type and mutant B-Raf molecules.

DETAILED DESCRIPTION OF CERTAIN PREFERRED EMBODIMENTS

Figure 4:
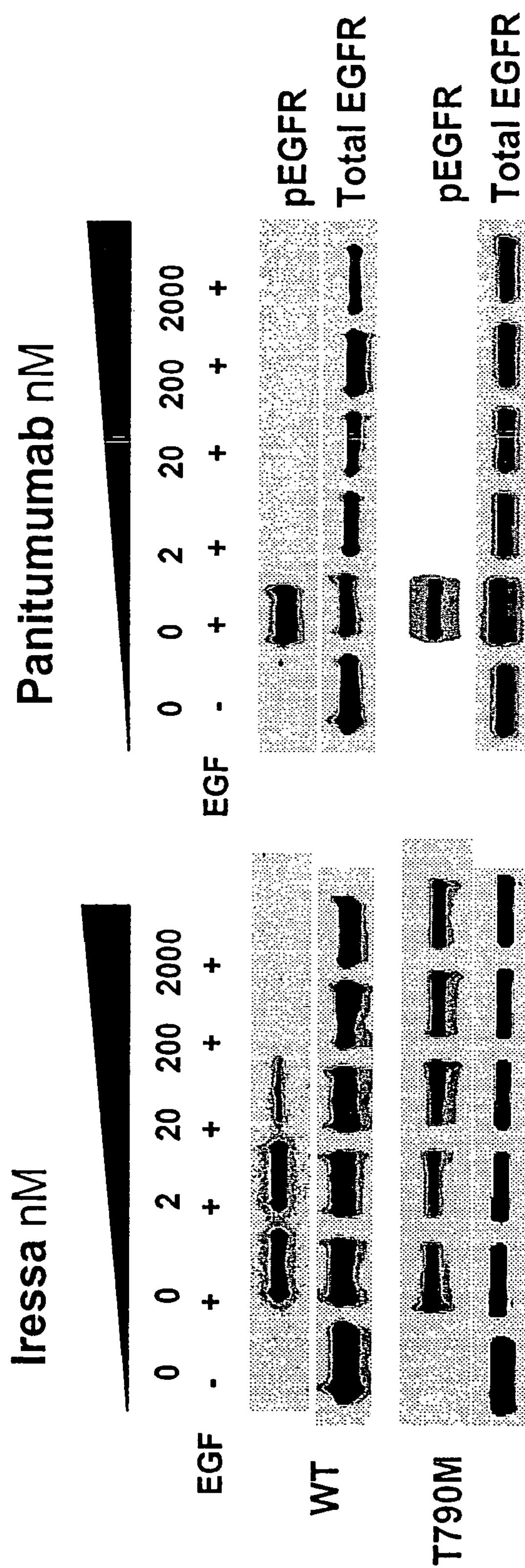
FIG. 4 shows radioactive gel electrophoresis analyses of the inhibitory activity of gefitinib and panitumumab on wild-type and T790M EGFr autophosphorylation, according to the work described in Example 3.

All references cited herein, including patents, patent applications, papers, textbooks, and the like, and the references cited therein, to the extent that they are not already, are hereby incorporated herein by reference in their entirety. The section headings used herein are for organizational purposes only and are not to be construed as limiting the subject matter described.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to the manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "isolated polynucleotide" and "isolated nucleic acid" are used interchangeably, and as used herein shall mean a polynucleotide of genomic, cDNA, or synthetic origin or some combination thereof, which by virtue of its origin (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The terms "isolated protein" and "isolated polypeptide" are used interchangeably, and as referred to herein mean a protein of cDNA, recombinant RNA, or synthetic origin, or some combination thereof, which by virtue of its origin, or source of derivation, (1) is not associated with proteins found in nature, (2) is free of other proteins from the same source, e.g. free of murine proteins, (3) is expressed by a cell from a different species, or (4) does not occur in nature.

The terms "polypeptide" and "protein" are used interchangeably and are used herein as a generic term to refer to native protein, fragments, peptides, or analogs of a polypeptide sequence. Hence, native protein, fragments, and analogs are species of the polypeptide genus.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "L688P" with reference to the EGFr polypeptide indicates that there is a leucine at amino acid number 688 of the wild-type EGFr sequence, and that leucine is replaced with a proline in the mutant EGFr sequence.

The terms "mutant EGFr polypeptide" and "mutant EGFr protein" are used interchangeably, and refer to an EGFr polypeptide comprising at least one EGFr mutation selected from L688P, Q701H, K745N, C781R, a histidine insertion between amino acids 771 and 772, T790M, L828stop, Q849R, F910L, and V948A. Certain exemplary mutant EGFr polypeptides include, but are not limited to, allelic variants, splice variants, derivative variants, substitution variants, deletion variants, and/or insertion variants, fusion polypeptides, orthologs, and interspecies homologs. In certain embodiments, a mutant EGFr polypeptide includes additional residues at the C- or N-terminus, such as, but not limited to, leader sequence residues, targeting residues, amino terminal methionine residues, lysine residues, tag residues and/or fusion protein residues.

The terms "mutant PI3K polypeptide" and "mutant PI3K protein" are used interchangeably, and refer to a PI3K polypeptide comprising at least one PI3K mutation selected from E542K, E545A, and H1047L. Certain exemplary mutant PI3K polypeptides include, but are not limited to, allelic variants, splice variants, derivative variants, substitution variants, deletion variants, and/or insertion variants, fusion polypeptides, orthologs, and interspecies homologs. In certain embodiments, a mutant PI3K polypeptide includes additional residues at the C- or N-terminus, such as, but not limited to, leader sequence residues, targeting residues, amino terminal methionine residues, lysine residues, tag residues and/or fusion protein residues.

The terms "mutant B-Raf polypeptide" and "mutant B-Raf protein" are used interchangeably, and refer to a B-Raf polypeptide comprising at least one B-Raf mutation selected from V600E and K601 E. Certain exemplary mutant B-Raf polypeptides include, but are not limited to, allelic variants, splice variants, derivative variants, substitution variants, deletion variants, and/or insertion variants, fusion polypeptides, orthologs, and interspecies homologs. In certain embodiments, a mutant B-Raf polypeptide includes additional residues at the C- or N-terminus, such as, but not limited to, leader sequence residues, targeting residues, amino terminal methionine residues, lysine residues, tag residues and/or fusion protein residues.

The term "mutant EGFr fusion protein" refers to a fusion of one or more amino acids (such as a heterologous polypeptide) at the amino- or carboxyl-terminus of a mutant EGFr polypeptide.

The term "mutant PI3K fusion protein" refers to a fusion of one or more amino acids (such as a heterologous polypeptide) at the amino- or carboxyl-terminus of a mutant PI3K polypeptide.

The term "mutant B-Raf fusion protein" refers to a fusion of one or more amino acids (such as a heterologous polypeptide) at the amino- or carboxyl-terminus of a mutant B-Raf polypeptide.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to the positioning of components such that they are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequences; in eukaryotes, generally, such control sequences include promoters and transcription termination sequences. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes, although oligonucleotides may be double stranded, e.g. for use in the construction of a gene mutant. Oligonucleotides of the invention can be either sense or antisense oligonucleotides.

The terms "mutant EGFr polynucleotide", "mutant EGFr oligonucleotide," and "mutant EGFr nucleic acid" are used interchangeably, and refer to a polynucleotide encoding an EGFr polypeptide comprising at least one EGFr mutation selected from L688P, Q701H, K745N, C781R, a histidine insertion between amino acids 771 and 772, T790M, L828stop, Q849R, F910L, and V948A.

The terms "mutant PI3K polynucleotide", "mutant PI3K oligonucleotide," and "mutant PI3K nucleic acid" are used interchangeably, and refer to a polynucleotide encoding a PI3K polypeptide comprising at least one PI3K mutation selected from E542K, E545A, and H1047L.

The terms "mutant B-Raf polynucleotide", "mutant B-Raf oligonucleotide," and "mutant B-Raf nucleic acid" are used interchangeably, and refer to a polynucleotide encoding a B-Raf polypeptide comprising at least one B-Raf mutation selected from L688P, Q701H, K745N, C781R, a histidine insertion between amino acids 771 and 772, T790M, L828stop, Q849R, F910L, and V948A.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides, and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between polynucleotides, oligonucleotides, and fragments and a nucleic acid sequence of interest will be at least 80%, and more typically with preferably increasing homologies of at least 85%, 90%, 95%, 96%, 97%, 98%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to that volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 96, 97, 98, or 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. The term "amino acid" or "amino acid residue," as used herein, refers to naturally occurring L amino acids or to D amino acids. The commonly used one- and three-letter abbreviations for amino acids are used herein (Bruce Alberts et al., *Molecular Biology of the Cell*, Garland Publishing, Inc., New York (4th ed. 2002)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction. Sequence regions on the DNA strand having the same sequence as the RNA and which are 5' to the 5' end of the RNA transcript are referred to as "upstream sequences". Sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95, 96, 97, or 98 percent sequence identity, and most preferably at least 99 percent sequence identity. Preferably, residue positions which are not identical differ by conservative amino acid substitutions. As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. Conservative amino acid substitutions are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine as a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "analog" as used herein refers to polypeptides which are comprised of a segment of at least 25 amino acids that has substantial identity to a portion of an amino acid sequence of a naturally occurring polypeptide and which has at least one of the activities of the naturally occurring polypeptide. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. Those types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (see Bowie et al. *Science* 253:164 (1991)). Those of skill in the art can recognize sequence motifs and structural conformations that may be used to define structural and functional domains in accordance with the invention.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an antibody. In certain embodiments, a specific binding agent is an antigen binding region.

The term "specific binding agent to a mutant EGFr polypeptide" refers to a specific binding agent that specifically binds any portion of a mutant EGFr polypeptide. In certain embodiments, a specific binding agent to a mutant EGFr polypeptide is an antibody to a mutant EGFr polypeptide. In certain embodiments, a specific binding agent to a mutant EGFr polypeptide is an antigen binding region.

The term "specific binding agent to a mutant PI3K polypeptide" refers to a specific binding agent that specifically binds any portion of a mutant PI3K polypeptide. In certain embodiments, a specific binding agent to a mutant PI3K polypeptide is an antibody to a mutant PI3K polypeptide. In certain embodiments, a specific binding agent to a mutant PI3K polypeptide is an antigen binding region.

The term "specific binding agent to a mutant B-Raf polypeptide" refers to a specific binding agent that specifically binds any portion of a mutant B-Raf polypeptide. In certain embodiments, a specific binding agent to a mutant B-Raf polypeptide is an antibody to a mutant B-Raf polypeptide. In certain embodiments, a specific binding agent to a mutant B-Raf polypeptide is an antigen binding region.

The term "specifically binds" refers to the ability of a specific binding agent to bind to a target with greater affinity than it binds to a non-target. In certain embodiments, specific binding refers to binding for a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method. In certain embodiments, an antibody is said to specifically bind an antigen when the dissociation constant between the antibody and one or more of its recognized epitopes is ≤1 μM, preferably ≤100 nM and most preferably ≤10 nM.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985; Novotny and Haber, *Proc. Natl. Acad. Sci. U.S.A.* 82:4592 (1985); Chothia et al., *Nature* 342:877-883 (1989)).

The term "antibody" refers to both an intact antibody and a antigen binding fragment thereof which competes with the intact antibody for specific binding. "Antigen binding fragment thereof" refers to a portion or fragment of an intact antibody molecule, wherein the fragment retains the antigen-binding function. Binding fragments are produced by recombinant DNA techniques, or by enzymatic or chemical cleavage of intact antibodies such as by cleavage with papain. Binding fragments include Fab, Fab', $F(ab')_2$, Fv, single-chain antibodies ("scFv"), Fd' and Fd fragments. Methods for producing the various fragments from monoclonal antibodies are well known to those skilled in the art (see, e.g., Pluckthun, 1992, Immunol. Rev. 130:151-188). An antibody other than a "bispecific" or "bifunctional" antibody is understood to have each of its binding sites be identical. An antibody substantially inhibits adhesion of a receptor to a counterreceptor when an excess of antibody reduces the quantity of receptor bound to counterreceptor by at least about 20%, 40%, 60%, or 80%, and more usually greater than about 85%, 90%, 95%, 96%, 97%, 98%, or 99% (as measured in an in vitro competitive binding assay).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and terminal or internal amino acid sequencing by use of a spinning cup sequenator, or (2) to homogeneity by SDS-PAGE under reducing or non-reducing conditions using Coomassie blue or, preferably, silver stain. An isolated antibody includes the antibody in situ within recombinant cells since at least one component of the antibody's natural environment will not be present. Ordinarily, however, isolated antibody will be prepared by at least one purification step.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991). The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity on the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain; Kabat et al., *Sequences of Proteins of Immunological Interest,* 5$^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "complementarity determining regions" or "CDRs," when used herein, refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

"Antibody-dependent cell-mediated cytotoxicity" and "ADCC" refer to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1988).

The term "epitope" includes any protein determinant capable of specific binding to an immunoglobulin and/or T-cell receptor. Epitopic determinants usually consist of chemically active surface groupings of molecules such as amino acids or sugar side chains and usually have specific three dimensional structural characteristics, as well as specific charge characteristics.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent groups, biotinyl groups, and predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, 96, 97, 98, or 99%. Most preferably, the object species is purified to essential homogeneity (contaminant species cannot be detected in the composition by conventional detection methods) wherein the composition consists essentially of a single macromolecular species.

The term patient includes human and animal subjects.

The terms "mammal" and "animal" for purposes of treatment refers to any animal classified as a mammal, including humans, domestic and farm animals, and zoo, sports, or pet animals, such as dogs, horses, cats, cows, etc. Preferably, the mammal is human.

The term "disease state" refers to a physiological state of a cell or of a whole mammal in which an interruption, cessation, or disorder of cellular or body functions, systems, or organs has occurred.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from one or more treatments. This includes chronic and acute disorders or disease including those pathological conditions which predispose the mammal to the disorder in question. Non-limiting examples of disorders to be treated herein include benign and malignant tumors, leukemias, and lymphoid malignancies, in particular breast, rectal, ovarian, stomach, endometrial, salivary gland, kidney, colon, thyroid, pancreatic, prostate or bladder cancer. A preferred disorder to be treated in accordance with the present invention is a malignant tumor, such as cervical carcinomas and cervical intraepithelial squamous and glandular neoplasia, renal cell carcinoma (RCC), esophageal tumors, and carcinoma-derived cell lines.

A "disease or condition related to a mutant EGFr polypeptide" includes one or more of the following: a disease or condition caused by a mutant EGFr polypeptide; a disease or condition contributed to by a mutant EGFr polypeptide; a disease or condition that causes a mutant EGFr polypeptide; and a disease or condition that is associated with the presence of a mutant EGFr polypeptide. In certain embodiments, the disease or condition related to a mutant EGFr polypeptide may exist in the absence of the mutant EGFr polypeptide. In certain embodiments, the disease or condition related to a mutant EGFr polypeptide may be exacerbated by the presence of a mutant EGFr polypeptide. In certain embodiments, a disease or condition related to a mutant EGFr polypeptide is a cancer. Exemplary cancers include, but are not limited to, non small cell lung carcinoma, breast, colon, gastric, brain, bladder, head and neck, ovarian, and prostate carcinomas.

A "disease or condition related to a mutant PI3K polypeptide" includes one or more of the following: a disease or condition caused by a mutant PI3K polypeptide; a disease or condition contributed to by a mutant PI3K polypeptide; a disease or condition that causes a mutant PI3K polypeptide; and a disease or condition that is associated with the presence of a mutant PI3K polypeptide. In certain embodiments, the disease or condition related to a mutant PI3K polypeptide may exist in the absence of the mutation. In certain embodiments, the disease or condition related to a mutant PI3K polypeptide may be exacerbated by the presence of a mutant PI3K polypeptide. In certain embodiments, a disease or condition related to a mutant PI3K polypeptide is a cancer. Exemplary cancers include, but are not limited to, non small cell lung carcinoma, breast, colon, gastric, brain, bladder, head and neck, ovarian, and prostate carcinomas A "disease or condition related to a mutant B-Raf polypeptide" includes one or more of the following: a disease or condition caused by a mutant B-Raf polypeptide; a disease or condition contributed to by a mutant B-Raf polypeptide; a disease or condition that causes a mutant B-Raf polypeptide; and a disease or condition that is associated with the presence of a mutant B-Raf polypeptide. In certain embodiments, the disease or condition related to a mutant B-Raf polypeptide may exist in the absence of the mutation. In certain embodiments, the disease or condition related to a mutant B-Raf polypeptide may be exacerbated by the presence of a mutant B-Raf polypeptide. In certain embodiments, a disease or condition related to a mutant B-Raf polypeptide is a cancer. Exemplary cancers include, but are not limited to, non small cell lung carcinoma, breast, colon, gastric, brain, bladder, head and neck, ovarian, and prostate carcinomas.

In "combined therapy," patients are treated with a specific binding agent for a target antigen in combination with a chemotherapeutic or antineoplastic agent and/or radiation therapy. The cancer is treated under protocol by the addition of a specific binding agent to a mutant EGFr polypeptide, a specific binding agent to a mutant PI3K polypeptide, and/or a specific binding agent to a mutant B-Raf polypeptide to standard first and second line therapy. Protocol designs will address effectiveness as assessed by reduction in tumor mass as well as the ability to reduce usual doses of standard chemotherapy. These dosage reductions will allow additional and/or prolonged therapy by reducing dose-related toxicity of the chemotherapeutic agent.

"Monotherapy" refers to the treatment of a disorder by administering immunotherapy to patients without an accompanying chemotherapeutic or antineoplastic agent.

Certain Embodiments

Polypeptides, Fragments, and Fusion Proteins

In certain embodiments, a deletion variant is a fragment of a full-length mutant EGFr polypeptide. In certain embodiments, such a fragment corresponds to an epitope of a mutant EGFr polypeptide. In certain embodiments, such a fragment is naturally-occurring (e.g., due to in vivo protease activity). In certain embodiments, such a fragment is chemically synthesized. In certain embodiments, such a fragment may be linked to a polypeptide to form a mutant EGFr fusion protein. In certain embodiments, such a fragment is at least 5, 6, 8 or 10 amino acids long. In certain embodiments, such a fragment is at least 14, at least 20, at least 50, or at least 70 amino acids long.

In certain embodiments, a deletion variant is a fragment of a full-length mutant PI3K polypeptide is provided. In certain embodiments, such a fragment corresponds to an epitope of a mutant PI3K polypeptide. In certain embodiments, such a fragment is naturally-occurring (e.g., due to in vivo protease activity). In certain embodiments, such a fragment is chemically synthesized. In certain embodiments, such a fragment may be linked to a polypeptide to form a mutant PI3K fusion protein. In certain embodiments, such a fragment is at least 5, 6, 8 or 10 amino acids long. In certain embodiments, such a fragment is at least 14, at least 20, at least 50, or at least 70 amino acids long.

In certain embodiments, a deletion variant is a fragment of a full-length mutant B-Raf polypeptide is provided. In certain embodiments, such a fragment corresponds to an epitope of a mutant B-Raf polypeptide. In certain embodiments, such a fragment is naturally-occurring (e.g., due to in vivo protease activity). In certain embodiments, such a fragment is chemically synthesized. In certain embodiments, such a fragment may be linked to a polypeptide to form a mutant B-Raf fusion protein. In certain embodiments, such a fragment is at least 5, 6, 8 or 10 amino acids long. In certain embodiments, such a fragment is at least 14, at least 20, at least 50, or at least 70 amino acids long.

In certain embodiments, a mutant polypeptide may be linked to at least one non-proteinaceous. Such groups include, but are not limited to, N-linked or O-linked carbohydrate chains, water-soluble polymers such as polyethylene glycol (PEG), and derivatives thereof (see for example U.S. Pat. No. 4,179,337). Other chemical modifications within the meaning of this term include, but are not limited to, ethylene glycol/propylene glycol copolymers, carboxymethylcellulose, dextran, polyvinyl alcohol, and related molecules.

In certain embodiments, a mutant EGFr polypeptide may be modified at random positions within the molecule, or at predetermined positions within the molecule and may include one, two, three or more attached chemical moieties. In certain embodiments, a mutant EGFr polypeptide may also be modified at pre-determined positions in the polypeptide, such as at the amino terminus, or at a selected lysine or arginine residue within the polypeptide. Other chemical modifications include, but are not limited to, a detectable label, such as an enzymatic, fluorescent, isotopic or affinity label to allow for detection and isolation of the mutant EGFr polypeptide.

In certain embodiments, a mutant PI3K polypeptide may be modified at random positions within the molecule, or at predetermined positions within the molecule and may include one, two, three or more attached chemical moieties. In certain embodiments, a mutant PI3K polypeptide may also be modified at pre-determined positions in the polypeptide, such as at the amino terminus, or at a selected lysine or arginine residue within the polypeptide. Other chemical modifications include, but are not limited to, a detectable label, such as an enzymatic, fluorescent, isotopic or affinity label to allow for detection and isolation of the mutant PI3K polypeptide.

In certain embodiments, a mutant B-Raf polypeptide may be modified at random positions within the molecule, or at predetermined positions within the molecule and may include one, two, three or more attached chemical moieties. In certain embodiments, a mutant B-Raf polypeptide may also be modified at pre-determined positions in the polypeptide, such as at the amino terminus, or at a selected lysine or arginine residue within the polypeptide. Other chemical modifications include, but are not limited to, a detectable label, such as an enzymatic, fluorescent, isotopic or affinity label to allow for detection and isolation of the mutant B-Raf polypeptide.

In certain embodiments, a mutant EGFr fusion protein is provided. In certain embodiments, a mutant EGFr polypeptide may be fused to a homologous polypeptide to form a homodimer or to a heterologous polypeptide to form a heterodimer. Exemplary heterologous polypeptides and peptides include, but are not limited to: an epitope to allow for the detection and/or isolation of the fusion protein; a transmembrane receptor protein or a portion thereof, such as an extracellular domain, a transmembrane domain, or an intracellular domain; a ligand or a portion thereof which binds to a transmembrane receptor protein; an enzyme or portion thereof which is catalytically active; a polypeptide which promotes oligomerization, including, but not limited to a leucine zipper domain; a polypeptide which increases the stability of the fusion protein, including, but not limited to, an immunoglobulin constant region; and a polypeptide which has a therapeutic activity different from the mutant EGFr polypeptide. In certain embodiments, a mutant EGFr polypeptide or mutant EGFr fusion protein may be linked to an N-terminal methionine, which may be useful to allow expression in prokaryotic cells such as *E. coli.*

In certain embodiments, a mutant PI3K fusion protein is provided. In certain embodiments, a mutant PI3K polypeptide may be fused to a homologous polypeptide to form a homodimer or to a heterologous polypeptide to form a heterodimer. Exemplary heterologous polypeptides and peptides include, but are not limited to: an epitope to allow for the detection and/or isolation of the fusion protein; a transmembrane receptor protein or a portion thereof, such as an extracellular domain, a transmembrane domain, or an intracellular domain; a ligand or a portion thereof which binds to a transmembrane receptor protein; an enzyme or portion thereof which is catalytically active; a polypeptide which promotes oligomerization, including, but not limited to a leucine zipper domain; a polypeptide which increases the stability of the fusion protein, including, but not limited to, an immunoglobulin constant region; and a polypeptide which has a therapeutic activity different from the mutant PI3K polypeptide. In certain embodiments, a mutant PI3K polypeptide or mutant PI3K fusion protein may be linked to an N-terminal methionine, which may be useful to allow expression in prokaryotic cells such as *E. coli.*

In certain embodiments, a mutant B-Raf fusion protein is provided. In certain embodiments, a mutant B-Raf polypeptide may be fused to a homologous polypeptide to form a homodimer or to a heterologous polypeptide to form a heterodimer. Exemplary heterologous polypeptides and peptides include, but are not limited to: an epitope to allow for the detection and/or isolation of a mutant B-Raf fusion protein; a transmembrane receptor protein or a portion thereof, such as an extracellular domain, a transmembrane domain, or an intracellular domain; a ligand or a portion thereof which binds to a transmembrane receptor protein; an enzyme or portion thereof which is catalytically active; a polypeptide which promotes oligomerization, including, but not limited to a leucine zipper domain; a polypeptide which increases the stability of the fusion protein, including, but not limited to, an immunoglobulin constant region; and a polypeptide which has a therapeutic activity different from the mutant B-Raf polypeptide. In certain embodiments, a mutant B-Raf polypeptide or mutant B-Raf fusion protein may be linked to an N-terminal methionine, which may be useful to allow expression in prokaryotic cells such as *E. coli.*

In certain embodiments, a heterologous or homologous polypeptide is fused to the amino-terminus of a mutant EGFr polypeptide. In certain embodiments, a heterologous or homologous polypeptide is fused to carboxy-terminus of a mutant EGFr polypeptide. In certain embodiments, one or more heterologous or homologous polypeptides or peptides is fused to both the amino- and the carboxy-termini of a mutant EGFr polypeptide. In certain embodiments, a polypeptide is fused directly to a mutant EGFr polypeptide. In certain embodiments, a polypeptide is fused to a mutant EGFr polypeptide via a linker or adapter molecule, as is known in the art. In certain such embodiments, the linker or adapter molecule is designed to contain a cleavage site for a protease to allow for the separation of the fused polypeptides.

In certain embodiments, a heterologous or homologous polypeptide is fused to the amino-terminus of a mutant PI3K polypeptide. In certain embodiments, a heterologous or homologous polypeptide is fused to carboxy-terminus of a mutant PI3K polypeptide. In certain embodiments, one or more heterologous or homologous polypeptides or peptides is fused to both the amino- and the carboxy-termini of a mutant PI3K polypeptide. In certain embodiments, a polypeptide is fused directly to a mutant PI3K polypeptide. In certain embodiments, a polypeptide is fused to a mutant PI3K polypeptide via a linker or adapter molecule, as is known in the art. In certain such embodiments, the linker or adapter molecule is designed to contain a cleavage site for a protease to allow for the separation of the fused polypeptides.

In certain embodiments, a heterologous or homologous polypeptide is fused to the amino-terminus of a mutant B-Raf polypeptide. In certain embodiments, a heterologous or homologous polypeptide is fused to carboxy-terminus of a mutant B-Raf polypeptide. In certain embodiments, one or more heterologous or homologous polypeptides are fused to both the amino- and the carboxy-termini of a mutant B-Raf polypeptide. In certain embodiments, a polypeptide is fused directly to a mutant B-Raf polypeptide. In certain embodiments, a polypeptide is fused to a mutant B-Raf polypeptide via a linker or adapter molecule, as is known in the art. In certain such embodiments, the linker or adapter molecule is designed to contain a cleavage site for a protease to allow for the separation of the fused polypeptides.

Vectors, Host Cells, Transgenic Animals, and Protein Production and Purification In certain embodiments, a vector comprising at least one polynucleotide encoding a mutant EGFr polypeptide is provided. In certain such embodiments, the mutant EGFr polypeptide comprises at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. In certain embodiments, mutant EGFr polypeptide comprises at least one EGFr mutation selected from: L688P, Q701H, K745N, C781R, a histidine insertion between amino acids 771 and 772, T790M, L828stop, Q849R, F910L, and V948A. In certain embodiments, the vector is an expression vector.

In certain embodiments, a vector comprising at least one polynucleotide encoding a mutant PI3K polypeptide is provided. In certain such embodiments, the mutant PI3K polypeptide comprises at least one amino acid sequence selected from SEQ ID NO: 15, SEQ ID NO: 16, and SEQ ID NO: 17. In certain embodiments, a mutant PI3K polypeptide comprises at least one PI3K mutation selected from: E542K, E545A, and H1047L. In certain embodiments, the vector is an expression vector.

In certain embodiments, a vector comprising at least one polynucleotide encoding a mutant B-Raf polypeptide is provided. In certain such embodiments, the mutant B-Raf polypeptide comprises an amino acid sequence selected from SEQ ID NO: 19 and SEQ ID NO: 20. In certain embodiments, a mutant B-Raf polypeptide comprises at least one B-Raf mutation selected from: V600E and K601E. In certain embodiments, the vector is an expression vector.

In certain embodiments, the expression vector may contain a promoter that is recognized by the host organism and operably linked to a nucleic acid molecule encoding a mutant EGFr. In certain embodiments, a native or heterologous promoter may be used depending on the host cell used for expression and the yield of protein desired.

Exemplary promoters for use with prokaryotic hosts include, but are not limited to, beta-lactamase and lactose promoter systems; alkaline phosphatase; a tryptophan (trp) promoter system; and hybrid promoters such as the tac promoter. In certain embodiments, other known bacterial promoters may be used. The sequences of known bacterial promoters have been published, thereby enabling one skilled in the art to ligate them to the desired nucleic acid sequence(s), using linkers or adapters as needed to supply any desired restriction sites.

Suitable promoters for use with yeast hosts are also well known in the art. In certain embodiments, yeast enhancers are advantageously used with yeast promoters. Suitable promoters for use with mammalian host cells are well known. Exemplary promoters for use with mammalian host cells include, but are not limited to, those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Exemplary mammalian promoters include, but are not limited to, heterologous mammalian promoters. Exemplary heterologous mammalian promoters include, but are not limited to, heat-shock promoters and the actin promoter.

Exemplary promoters which may be used for expressing mutant EGFr polynucleotides include, but are not limited to, the SV40 early promoter region (Benoist and Chambon (1981), *Nature,* 290:304-310); the CMV promoter; the promoter contained in the 3' long terminal repeat of Rous sarcoma virus (Yamamoto et al. (1980), *Cell,* 22: 787-97); the herpes thymidine kinase promoter (Wagner et al. (1981), *Proc. Natl. Acad. Sci. U.S.A.,* 78: 1444-5); the regulatory sequences of the metallothionine gene (Brinster et al. (1982), Nature, 296: 39-42); prokaryotic expression vectors such as the beta-lactamase promoter (Villa-Kamaroff et al. (1978), *Proc. Natl. Acad. Sci. U.S.A.,* 75: 3727-31); and the tac promoter (DeBoer, et al. (1983), *Proc. Natl. Acad. Sci. U.S.A.,* 80: 21-25).

In certain embodiments, an enhancer sequence may be included in a vector to increase transcription in eukaryotic host cells. Exemplary enhancer sequences from mammalian genes include, but are not limited to, globin, elastase, albumin, alpha-feto-protein, and insulin. In certain embodiments, an enhancer from a virus is used. Exemplary enhancer sequences for the activation of eukaryotic promoters include, but are not limited to, the SV40 enhancer, the cytomegalovirus early promoter enhancer, the polyoma enhancer, and adenovirus enhancers. In certain embodiments, an enhancer may be spliced into the vector at a position 5' or 3' to the polypeptide coding region. In certain embodiments, the enhancer is located at a site 5' from the promoter. In certain embodiments, the enhancer is located at a site 3' from the end of the polypeptide coding region.

In certain embodiments, vectors are those which are compatible with at least one of bacterial, insect, and mammalian host cells. Exemplary vectors include, but are not limited to, pCRII, pCR3, and pcDNA3.1 (Invitrogen Company, San Diego, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publication No. WO90/14363) and pFastBacDual (Gibco/BRL, Grand Island, N.Y.).

Exemplary vectors include, but are not limited to, cosmids, plasmids and modified viruses compatible with the selected host cell. In certain embodiments, the vectors may include plasmids including, but not limited to, Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.). In certain embodiments, the recombinant molecules may be introduced into host cells via transformation, transfection, infection, electroporation, or other known techniques.

The term "transfection" refers to the taking up of an expression vector by a host cell whether or not any coding sequences are in fact expressed. Numerous methods of transfection are known to the ordinarily skilled artisan, including, but not limited to, $CaPO_4$ precipitation and electroporation. In certain embodiments, successful transfection is recognized when any indication of the operation of the transfected vector occurs within the host cell.

In certain embodiments, host cells may be prokaryotic host cells (such as *E. coli*) or eukaryotic host cells (such as a yeast cell, an insect cell, or a vertebrate cell). In certain embodiments, prokaryotic host cells such as *E. coli* produce unglycosylated protein; for example, unglyclosylated shBCMA and unglycosylated shTACI, which may possess advantages over the glycosylated eukaryotic molecules. In certain embodiments, a host cell, when cultured under appropriate conditions, expresses a polypeptide of the invention which can subsequently be collected from the culture medium (if the host cell secretes it into the medium) or directly from the host cell producing it (if it is not secreted). In certain embodiments, selection of an appropriate host cell will take into account various factors, such as desired expression levels, polypeptide modifications that are desirable or necessary for activity, such as glycosylation or phosphorylation, and/or ease of folding into a biologically active molecule.

A number of suitable host cells are known in the art and many are available from the American Type Culture Collection (ATCC), Manassas, Va. Exemplary host cells include, but are not limited to, mammalian cells, such as Chinese hamster ovary cells (CHO) (ATCC No. CCL61) CHO DHFR-cells (Urlaub et al. (1980), *Proc. Natl. Acad. Sci. USA* 97, 4216-20), human embryonic kidney (HEK) 293 or 293T cells (ATCC No. CRL1573), and 3T3 cells (ATCC No. CCL92). The selection of suitable mammalian host cells and methods for transformation, culture, amplification, screening and product production and purification are known in the art. Exemplary host cells include, but are not limited to, the monkey COS-1 (ATCC No. CRL1650) and COS-7 cell lines (ATCC No. CRL1651), and the CV-1 cell line (ATCC No. CCL70). Exemplary mammalian host cells include, but are not limited to, primate cell lines and rodent cell lines, including transformed cell lines. Exemplary host cells include, but are not limited to, normal diploid cells, cell strains derived from in vitro culture of primary tissue, stem cell lines, and primary explants. In certain embodiments, candidate cells may be genotypically deficient in the selection gene, or may contain a dominantly acting selection gene. Exemplary host cells include, but are not limited to, mouse neuroblastoma N2A cells, HeLa, mouse L-929 cells, 3T3 lines derived from Swiss, Balb-c or NIH mice, BHK or HaK hamster cell lines, which are available from the American Type Culture Collection, Manassas, Va.). Each of these cell lines is known by and available to those skilled in the art of protein expression.

In certain embodiments, host cells may be bacterial cells. Exemplary bacterial host cells include, but are not limited to, various strains of *E. coli* (e.g., HB101, (ATCC No. 33694) DH5a, DH10, and MC1061 (ATCC No. 53338)). Exemplary host cells also include, but are not limited to, various strains of *Pseudomonas* spp., *B. subtilis*, other *Bacillus* spp., and *Streptomyces* spp.

Many strains of yeast cells known to those skilled in the art are also available as host cells for expression of polypeptides. Certain such embodiments use commercially available expression systems, e.g., the *Pichia* Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol. In certain embodiments, the host cell may be *Saccharomyces cerivisae.*

In certain embodiments, plant cell systems may be used as host cells. In certain such embodiments, plant cell systems transfected with virus expression vectors (e.g., cauliflower mosaic virus, CaMV, or tobacco mosaic virus) are used.

In certain embodiments, a polynucleotide encoding a mutant EGFr polypeptide, a mutant PI3K polypeptide, and/or a mutant B-Raf polypeptide is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a mutant EGFr polypeptide, a mutant PI3K polypeptide, and/or a mutant B-Raf polypeptide is purified and concentrated from such media using a heparin-Sepharose column (Pharmacia).

In certain embodiments, insect cell systems may be used as host cells. Certain such systems are described, for example, in Kitts et al. (1993), *Biotechniques,* 14: 810-7, Lucklow (1993), *Curr. Opin. Biotechnol.,* 4: 564-72, and Lucklow et al. (1993), *J. Virol.,* 67: 4566-79. Exemplary insect cells include, but are not limited to, Sf-9 and Hi5 (Invitrogen, Carlsbad, Calif.).

In certain embodiments, transformation or transfection of a polynucleotide encoding a mutant EGFr polypeptide, a mutant PI3K polypeptide, and/or a mutant B-Raf polypeptide into a selected host cell may be accomplished by well known methods including methods such as calcium chloride, electroporation, microinjection, lipofection or the DEAE-dextran method. In certain embodiments, the method selected will in part be a function of the type of host cell to be used. These methods and other suitable methods are well known to the skilled artisan, and are set forth, for example, in Sambrook et al. Molecular Cloning: A Laboratory Manual (2d ed., Cold Spring Harbor Laboratory Press, Cold Spring Harbor, N.Y. (1989)).

Host cells comprising (as by transformation or transfection) an expression vector encoding a mutant EGFr polypeptide, a mutant PI3K polypeptide, and/or a mutant B-Raf polypeptide may be cultured using standard media well known to the skilled artisan. In certain embodiments, the media may contain all nutrients necessary for the growth and survival of the cells. In certain embodiments, *E. coli* cells may be cultured in Luria Broth (LB) and/or Terrific Broth (TB). Exemplary media for culturing eukaryotic cells include, but are not limited to, RPMI 1640, MEM, DMEM, all of which may be supplemented with serum and/or growth factors according to the particular cell line being cultured. In certain embodiments, insect cells may be cultured in Grace's medium supplemented with yeastolate, lactalbumin hydrolysate, and/or fetal calf serum.

In certain embodiments, an antibiotic or other compound useful for selective growth of transfected or transformed cells is added as a supplement to the media. In certain embodiments, the compound to be used is chosen in view of the selectable marker element present on the plasmid with which the host cell was transformed. In certain embodiments, where the selectable marker element is kanamycin resistance, the compound added to the culture medium will be kanamycin. Exemplary compounds for selective growth include, but are not limited to, ampicillin, tetracycline and neomycin.

In certain embodiments, the amount of a mutant EGFr polypeptide, a mutant PI3K polypeptide, and/or a mutant B-Raf polypeptide produced by a host cell can be evaluated using standard methods known in the art. Exemplary methods include, but are not limited to, Western blot analysis, SDS-polyacrylamide gel electrophoresis, non-denaturing gel electrophoresis, HPLC separation, immunoprecipitation, and activity assays.

In certain embodiments, mutant EGFr polypeptides, mutant PI3K polypeptides, and/or mutant B-Raf polypeptides which are expressed in procaryotic host cells may be present in soluble form either in the periplasmic space or in the cytoplasm or in an insoluble form as part of intracellular inclusion bodies. In certain embodiments, mutant EGFr polypeptides, mutant PI3K polypeptides, and/or mutant B-Raf polypeptides can be extracted from the host cell using any standard technique known to the skilled artisan. In certain embodiments, the host cells can be lysed to release the contents of the periplasm/cytoplasm by French press, homogenization, and/or sonication followed by centrifugation.

In certain embodiments, soluble forms of mutant EGFr polypeptides, mutant PI3K polypeptides, and/or mutant B-Raf polypeptides present either in the cytoplasm or released from the periplasmic space may be further purified using methods known in the art. In certain embodiments, mutant EGFr polypeptides, mutant PI3K polypeptides, and/or mutant B-Raf polypeptides are released from the bacterial periplasmic space by osmotic shock techniques.

If a mutant EGFr polypeptide, a mutant PI3K polypeptide, and/or a mutant B-Raf polypeptide has formed inclusion bodies, they may often bind to the inner and/or outer cellular membranes and thus will be found primarily in the pellet material after centrifugation. In certain embodiments, the pellet material may then be treated at pH extremes or with a chaotropic partner such as a detergent, guanidine, guanidine derivatives, urea, or urea derivatives in the presence of a reducing partner such as dithiothreitol at alkaline pH or tris carboxyethyl phosphine at acid pH to release, break apart, and solubilize the inclusion bodies. In certain embodiments, the mutant EGFr polypeptide, the mutant PI3K polypeptide, and/or the mutant B-Raf polypeptide may then be analyzed using gel electrophoresis, immunoprecipitation or the like. In certain embodiments, a mutant EGFr polypeptide, a mutant PI3K polypeptide, and/or a mutant B-Raf polypeptide may be isolated using standard methods such as those set forth below and in Marston et al. (1990), *Meth. Enz.,* 182: 264-75.

In certain embodiments, a mutant EGFr polypeptide, a mutant PI3K polypeptide, and/or a mutant B-Raf polypeptide may not be biologically active upon isolation. In certain embodiments, methods for "refolding" or converting the polypeptide to its tertiary structure and generating disulfide linkages, may be used to restore biological activity. In certain embodiments, the biological activity may be restored by exposing the solubilized polypeptide to a pH usually above 7 in the presence of a particular concentration of a chaotrope. The selection of chaotrope is very similar to the choices used for inclusion body solubilization, but, in certain embodiments, the chaotrope is used at a lower concentration and is not necessarily the same as chaotropes used for the solubilization. In certain embodiments, the refolding/oxidation solution will also contain a reducing partner or the reducing partner plus its oxidized form in a specific ratio to generate a particular redox potential allowing for disulfide shuffling to occur in the formation of the protein's cysteine bridge(s). Exemplary redox couples include, but are not limited to, cysteine/cystamine, glutathione (GSH)/dithiobis GSH, cupric chloride, dithiothreitol (DTT)/dithiane DTT, and 2-mercaptoethanol (bME)/dithio-b (ME). In certain embodiments, a cosolvent may be used or may be needed to increase the efficiency of the refolding and exemplary repartners used for this purpose include, but are not limited to, glycerol, polyethylene glycol of various molecular weights, arginine, and related molecules.

In certain embodiments, mutant EGFr polypeptides, mutant PI3K polypeptides, and/or mutant B-Raf polypeptides may be prepared by chemical synthesis methods. In certain embodiments, the chemical synthesis method may incorporate solid phase peptide synthesis. In certain embodiments, the chemical synthesis methods may use techniques known in the art such as those set forth by Merrifield et al. (1963), *J. Am. Chem. Soc.,* 85: 2149; Houghten et al. (1985), *Proc Natl Acad. Sci. USA,* 82: 5132; and Stewart and Young (1984), *Solid Phase Peptide Synthesis*, Pierce Chemical Co., Rockford, Ill. In certain embodiments, polypeptides may be synthesized with or without a methionine on the amino terminus. In certain embodiments, chemically synthesized mutant EGFr polypeptides, mutant PI3K polypeptides, and/or mutant B-Raf polypeptides may be oxidized using methods set forth in these references to form disulfide bridges. In certain embodiments, mutant EGFr polypeptides, mutant PI3K polypeptides, and/or mutant B-Raf polypeptides so prepared will retain at least one biological activity associated with a native or recombinantly produced mutant EGFr polypeptide, mutant PI3K polypeptide, and/or mutant B-Raf polypeptide.

In certain embodiments, transgenic animals may be used to express mutant EGFr polypeptides, mutant PI3K polypeptides, and/or mutant B-Raf polypeptides. In certain embodiments, one may use a transgenic milk-producing animal (a cow or goat, for example) and obtain a glycosylated mutant EGFr polypeptide, a glycosylated mutant PI3K polypeptide, and/or a glycosylated mutant B-Raf polypeptide in the animal milk. In certain embodiments, plants are used to produce a glycosylated mutant EGFr polypeptide, a glycosylated mutant PI3K polypeptide, and/or a glycosylated mutant B-Raf polypeptide, as is known in the art.

In certain embodiments, one substantially purifies a mutant EGFr polypeptide. In certain embodiments, one substantially purifies a mutant PI3K polypeptide. In certain embodiments, one substantially purifies a mutant B-Raf polypeptide. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxylapatite chromatography; isoelectric focusing; polyacrylamide gel electrophoresis; and combinations of such and other techniques. In certain embodiments, a polypeptide is purified by fast protein liquid chromatography or by high pressure liquid chromotography (HPLC). In certain embodiments, purification steps may be changed or certain steps may be omitted, and still result in a suitable method for the preparation of a substantially purified polypeptide.

In certain embodiments, a mutant EGFr polypeptide, a mutant PI3K polypeptide, and/or a mutant B-Raf polypeptide may be prepared with one or more affinity tags, such as hexahistidine or other small peptide such as FLAG (Eastman Kodak Co., New Haven, Conn.) or myc (Invitrogen) at either the carboxyl or amino terminus and purified by a one-step affinity column. In certain embodiments, polyhistidine binds with great affinity and specificity to nickel, thus an affinity column of nickel (such as the Qiagen® nickel columns) can be used for purification of polyhistidine-tagged specific binding partners. See for example, Ausubel et al., eds. (1993), Current Protocols in Molecular Biology, Section 10.11.8, John Wiley & Sons, New York. In certain embodiments, more than one purification step may be used.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide is partially purified. In certain embodiments, partial purification may be accomplished by using fewer purification steps or by utilizing different forms of the same general purification scheme. For example, in certain embodiments, a cation-exchange column chromatography performed utilizing an HPLC apparatus will generally result in a greater "fold purification" than the same technique utilizing a low-pressure chromatography system. In certain embodiments, methods resulting in a lower degree of purification may have advantages in total recovery of polypeptide, or in maintaining binding activity of a polypeptide.

In certain instances, the electrophoretic migration of a polypeptide can vary, sometimes significantly, with different conditions of SDS/PAGE. See, e.g., Capaldi et al., *Biochem Biophys/Res Comm,* 76: 425 (1977). It will be appreciated that under different electrophoresis conditions, the apparent molecular weights of purified or partially purified polypeptide may be different.

Transgenic Animals

In certain embodiments, transgenic non-human animals comprising one or more polynucleotides encoding one or more mutant EGFr polypeptides, one or more mutant PI3K polypeptides, and/or one or more mutant B-Raf polypeptides are provided. In certain embodiments, non-human transgenic animals include, but are not limited to, rodents such as mice or rats, rabbits, goats, sheep, and other farm animals. Certain transgenic animals may be prepared using well known methods including, but not limited to, those described in U.S. Pat. No. 5,489,743 and in WO 94/28122.

In certain embodiments, animal transcriptional control regions which exhibit tissue specificity may be used to construct transgenic animals. Exemplary transcriptional control regions for use with tissue specific expression in transgenic animals include, but are not limited to, the elastase I gene control region which is active in pancreatic acinar cells (Swift et al. (1984), *Cell,* 38: 639-46; Ornitz et al. (1986), Cold Spring Harbor Symp. Quant. Biol. 50: 399-409; MacDonald (1987), *Hepatology,* 7:425-515); the insulin gene control region which is active in pancreatic beta cells (Hanahan (1985), *Nature,* 315: 115-122); the immunoglobulin gene control region which is active in lymphoid cells (Grosschedl et al. (1984), *Cell,* 38: 647-58; Adames et al. (1985), *Nature,* 318: 533-8; Alexander et al. (1987), *Mol. Cell. Biol.,* 7: 1436-44); the mouse mammary tumor virus control region which is active in testicular, breast, lymphoid and mast cells (Leder et al. (1986), *Cell,* 45: 485-95); albumin gene control region which is active in liver (Pinkert et al. (1987), *Genes and Devel.,* 1: 268-76); the alphafetoprotein gene control region which is active in liver (Krumlauf et al. (1987), *Mol. Cell. Biol.,* 5: 1639-48; Hammer et al. (1987), *Science,* 235: 53-58); the alpha 1-antitrypsin gene control region which is active in the liver (Kelsey et al. (1987), *Genes and Devel.,* 1: 161-171); the beta-globin gene control region which is active in myeloid cells (Mogram et al. (1985), *Nature,* 315: 338-340; Kollias et al. (1986), *Cell,* 46: 89-94); the myelin basic protein gene control region which is active in oligodendrocyte cells in the brain (Readhead et al. (1987), *Cell,* 48: 703-712); the myosin light chain-2 gene control region which is active in skeletal muscle (Sani (1985), *Nature,* 314: 283-286); and the gonadotropic releasing hormone gene control region which is active in the hypothalamus (Mason et al. (1986), *Science,* 234: 1372-8).

In certain embodiments, a non-human animal is provided in which a polynucleotide encoding a wild-type EGFr polypeptide has been disrupted (i.e., "knocked out") and replaced with one or more polynucleotides encoding a mutant EGFr polypeptide such that the level of expression of wild-type EGFr polypeptide is significantly decreased or completely abolished in the animal and the mutant EGFr polypeptide is expressed in the animal. In certain such embodiments, the animals may be prepared using techniques and methods such as those described in U.S. Pat. No. 5,557,032 or other techniques well known in the art. In certain embodiments, a non-human animal is provided in which the activity of the promoter for one or more mutant EGFr polypeptides is modulated (e.g., by using homologous recombination methods known in the art) to alter the level of expression of one or more mutant EGFr polypeptides. In certain such embodiments, the level of expression of a mutant EGFr polypeptide is increased. In certain such embodiments, the level of expression of the mutant EGFr polypeptide is decreased.

In certain embodiments, a non-human animal is provided in which a polynucleotide encoding a wild-type PI3K polypeptide has been disrupted (i.e., "knocked out") and replaced with one or more polynucleotides encoding a mutant PI3K polypeptide such that the level of expression of wild-type PI3K polypeptide is significantly decreased or completely abolished in the animal and the mutant PI3K polypeptide is expressed in the animal. In certain such embodiments, the animals may be prepared using techniques and methods such as those described in U.S. Pat. No. 5,557,032 or other techniques well known in the art. In certain embodiments, a non-human animal is provided in which the activity of the promoter for one or more mutant PI3K polypeptides ismodulated (e.g., by using homologous recombination methods known in the art) to alter the level of expression of one or more mutant PI3K polypeptides. In certain such embodiments, the level of expression of the mutant PI3K polypeptide is increased. In certain such embodiments, the level of expression of the mutant PI3K polypeptide is decreased.

In certain embodiments, a non-human animal is provided in which a polynucleotide encoding a wild-type B-Raf polypeptide have been disrupted (i.e., "knocked out") and replaced with one or more polynucleotides encoding a mutant B-Raf polypeptide such that the level of expression of wild-type B-Raf polypeptide is significantly decreased or completely abolished in the animal and the mutant B-Raf polypeptide is expressed in the animal. In certain such embodiments, the animals may be prepared using techniques and methods such as those described in U.S. Pat. No. 5,557,032 or other techniques well known in the art. In certain embodiments, a non-human animal is provided in which the activity of the promoter for one or more mutant B-Raf polypeptides is modulated (e.g., by using homologous recombination methods known in the art) to alter the level of expression of one or more mutant B-Raf polypeptides. In certain such embodiments, the level of expression of the mutant B-Raf polypeptide is increased. In certain such embodiments, the level of expression of the mutant B-Raf polypeptide is decreased.

In certain embodiments, a non-human transgenic animal can be used for drug candidate screening. In certain embodiments, the impact of a drug candidate on the non-human transgenic animal is measured. In certain embodiments, the ability of a drug candidate to increase the expression of a mutant EGFr polypeptide is measured. In certain embodiments, the ability of a drug candidate to decrease or prevent the expression of a mutant EGFr polypeptide is measured. In certain embodiments, the ability of a drug candidate to increase the activity of a mutant EGFr polypeptide is measured. In certain embodiments, the ability of a drug candidate to decrease or prevent the activity of a mutant EGFr polypeptide is measured. In certain embodiments, the ability of a drug candidate to decrease or prevent activation of a mutant EGFr polypeptide is measured. In certain embodiments, the ability of a drug candidate to increase activation of a mutant EGFr polypeptide is measured. In certain embodiments, the ability of a drug candidate to decrease or prevent autophosphorylation of a mutant EGFr polypeptide is measured. In certain embodiments, the ability of a drug candidate to increase autophosphorylation of a mutant EGFr polypeptide is measured.

In certain embodiments, the ability of a drug candidate to decrease or prevent binding of one or more specific binding agents to a mutant EGFr polypeptide is measured. In certain embodiments, the ability of a drug candidate to increase binding of one or more specific binding agents to a mutant EGFr polypeptide is measured. In certain embodiments, the ability of a drug candidate to ameliorate a disease or condition related to mutant EGFr polypeptide is measured. In certain embodiments, the ability of a drug candidate to ameliorate a mutant EGFr polypeptide-related cancer is measured.

In certain embodiments, the ability of a drug candidate to increase the expression of a mutant PI3K polypeptide is measured. In certain embodiments, the ability of a drug candidate to decrease or prevent the expression of a mutant PI3K polypeptide is measured. In certain embodiments, the ability of a drug candidate to increase the activity of a mutant PI3K polypeptide is measured. In certain embodiments, the ability of a drug candidate to decrease or prevent the activity of a mutant PI3K polypeptide is measured. In certain embodiments, the ability of a drug candidate to decrease or prevent activation of a mutant PI3K polypeptide is measured. In certain embodiments, the ability of a drug candidate to increase activation of a mutant PI3K polypeptide is measured. In certain embodiments, the ability of a drug candidate to decrease or prevent autophosphorylation of a mutant PI3K polypeptide is measured. In certain embodiments, the ability of a drug candidate to increase autophosphorylation of a mutant PI3K polypeptide is measured.

In certain embodiments, the ability of a drug candidate to decrease or prevent binding of one or more specific binding agents to a mutant PI3K polypeptide is measured. In certain embodiments, the ability of a drug candidate to increase binding of one or more specific binding agents to a mutant PI3K polypeptide is measured. In certain embodiments, the ability of a drug candidate to ameliorate a disease or condition related to mutant PI3K polypeptide is measured. In certain embodiments, the ability of a drug candidate to ameliorate a mutant PI3K polypeptide-related cancer is measured.

In certain embodiments, the ability of a drug candidate to increase the expression of a mutant B-Raf polypeptide is measured. In certain embodiments, the ability of a drug candidate to decrease or prevent the expression of a mutant B-Raf polypeptide is measured. In certain embodiments, the ability of a drug candidate to increase the activity of a mutant B-Raf polypeptide is measured. In certain embodiments, the ability of a drug candidate to decrease or prevent the activity of a mutant B-Raf polypeptide is measured. In certain embodiments, the ability of a drug candidate to decrease or prevent activation of a mutant B-Raf polypeptide is measured. In certain embodiments, the ability of a drug candidate to increase activation of a mutant B-Raf polypeptide is measured. In certain embodiments, the ability of a drug candidate to decrease or prevent autophosphorylation of a mutant B-Raf polypeptide is measured. In certain embodiments, the ability of a drug candidate to increase autophosphorylation of a mutant B-Raf polypeptide is measured.

In certain embodiments, the ability of a drug candidate to decrease or prevent binding of one or more specific binding agents to a mutant B-Raf polypeptide is measured. In certain embodiments, the ability of a drug candidate to increase binding of one or more specific binding agents to a mutant B-Raf polypeptide is measured. In certain such embodiments, the ability of a drug candidate to ameliorate a disease or condition related to mutant B-Raf polypeptide is measured. In certain embodiments, the ability of a drug candidate to ameliorate a mutant B-Raf polypeptide-related cancer is measured.

Specific Binding Agents and Antibodies

In certain embodiments, a specific binding agent to a mutant EGFr polypeptide is provided. In certain embodiments, a specific binding agent to a mutant PI3K polypeptide is provided. In certain embodiments, a specific binding agent to a mutant B-Raf polypeptide is provided. In certain such embodiments, the specific binding agents are antibodies or antigen-binding fragments thereof.

In certain embodiments, monoclonal antibodies may be made using the hybridoma method first described by Kohler et al., *Nature* 256: 495 (1975). In certain embodiments, monoclonal antibodies may be made by recombinant DNA methods (U.S. Pat. No. 4,816,567).

In certain embodiments of the hybridoma method, a mouse or other appropriate host animal, including, but not limited to, a hamster or macaque monkey, is immunized to elicit lymphocytes that produce or are capable of producing antibodies that will specifically bind to the protein used for immunization. In certain embodiments, lymphocytes may be immunized in vitro. In certain embodiments, lymphocytes or lymphocytes enriched for B cells are fused with myeloma cells by an electrocell fusion process or by using a suitable fusing agent, such as polyethylene glycol, to form a hybridoma cell (Goding, *Monoclonal Antibodies: Principles and Practice*, pp. 59-103, [Academic Press, 1996]).

In certain embodiments, hybridoma cells are seeded and grown in a suitable culture medium that preferably contains one or more substances that inhibit the growth or survival of the unfused, parental myeloma cells. In certain embodiments, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In certain embodiments, myeloma cells are selected that fuse efficiently, support stable high-level production of antibody by the selected antibody-producing cells, and are sensitive to a medium such as HAT medium. Exemplary myeloma cell lines include, but are not limited to, murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. In certain embodiments, human myeloma and/or mouse-human heteromyeloma cell lines are used for the production of human monoclonal antibodies (Kozbor, *J. Immunol.* 133: 3001 (1984); Brodeur et al., *Monoclonal Antibody Production Techniques and Applications*, pp. 51-63, Marcel Dekker, Inc., New York, [1987]).

In certain embodiments, culture medium in which hybridoma cells are growing is assayed for production of monoclonal antibodies directed against the antigen. In certain embodiments, the binding specificity of monoclonal antibodies produced by hybridoma cells is determined by immunoprecipitation or by an in vitro binding assay. Exemplary binding assays include, but are not limited to, a radioimmunoassay (RIA), an enzyme-linked immunosorbent assay (ELISA), and the Scatchard analysis of Munson et al., *Anal. Biochem.* 107: 220 (1980).

In certain embodiments, after hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp. 59-103, Academic Press, 1996). Exemplary culture media for this purpose include, but are not limited to, DMEM and RPMI-1640 medium. In certain embodiments, hybridoma cells may be grown in vivo as ascites tumors in an animal.

In certain embodiments, monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In certain embodiments, a polynucleotide encoding the monoclonal antibodies is readily isolated and sequenced using conventional procedures (e.g., by using oligonucleotide probes that are capable of binding specifically to genes encoding the heavy and light chains of the monoclonal antibodies). In certain such embodiments, the hybridoma cells serve as a preferred source of such polynucleotide. In certain embodiments, isolated polynucleotide may be placed into expression vectors. In certain such embodiments, the expression vectors are transfected into host cells to obtain the synthesis of monoclonal antibodies in the recombinant host cells. Exemplary host cells include, but are not limited to, *E. coli* cells, simian COS cells, Chinese hamster ovary (CHO) cells, or myeloma cells that do not otherwise produce immunoglobulin protein. In certain embodiments, the polynucleotide may be modified, for example, by covalently joining to the immunoglobulin coding sequence all or part of the coding sequence for a non-immunoglobulin polypeptide, creating a "chimeric" or "hybrid" antibody.

In certain embodiments, non-immunoglobulin polypeptides are substituted for the constant domains of an antibody. In certain embodiments, non-immunoglobulin polypeptides are substituted for the variable domains of one antigen-combining sites of an antibody to create a chimeric bivalent antibody comprising one antigen-combining site having specificity for a target antigen and another antigen-combining site having specificity for a different antigen.

In certain embodiments, chimeric or hybrid antibodies can be prepared in vitro using known methods in synthetic protein chemistry, including, but not limited to, those involving crosslinking agents. In certain such embodiments, immunotoxins can be constructed using a disulfide exchange reaction or by forming a thioether bond. Exemplary reagents for this purpose include, but are not limited to, iminothiolate and methyl-4-mercaptobutyrimidate.

In certain embodiments, human antibodies to a target antigen are provided. In certain embodiments, hybridoma technology is extended to create human antibodies using heteromyelomas (mouse×human hybrid myelomas) as fusion partners (see, e.g., Kozbor, *J. Immunol.* 133: 3001 (1984); Brodeur, et al., *Monoclonal Antibody Production Techniques and Applications*, pp. 51-63, Marcel Dekker, Inc., New York, 1987). In certain embodiments, human antibody-secreting cells can be immortalized by infection with the Epstein-Barr virus (EBV) (James and Bell, *J. Immunol. Methods* 100: 5-40 [1987]). In certain embodiments, the immortalization of human B cells can be achieved by introducing a defined combination of transforming genes (Hahn et al., *Nature* 400: 464-468 [1999]).

In certain embodiments, transgenic animals (e.g. mice) that are capable, upon immunization, of producing a repertoire of human antibodies in the absence of endogenous immunoglobulin production are used to make human antibodies (see, e.g., Jakobovits et al., *Nature* 362: 255-258 [1993]; Lonberg and Huszar, *Int. Rev. Immunol.* 13: 65-93 [1995]; Fishwild et al., *Nat. Biotechnol.* 14: 845-851 [1996]; Mendez et al., *Nat. Genet.* 15: 146-156 [1997]; Green, *J. Immunol. Methods* 231: 11-23 [1999]; Tomizuka et a *I. Proc. Natl. Acad. Sci. USA* 97: 722-727 [2000]; reviewed in Little et al., *Immunol. Today* 21: 364-370 [2000]). It has been described that the homozygous deletion of the antibody heavy chain joining region ($J_H$) gene in chimeric and germ line mutant mice results in complete inhibition of endogenous antibody production (Jakobovits et al., *Proc. Natl. Acad. Sci. USA* 90: 2551-2555 [1993]). Transfer of the human germ-line immunoglobulin gene array in such germ line mutant mice results in the production of human antibodies upon antigen challenge (Jakobovits et al., *Nature* 362: 255-258 [1993]).

Mendez et al. (*Nature Genetics* 15: 146-156 [1997]) have generated a line of transgenic mice designated as "Xenomouse®II" that, when challenged with an antigen, generates high affinity fully human antibodies. This was achieved by germ-line integration of megabase human heavy chain and light chain loci into mice with deletion into endogenous $J_H$ segment. The XenoMouse® II harbors 1,020 kb of human heavy chain locus containing approximately 66 $V_H$ genes, complete $D_H$ and $J_H$ regions and three different constant regions (μ, δ and γ), and also harbors 800 kb of human κ locus containing 32 Vκ genes, Jκ segments and Cκ genes. In certain embodiments, the antibodies produced in those mice closely resemble those seen in humans in all respects, including gene rearrangement, assembly, and repertoire. In certain embodiments, the human antibodies are preferentially expressed over endogenous antibodies due to a deletion in the endogenous $J_H$ segment that prevents gene rearrangement in the murine locus.

In certain embodiments, a transgenic animal comprising human immunoglobulin genes (e.g., the Xenomouse® II (Abgenix, Inc.)) may be immunized with an antigen of particular interest, such as a mutant EGFr polypeptide, a mutant PI3K polypeptide, and/or a mutant B-Raf polypeptide. In certain embodiments, sera from those immunized animals is screened for antibody reactivity against the initial antigen. In certain embodiments, lymphocytes are isolated from lymph nodes or spleen cells and may further be enriched for B cells by selecting for CD138-negative and CD19+ cells. In certain embodiments, those B cell cultures (BCCs) are fused to myeloma cells to generate hybridomas as detailed above. In certain embodiments, those B cell cultures are screened further for reactivity against the initial antigen. Such screening includes, but is not limited to, ELISA, a competition assay with known antibodies that bind the antigen of interest, and in vitro binding to transiently transfected CHO cells expressing the antigen. In certain embodiments, single B cells secreting antibodies of interest are identified by a specific hemolytic plaque assay. In certain such embodiments, cells targeted for lysis are sheep red blood cells (SRBCs) coated with the antigen. In certain such embodiments, the formation of a plaque indicates specific antigen-mediated lysis of the target cells, and thus the presence of a B cell culture secreting the immunoglobulin of interest and complement. In certain such embodiments, the single antigen-specific plasma cell in the center of the plaque can be isolated and used for isolation of mRNA.

In certain embodiments, the polynucleotide encoding the variable region of the antibody secreted can be cloned using reverse-transcriptase PCR. In certain embodiments, the cloned polynucleotide is further inserted into a suitable expression vector, such as a vector cassette such as a pcDNA, or a pcDNA vector containing the constant domains of immunoglobulin heavy and light chain. In certain embodiments, the generated vector is transfected into host cells, (i.e., CHO cells), and cultured in conventional nutrient media modified as appropriate for inducing promoters, selecting transformants, or amplifying the genes encoding the desired sequences.

In certain embodiments, phage display technology is used to produce human antibodies and antibody fragments in vitro, from immunoglobulin variable (V) domain gene repertoires from unimmunized donors (see, e.g., McCafferty et al., *Nature* 348: 552-553 [1990]; reviewed in Kipriyanov and Little, *Mol. Biotechnol.* 12: 173-201 [1999]; Hoogenboom and Chames, *Immunol. Today* 21: 371-378 [2000]). In certain such embodiments, antibody V domain genes are cloned inframe into either a major or minor coat protein gene of a filamentous bacteriophage, such as M13 or fd, and displayed as functional antibody fragments on the surface of the phage particle. In certain embodiments, the filamentous particle contains a single-stranded DNA copy of the phage genome, and selections based on the functional properties of the antibody also result in selection of the gene encoding the antibody exhibiting those properties. Phage display can be performed in a variety of formats, including, but not limited to, those identified in the following documents: Johnson and Chiswell, *Current Opinion in Structural Biology* 3: 564-571 [1993)]; Winter et al., *Annu. Rev. Immunol.* 12: 433-455 [1994]; Dall'Acqua and Carter, *Curr. Opin. Struct. Biol.* 8: 443-450 [1998]; and Hoogenboom and Chames, *Immunol. Today* 21: 371-378 [2000]. Sources of V-gene segments for phage display include, but are not limited to, a small random combinatorial library of V genes derived from the spleens of immunized mice (Clackson et al., (*Nature* 352: 624-628 [1991]) and a repertoire of V genes from unimmunized human donors (Marks et al., *J. Mol. Biol.* 222: 581-597 (1991), or Griffiths et al., *EMBO J.* 12: 725-734 (1993)).

In certain embodiments, in a natural immune response, antibody genes accumulate mutations at a high rate (somatic hypermutation). In certain embodiments, some of the changes introduced confer higher affinity. In certain embodiments, B cells displaying high-affinity surface immunoglobulin are preferentially replicated and differentiated during subsequent antigen challenge. In certain embodiments, that natural process can be mimicked by employing the technique known as "chain shuffling" (Marks et al., *Bio/Technol.* 10: 779-783 [1992]). In certain such embodiments, the affinity of "primary" human antibodies obtained by phage display can be improved by sequentially replacing the heavy and light chain V region genes with repertoires of naturally occurring variants (repertoires) of V domain genes obtained from unimmunized donors, allowing the production of antibodies and antibody fragments with affinities in the nM range. In certain embodiments, a very large phage antibody repertoire is constructed (also known as "the mother-of-all libraries"), as described by Waterhouse et al., *Nucl. Acids Res.* 21: 2265-2266 (1993). In certain such embodiments, a high affinity human antibody is directly isolated from a large phage library (see, e.g., Griffiths et al., *EMBO J.* 13: 3245-3260 (1994)). In certain embodiments, gene shuffling can be used to derive human antibodies from rodent antibodies, where the human antibody has similar affinities and specificities to the starting rodent antibody. In certain such embodiments, the heavy or light chain V domain gene of rodent antibodies obtained by phage display technique is replaced with a repertoire of human V domain genes, creating rodent-human chimeras (also referred to as "epitope imprinting"). In certain embodiments, selection of variable regions by the antigen results in isolation of human variable regions capable of restoring a functional antigen-binding site, i.e. the epitope governs (imprints) the choice of partner. In certain embodiments, when the process is repeated in order to replace the remaining rodent V domain, a human antibody is obtained which has no framework or CDR residues of rodent origin (see PCT patent application WO 93/06213, published 1 Apr. 1993).

Arrays

In certain embodiments, microarrays comprising one or more polynucleotides encoding one or more mutant EGFr polypeptides are provided. In certain embodiments, microarrays comprising one or more polynucleotides complementary to one or more polynucleotides encoding one or more mutant EGFr polypeptides are provided. In certain embodiments, microarrays comprising one or more polynucleotides encoding one or more mutant PI3K polypeptides are provided. In certain embodiments, microarrays comprising one or more polynucleotides complementary to one or more polynucleotides encoding one or more mutant PI3K polypeptides are provided. In certain embodiments, microarrays comprising one or more polynucleotides encoding one or more mutant B-Raf polypeptides are provided. In certain embodiments, microarrays comprising one or more polynucleotides complementary to one or more polynucleotides encoding one or more mutant B-Raf polypeptides are provided.

In certain embodiments, the presence or absence of one or more mutant EGFr polynucleotides in two or more cell or tissue samples is assessed using microarray technology. In certain embodiments, the quantity of one or more mutant EGFr polynucleotides in two or more cell or tissue samples is assessed using microarray technology. In certain such embodiments, the cell or tissue is treated prior to the assessment, and the ability of the treatment to affect the quantity of the one or more mutant EGFr polynucleotides is also assessed.

In certain embodiments, the presence or absence of one or more mutant PI3K polynucleotides in two or more cell or tissue samples is assessed using microarray technology. In certain embodiments, the quantity of one or more mutant PI3K polynucleotides in two or more cell or tissue samples is assessed using microarray technology. In certain such embodiments, the cell or tissue is treated prior to the assessment, and the ability of the treatment to affect the quantity of the one or more mutant PI3K polynucleotides is also assessed.

In certain embodiments, the presence or absence of one or more mutant B-Raf polynucleotides in two or more cell or tissue samples is assessed using microarray technology. In certain embodiments, the quantity of one or more mutant B-Raf polynucleotides in two or more cell or tissue samples is assessed using microarray technology. In certain such embodiments, the cell or tissue is treated prior to the assessment, and the ability of the treatment to affect the quantity of the one or more mutant B-Raf polynucleotides is also assessed.

In certain embodiments, the presence or absence of one or more mutant EGFr polypeptides in two or more cell or tissue samples is assessed using microarray technology. In certain such embodiments, mRNA is first extracted from a cell or tissue sample and is subsequently converted to cDNA, which is hybridized to the microarray. In certain such embodiments, the presence or absence of cDNA that is specifically bound to the microarray is indicative of the presence or absence of the mutant EGFr polypeptide. In certain such embodiments, the expression level of the one or more mutant EGFr polypeptides is assessed by quantitating the amount of cDNA that is specifically bound to the microarray. In certain such embodiments, the cell or tissue is treated prior to the assessment, and the ability of the treatment to affect expression of the one or more mutant EGFr polypeptides is also assessed.

In certain embodiments, the presence or absence of one or more mutant PI3K polypeptides in two or more cell or tissue samples is assessed using microarray technology. In certain such embodiments, mRNA is first extracted from a cell or tissue sample and is subsequently converted to cDNA, which is hybridized to the microarray. In certain such embodiments, the presence or absence of cDNA that is specifically bound to the microarray is indicative of the presence or absence of the mutant PI3K polypeptide. In certain such embodiments, the expression level of the one or more mutant PI3K polypeptides is assessed by quantitating the amount of cDNA that is specifically bound to the microarray. In certain such embodiments, the cell or tissue is treated prior to the assessment, and the ability of the treatment to affect expression of the one or more mutant PI3K polypeptides is also assessed.

In certain embodiments, the presence or absence of one or more mutant B-Raf polypeptides in two or more cell or tissue samples is assessed using microarray technology. In certain such embodiments, mRNA is first extracted from a cell or tissue sample and is subsequently converted to cDNA, which is hybridized to the microarray. In certain such embodiments, the presence or absence of cDNA that is specifically bound to the microarray is indicative of the presence or absence of the mutant B-Raf polypeptide. In certain such embodiments, the expression level of the one or more mutant B-Raf polypeptides is assessed by quantitating the amount of cDNA that is specifically bound to the microarray. In certain such embodiments, the cell or tissue is treated prior to the assessment, and the ability of the treatment to affect expression of the one or more mutant B-Raf polypeptides is also assessed.

In certain embodiments, microarrays comprising one or more mutant EGFr polypeptides are provided (see, e.g., McBeath et al., Science, 289:1760-1763, 2000). In certain embodiments, candidate specific binding agents to one or more mutant EGFr polypeptides are screened using a mutant EGFr polypeptide microarray. In certain embodiments, candidate compounds for modulating the activity of a mutant EGFr polypeptide are screened using a mutant EGFr polypeptide microarray. In certain such embodiments, the ability of candidate compounds to decrease or prevent autophosphorylation of mutant EGFr polypeptides is assessed. In certain such embodiments, the ability of candidate compounds to increase autophosphorylation of mutant EGFr polypeptides is assessed.

In certain embodiments, microarrays comprising one or more mutant PI3K polypeptides are provided (see, e.g., McBeath et al., Science, 289:1760-1763, 2000). In certain embodiments, candidate specific binding agents to one or more mutant PI3K polypeptides are screened using a mutant PI3K polypeptide microarray. In certain embodiments, candidate compounds for modulating the activity of a mutant PI3K polypeptide are screened using a mutant PI3K polypeptide microarray. In certain such embodiments, the ability of candidate compounds to decrease or prevent autophosphorylation of mutant PI3K polypeptides is assessed. In certain such embodiments, the ability of candidate compounds to increase autophosphorylation of mutant PI3K polypeptides is assessed.

In certain embodiments, microarrays comprising one or more mutant B-Raf polypeptides are provided (see, e.g., McBeath et al., Science, 289:1760-1763, 2000). In certain embodiments, candidate specific binding agents to one or more mutant B-Raf polypeptides are screened using a mutant B-Raf polypeptide microarray. In certain embodiments, candidate compounds for modulating the activity of a mutant B-Raf polypeptide are screened using a mutant B-Raf polypeptide microarray. In certain such embodiments, the ability of candidate compounds to decrease or prevent autophosphorylation of mutant B-Raf polypeptides is assessed. In certain such embodiments, the ability of candidate compounds to increase autophosphorylation of mutant B-Raf polypeptides is assessed.

In certain embodiments, microarrays comprising one or more specific binding agents to one or more mutant EGFr polypeptides are provided. In certain such embodiments, the presence or absence of one or more mutant EGFr polypeptides in a cell or tissue is assessed. In certain such embodiments, the quantity of one or more mutant EGFr polypeptides in a cell or tissue is assessed.

In certain embodiments, microarrays comprising one or more specific binding agents to one or more mutant PI3K polypeptides are provided. In certain such embodiments, the presence or absence of one or more mutant PI3K polypeptides in a cell or tissue is assessed. In certain such embodiments, the quantity of one or more mutant PI3K polypeptides in a cell or tissue is assessed.

In certain embodiments, microarrays comprising one or more specific binding agents to one or more mutant B-Raf polypeptides are provided. In certain such embodiments, the presence or absence of one or more mutant B-Raf polypeptides in a cell or tissue is assessed. In certain such embodiments, the quantity of one or more mutant B-Raf polypeptides in a cell or tissue is assessed.

Certain Methods

In certain embodiments, a method of obtaining an antibody capable of binding at least one mutant EGFr polypeptide is provided. In certain embodiments, a method of obtaining an antibody capable of binding at least one mutant PI3K polypeptide is provided. In certain embodiments, a method of obtaining an antibody capable of binding at least one mutant B-Raf polypeptide is provided. In certain embodiments, a method of obtaining an antibody capable of binding at least one mutant EGFr polypeptide is provided, comprising administering at least one mutant EGFr polypeptide to an animal, and obtaining an antibody capable of binding at least one mutant EGFr polypeptide from the animal. In certain embodiments, a method of obtaining an antibody capable of binding at least one mutant PI3K polypeptide is provided, comprising administering at least one mutant PI3K polypeptide to an animal, and obtaining an antibody capable of binding at least one mutant PI3K polypeptide from the animal. In certain embodiments, a method of obtaining an antibody capable of binding at least one mutant B-Raf polypeptide is provided, comprising administering at least one mutant B-Raf polypeptide to an animal, and obtaining an antibody capable of binding at least one mutant B-Raf polypeptide from the animal. In certain such embodiments, the antibody is a human antibody.

In certain embodiments, a method of obtaining an antibody capable of binding at least one polypeptide comprising at least one amino acid sequence selected from SEQ ID NO: 2, SEQ ID NO:3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 19, and SEQ ID NO: 20 is provided, comprising administering at least one polypeptide comprising at least one sequence selected from SEQ ID NO: 2, SEQ ID NO:3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 19, and SEQ ID NO: 20 to an animal; and obtaining an antibody capable of binding at least one polypeptide comprising at least one amino acid sequence selected from SEQ ID NO: 2, SEQ ID NO:3, SEQ ID NO: 5, SEQ ID NO: 6, SEQ ID NO:

7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 19, and SEQ ID NO: 20 from the animal is provided. In certain such embodiments, the antibody is a human antibody.

In certain embodiments, a method of obtaining an antibody capable of binding at least one polypeptide comprising at least one amino acid sequence selected from SEQ ID NO: 2, SEQ ID NO:3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 19, and SEQ ID NO: 20 is provided, comprising administering at least one fragment of at least one polypeptide comprising at least one sequence selected from SEQ ID NO: 2, SEQ ID NO:3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 19, and SEQ ID NO: 20 to an animal, wherein the at least one fragment comprises at least one mutation; and obtaining an antibody capable of binding at least one polypeptide comprising at least one amino acid sequence selected from SEQ ID NO: 2, SEQ ID NO:3, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, SEQ ID NO: 16, SEQ ID NO: 17, SEQ ID NO: 19, and SEQ ID NO: 20 from the animal is provided. In certain such embodiments, the antibody is a human antibody.

In certain embodiments, a method of diagnosing a disease or condition which is related to one or more EGFr mutations in a subject is provided. In certain embodiments, a method of diagnosing a disease or condition which is related to one or more PI3K mutations in a subject is provided. In certain embodiments, a method of diagnosing a disease or condition which is related to one or more B-Raf mutations in a subject is provided. In certain embodiments, a method of diagnosing a disease or condition which is related to one or more EGFr mutations in a subject comprises: (a) determining the presence or amount of expression of a mutant EGFr polypeptide in a sample from the subject; and (b) diagnosing a disease or condition which is related to one or more EGFr mutations based on the presence or amount of expression of the polypeptide. In certain embodiments, a method of diagnosing a disease or condition which is related to one or more EGFr mutations in a subject comprises: (a) determining the presence or amount of transcription or translation of a mutant EGFr polynucleotide in a sample from the subject; and (b) diagnosing a disease or condition which is related to one or more EGFr mutations based on the presence or amount of transcription or translation of the polynucleotide. In certain embodiments, the disease or condition is cancer.

In certain embodiments, a method of diagnosing a disease or condition which is related to one or more EGFr mutations in a subject comprises: (a) determining the presence or amount of expression of a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 in a sample from the subject; and (b) diagnosing a disease or condition which is related to one or more EGFr mutations based on the presence or amount of expression of the polypeptide. In certain embodiments, a method of diagnosing a disease or condition which is related to one or more EGFr mutations in a subject comprises: (a) determining the presence or amount of transcription or translation of a polynucleotide encoding at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 in a sample from the subject; and (b) diagnosing a disease or condition which is related to one or more EGFr mutations based on the presence or amount of transcription or translation of the polynucleotide. In certain embodiments, the disease or condition is cancer.

In certain embodiments, a method of diagnosing a disease or condition which is related to one or more PI3K mutations in a subject is provided. In certain embodiments, a method of diagnosing a disease or condition which is related to one or more PI3K mutations in a subject comprises: (a) determining the presence or amount of expression of a mutant PI3K polypeptide in a sample from the subject; and (b) diagnosing a disease or condition which is related to one or more PI3K mutations based on the presence or amount of expression of the polypeptide. In certain embodiments, a method of diagnosing a disease or condition which is related to one or more PI3K mutations in a subject comprises: (a) determining the presence or amount of transcription or translation of a mutant PI3K polynucleotide in a sample from the subject; and (b) diagnosing a disease or condition which is related to one or more PI3K mutations based on the presence or amount of transcription or translation of the polynucleotide. In certain embodiments, the disease or condition is cancer.

In certain embodiments, a method of diagnosing a disease or condition which is related to one or more PI3K mutations in a subject comprises: (a) determining the presence or amount of expression of a polypeptide comprising at least one amino acid sequence selected from SEQ ID NO: 15, SEQ ID NO: 16, and SEQ ID NO: 17 in a sample from the subject; and (b) diagnosing a disease or condition which is related to one or more PI3K mutations based on the presence or amount of expression of the polypeptide. In certain embodiments, a method of diagnosing a disease or condition which is related to one or more PI3K mutations in a subject comprises: (a) determining the presence or amount of transcription or translation of a polynucleotide encoding at least one amino acid sequence selected from SEQ ID NO: 15, SEQ ID NO: 16, and SEQ ID NO: 17 in a sample from the subject; and (b) diagnosing a disease or condition which is related to one or more PI3K mutations based on the presence or amount of transcription or translation of the polynucleotide. In certain embodiments, the disease or condition is cancer.

In certain embodiments, a method of diagnosing a disease or condition which is related to one or more B-Raf mutations in a subject is provided. In certain embodiments, a method of diagnosing a disease or condition which is related to one or more B-Raf mutations in a subject comprises: (a) determining the presence or amount of expression of a mutant B-Raf polypeptide in a sample from the subject; and (b) diagnosing a disease or condition which is related to one or more B-Raf mutations based on the presence or amount of expression of the polypeptide. In certain embodiments, a method of diagnosing a disease or condition which is related to one or more B-Raf mutations in a subject comprises: (a) determining the presence or amount of transcription or translation of a mutant B-Raf polynucleotide in a sample from the subject; and (b) diagnosing a disease or condition which is related to one or more B-Raf mutations based on the presence or amount of transcription or translation of the polynucleotide. In certain embodiments, the disease or condition is cancer.

In certain embodiments, a method of diagnosing a disease or condition which is related to one or more B-Raf mutations in a subject comprises: (a) determining the presence or amount of expression of a polypeptide comprising at least one amino acid sequence selected from SEQ ID NO: 19, and SEQ ID NO: 20 in a sample from the subject; and (b) diagnosing a disease or condition which is related to one or more B-Raf mutations based on the presence or amount of expression of the polypeptide. In certain embodiments, a method of diagnosing a disease or condition which is related to one or more B-Raf mutations in a subject comprises: (a) determining the presence or amount of transcription or translation of a polynucleotide encoding at least one amino acid sequence selected from SEQ ID NO: 19 and SEQ ID NO: 20 in a sample from the subject; and (b) diagnosing a disease or condition which is related to one or more B-Raf mutations based on the presence or amount of transcription or translation of the polynucleotide. In certain embodiments, the disease or condition is cancer.

In certain embodiments, a method of diagnosing a susceptibility to a disease or condition which is related to one or more EGFr mutations in a subject is provided. In certain embodiments, a method of diagnosing a susceptibility to a disease or condition which is related to one or more EGFr mutations in a subject comprises: (a) determining the presence or amount of expression of a mutant EGFr polypeptide in a sample from the subject; and (b) diagnosing a susceptibility to a disease or condition which is related to one or more EGFr mutations based on the presence or amount of expression of the polypeptide. In certain embodiments, a method of diagnosing a susceptibility to a disease or condition which is related to one or more EGFr mutations in a subject comprises: (a) determining the presence or amount of transcription or translation of a mutant EGFr polynucleotide in a sample from the subject; and (b) diagnosing a susceptibility to a disease or condition which is related to one or more EGFr mutations based on the presence or amount of transcription or translation of the polynucleotide. In certain embodiments, the disease or condition is cancer.

In certain embodiments, a method of diagnosing a susceptibility to a disease or condition which is related to one or more EGFr mutations in a subject comprises: (a) determining the presence or amount of expression of a polypeptide comprising at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 in a sample from the subject; and (b) diagnosing a susceptibility to a disease or condition which is related to one or more EGFr mutations based on the presence or amount of expression of the polypeptide. In certain embodiments, a method of diagnosing a susceptibility to a disease or condition which is related to one or more EGFr mutations in a subject comprises: (a) determining the presence or amount of transcription or translation of a polynucleotide encoding at least one amino acid sequence selected from SEQ ID NO: 2, SEQ ID NO: 3, SEQ ID NO: 5, SEQ ID NO: 6, SEQ ID NO: 7, SEQ ID NO: 8, SEQ ID NO: 9, SEQ ID NO: 10, SEQ ID NO: 12, and SEQ ID NO: 13 in a sample from the subject; and (b) diagnosing a susceptibility to a disease or condition which is related to one or more EGFr mutations based on the presence or amount of transcription or translation of the polypeptide. In certain embodiments, the disease or condition is cancer.

In certain embodiments, a method of diagnosing a susceptibility to a disease or condition which is related to one or more PI3K mutations in a subject is provided. In certain embodiments, a method of diagnosing a susceptibility to a disease or condition which is related to one or more PI3K mutations in a subject comprises: (a) determining the presence or amount of expression of a mutant PI3K polypeptide in a sample from the subject; and (b) diagnosing a susceptibility to a disease or condition which is related to one or more PI3K mutations based on the presence or amount of expression of the polypeptide. In certain embodiments, a method of diagnosing a susceptibility to a disease or condition which is related to one or more PI3K mutations in a subject comprises: (a) determining the presence or amount of transcription or translation of a mutant PI3K polynucleotide in a sample from the subject; and (b) diagnosing a susceptibility to a disease or condition which is related to one or more PI3K mutations based on the presence or amount of transcription or translation of the polynucleotide. In certain embodiments, the disease or condition is cancer.

In certain embodiments, a method of diagnosing a susceptibility to a disease or condition which is related to one or more PI3K mutations in a subject comprises: (a) determining the presence or amount of expression of a polypeptide comprising at least one amino acid sequence selected from SEQ ID NO: 15, SEQ ID NO: 16, and SEQ ID NO: 17 in a sample from the subject; and (b) diagnosing a susceptibility to a disease or condition which is related to one or more PI3K mutations based on the presence or amount of expression of the polypeptide. In certain embodiments, a method of diagnosing a susceptibility to a disease or condition which is related to one or more PI3K mutations in a subject comprises: (a) determining the presence or amount of transcription or translation of a polynucleotide encoding at least one amino acid sequence selected from SEQ ID NO: 15, SEQ ID NO: 16, and SEQ ID NO: 17 in a sample from the subject; and (b) diagnosing a susceptibility to a disease or condition which is related to one or more PI3K mutations based on the presence or amount of transcription or translation of the polypeptide. In certain embodiments, the disease or condition is cancer.

In certain embodiments, a method of diagnosing a susceptibility to a disease or condition which is related to one or more B-Raf mutations in a subject is provided. In certain embodiments, a method of diagnosing a susceptibility to a disease or condition which is related to one or more B-Raf mutations in a subject comprises: (a) determining the presence or amount of expression of a mutant B-Raf polypeptide in a sample from the subject; and (b) diagnosing a susceptibility to a disease or condition which is related to one or more B-Raf mutations based on the presence or amount of expression of the polypeptide. In certain embodiments, a method of diagnosing a susceptibility to a disease or condition which is related to one or more B-Raf mutations in a subject comprises: (a) determining the presence or amount of transcription or translation of a mutant B-Raf polynucleotide in a sample from the subject; and (b) diagnosing a susceptibility to a disease or condition which is related to one or more B-Raf mutations based on the presence or amount of transcription or translation of the polynucleotide. In certain embodiments, the disease or condition is cancer.

In certain embodiments, a method of diagnosing a susceptibility to a disease or condition which is related to one or more B-Raf mutations in a subject comprises: (a) determining the presence or amount of expression of a polypeptide comprising at least one amino acid sequence selected from SEQ ID NO: 19 and SEQ ID NO: 20 in a sample from the subject; and (b) diagnosing a susceptibility to a disease or condition which is related to one or more B-Raf mutations based on the presence or amount of expression of the polypeptide. In certain embodiments, a method of diagnosing a susceptibility to a disease or condition which is related to one or more B-Raf mutations in a subject comprises: (a) determining the presence or amount of transcription or translation of a polynucleotide encoding at least one amino acid sequence selected from SEQ ID NO: 19 and SEQ ID NO: 20 in a sample from the subject; and (b) diagnosing a susceptibility to a disease or condition which is related to one or more B-Raf mutations based on the presence or amount of transcription or translation of the polypeptide. In certain embodiments, the disease or condition is cancer.

In certain embodiments, a method of determining the presence or absence of a polynucleotide encoding a mutant EGFr polypeptide is provided. In certain embodiments, a method of determining the presence or absence of a polynucleotide encoding a mutant EGFr polypeptide in a sample comprises (a) exposing a sample to a probe which hybridizes to a polynucleotide encoding a region of a mutant EGFr polypeptide, wherein the region comprises at least one EGFr mutation selected from L688P, Q701H, K745N, C781R, a histidine insertion between amino acids 771 and 772, T790M, L828stop, Q849R, F910L, and V948A, and (b) determining the presence or absence of a polynucleotide encoding a mutant EGFr polypeptide in the sample. In certain embodiments, a method of determining the presence or absence of a mutant EGFr polypeptide in a sample comprises (a) exposing a sample to a probe which hybridizes to a polynucleotide encoding a region of a mutant EGFr polypeptide, wherein the region comprises at least one EGFr mutation selected from L688P, Q701H, K745N, C781R, a histidine insertion between amino acids 771 and 772, T790M, L828stop, Q849R, F910L, and V948A, and (b) determining the presence or absence of a mutant EGFr polypeptide in the sample.

In certain embodiments, a method of determining the presence or absence of a polynucleotide encoding a mutant PI3K polypeptide is provided. In certain embodiments, a method of determining the presence or absence of a polynucleotide encoding a mutant PI3K polypeptide in a sample comprises (a) exposing a sample to a probe which hybridizes to a polynucleotide encoding a region of a mutant PI3K polypeptide, wherein the region comprises at least one PI3K mutation selected from E542K, E545A, and H1047L, and (b) determining the presence or absence of a polynucleotide encoding a mutant PI3K polypeptide in the sample. In certain embodiments, a method of determining the presence or absence of a mutant PI3K polypeptide in a sample comprises (a) exposing a sample to a probe which hybridizes to a polynucleotide encoding a region of a mutant PI3K polypeptide, wherein the region comprises at least one PI3K mutation selected from E542K, E545A, and H1047L, and (b) determining the presence or absence of a polynucleotide encoding a mutant PI3K polypeptide in the sample.

In certain embodiments, a method of determining the presence or absence of a polynucleotide encoding a mutant B-Raf polypeptide is provided. In certain embodiments, a method of determining the presence or absence of a polynucleotide encoding a mutant B-Raf polypeptide in a sample comprises (a) exposing a sample to a probe which hybridizes to a polynucleotide encoding a region of a mutant B-Raf polypeptide, wherein the region comprises at least one B-Raf mutation selected from V600E and K601E, and (b) determining the presence or absence of a polynucleotide encoding a mutant B-Raf polypeptide in the sample. In certain embodiments, a method of determining the presence or absence of a mutant B-Raf polypeptide in a sample comprises (a) exposing a sample to a probe which hybridizes to a polynucleotide encoding a region of a mutant B-Raf polypeptide, wherein the region comprises at least one B-Raf mutation selected from V600E and K601E, and (b) determining the presence or absence of a mutant B-Raf polypeptide in the sample.

In certain embodiments, a method of screening for a modulator of activity of at least one mutant EGFr polypeptide is provided. In certain embodiments, a method of screening for a modulator of activity of at least one mutant EGFr polypeptide comprises contacting a cell expressing at least one polynucleotide encoding a mutant EGFr polypeptide with a test compound; and detecting if the test compound modulates the activity of the mutant EGFr polypeptide. In certain such embodiments, the test compound increases the activity of the EGFr polypeptide. In certain such embodiments, the test compound decreases the activity of the EGFr polypeptide. In certain such embodiments, a test compound identified to decrease the activity of the EGFr polypeptide can be used to treat a disease or condition which is related to at least one mutant EGFr polypeptide. In certain such embodiments, a test compound identified to increase the activity of the EGFr polypeptide can be used to treat a disease or condition which is related to at least one mutant EGFr polypeptide.

In certain embodiments, a method of screening for a modulator of activity of at least one mutant PI3K polypeptide is provided. In certain embodiments, a method of screening for a modulator of activity of at least one mutant PI3K polypeptide comprises contacting a cell expressing at least one polynucleotide encoding a mutant PI3K polypeptide with a test compound; and detecting if the test compound modulates the activity of the mutant PI3K polypeptide. In certain such embodiments, the test compound increases the activity of the PI3K polypeptide. In certain such embodiments, the test compound decreases the activity of the PI3K polypeptide. In certain such embodiments, a test compound identified to decrease the activity of the PI3K polypeptide can be used to treat a disease or condition which is related to at least one mutant PI3K polypeptide. In certain such embodiments, a test compound identified to increase the activity of the PI3K polypeptide can be used to treat a disease or condition which is related to at least one mutant PI3K polypeptide.

In certain embodiments, a method of screening for a modulator of activity of at least one mutant B-Raf polypeptide is provided. In certain embodiments, a method of screening for a modulator of activity of at least one mutant B-Raf polypeptide comprises contacting a cell expressing at least one polynucleotide encoding a mutant B-Raf polypeptide with a test compound; and detecting if the test compound modulates the activity of the mutant B-Raf polypeptide. In certain such embodiments, the test compound increases the activity of the B-Raf polypeptide. In certain such embodiments, the test compound decreases the activity of the B-Raf polypeptide. In certain such embodiments, a test compound identified to decrease the activity of the B-Raf polypeptide can be used to treat a disease or condition which is related to at least one mutant B-Raf polypeptide. In certain such embodiments, a test compound identified to increase the activity of the B-Raf polypeptide can be used to treat a disease or condition which is related to at least one mutant B-Raf polypeptide.

In certain embodiments, a method for treating a subject for a disease or condition which is related to at least one EGFr mutation is provided. In certain embodiments, a method for treating a subject for a disease or condition which is related to at least one EGFr mutation is provided and the method comprises:

(a) detecting at least one EGFr mutation in a polynucleotide from the subject, wherein detection of at least one EGFr mutation indicates that the patient has an increased susceptibility for developing a disease or condition which is related to at least one EGFr mutation; and
(b) administering an antibody to the subject that specifically binds a mutant EGFr polypeptide.

In certain such embodiments, the antibody is a human antibody. In certain such embodiments, the antibody is panitumumab or an antigen binding region thereof.

In certain embodiments, a method for treating a subject for a disease or condition which is related to at least one EGFr mutation is provided and the method comprises:

(a) detecting at least one EGFr mutation in a polynucleotide from the subject, wherein detection of at least one EGFr mutation indicates that the patient has a disease or condition which is related to at least one EGFr mutation; and (b) administering an antibody to the subject that specifically binds a mutant EGFr polypeptide.

In certain such embodiments, the antibody is a human antibody. In certain such embodiments, the antibody is panitumumab or an antigen binding region thereof.

In certain embodiments, a method for treating a subject for a disease or condition which is related to at least one EGFr mutation is provided, wherein at least one of the EGFr mutations is selected from L688P, Q701H, K745N, C781R, a histidine insertion between amino acids 771 and 772, T790M, L828stop, Q849R, F910L, and V948A.

In certain embodiments, a method for treating a subject for a disease or condition which is related to at least one EGFr mutation is provided, wherein the disease or condition which is related to at least one EGFr mutation is non small cell lung carcinoma.

In certain embodiments, a method for treating a subject for a disease or condition which is related to at least one EGFr mutation is provided, comprising administering a polynucleotide antisense to a mutant EGFr polynucleotide to a subject in need of such treatment.

In certain embodiments, a method for establishing a mutant EGFr population profile in a specific population of individuals is provided comprising: (a) determining the presence of at least one EGFr mutation in a genetic profile of the individuals in a population; and (b) establishing a relationship between mutant EGFr genetic profiles and the individuals. In certain such embodiments, the specific characteristics of the individuals include a susceptibility to developing a disease or condition which is related to an EGFr mutation. In certain such embodiments, the specific characteristics of the individuals include exhibiting a disease or condition which is related to an EGFr mutation.

In certain embodiments, a method of predicting the efficacy of gefitinib treatment on a disease or condition in a subject is provided, comprising determining the presence or absence of EGFr mutation T790M in a mutant EGFr polypeptide of the subject, wherein the presence of the EGFr mutation T790M in one or more mutant EGFr polypeptides indicates resistance to treatment with gefitinib.

In certain embodiments, a method of determining responsiveness to treatment with an anti-EGFr antibody in a subject suffering from cancer is provided, comprising determining the presence or absence of EGFr mutation T790M in the subject. In certain such embodiments, the antibody is panitumumab or cetuximab.

In certain embodiments, a kit for detecting a polynucleotide encoding a mutant EGFr polypeptide in a subject is provided. In certain such embodiments, the kit comprises a probe which hybridizes to a polynucleotide encoding a region of a mutant EGFr polypeptide, wherein the region comprises at least one EGFr mutation selected from L688P, Q701H, K745N, C781R, a histidine insertion between amino acids 771 and 772, T790M, L828stop, Q849R, F910L, and V948A. In certain embodiments, the kit further comprises two or more amplification primers. In certain embodiments, the kit further comprises a detection component. In certain embodiments, the kit further comprises a nucleic acid sampling component.

The following examples, including the experiments conducted and results achieved are provided for illustrative purpose only and are not to be construed as limiting upon the present invention.

EXAMPLES

Example 1

Identification of EGFr, PI3K, and B-Raf Mutations in Non Small Cell Lung Carcinoma and Colorectal Adenocarcinoma Tumor Samples To identify mutations in EGFr, phosphatidylinositol 3'-kinase ("PI3K") and B-Raf associated with non small cell lung carcinoma ("NSCLC"), specific exons of EGFr, PI3K, and B-Raf were isolated and amplified from NSCLC tumor samples. Double-blinded tumor samples from twenty patients enrolled in a first line NSCLC trial comparing chemotherapeutic treatment alone (carboplatin/paclitaxel) versus chemotherapeutic treatment combined with panitumumab, a human anti-EGFr antibody (Amgen), were obtained prior to patient treatment with chemotherapy and/or panitumumab. To identify mutations in EGFr and PI3K associated with colorectal adenocarcinoma ("CRC"), specific exons of EGFr and PI3K were isolated and amplified from twenty CRC patient tumors. Double-blinded tumor samples from twenty patients enrolled in a first line CRC trial comparing chemotherapeutic treatment alone (carboplatin/paclitaxel) versus chemotherapeutic treatment combined with panitumumab, a human anti-EGFr antibody (Amgen), were obtained prior to patient treatment with chemotherapy and/or panitumumab. Each isolated exon was sequenced to identify any alterations from the wild-type sequences for those exons.

NSCLC tumor samples from twenty patients (Table 1) and CRC tumor samples from twenty patients (Table 2) were collected. A portion of each tumor sample was stained to identify the amount of EGFr expression of the tumor and rated for staining on a three-point scale (where 3 is the greatest degree of staining). At least 10% of each tumor sample demonstrated a staining level of three or greater. Tumor tissue was separated from adjacent normal tissue, necrotic debris, and stroma by macro dissection of formalin-fixed, paraffin-embedded tissue sections. Trimmed samples were fixed on microscope slides and stored at room temperature.

TABLE 1

NSCLC Patient Samples

| Histology Number | Patient Number | Clinical Trial Patient Number |
|---|---|---|
| 04H-361 JH-2 | 16914 | 4146 |
| 04H-362 JLM-2 | 16917 | 4178 |
| 04H-366 JKH-1 | 16928 | 4103 |
| 04H-368 DC-2 | 16935 | 4133 |
| 04H-370 WRW-2 | 16941 | 4140 |
| 04H-423 GHB S-1 | 17093 | 4113 |
| 04H-453 DSP S-1 | 17183 | 4130 |
| 04H-487 MMH S-1 | 17255 | 4118 |
| 04H-488 NSP S-1 | 17258 | 4121 |
| 04H-489 JDE S-1 | 17261 | 4135 |
| 04H-496 BAH S-1 | 17282 | 4161 |
| 04H-499 JMW S-1 | 17291 | 4143 |
| 04H-511 LRR S-1 | 17327 | 4182 |
| 04H-512 GLP S-1 | 17330 | 4183 |
| 04H-523 RLL S-1 | 17363 | 4116 |
| 04H-524 FPJ S-1 | 17366 | 4120 |
| 04H-525 DJK S-1 | 17369 | 4122 |

TABLE 1-continued

NSCLC Patient Samples

| Histology Number | Patient Number | Clinical Trial Patient Number |
|---|---|---|
| 04H-526 JMS S-1 | 17372 | 4129 |
| 04H-593 KMW-1 | 17891 | 4101 |
| 04H-595 REG-1 | 17897 | 4123 |

TABLE 2

CRC Patient Samples

| Histology Number | Patient Number | Clinical Trial Patient Number |
|---|---|---|
| 04H-537 MLB S-1 | 17380 | 9006 |
| 04H-538 TAO S-1 | 17383 | 9021 |
| 04H-540 RRK S-1 | 17389 | 9001 |
| 04H-541 HJB S-1 | 17392 | 9002 |
| 04H-542 PJW-1 | 17395 | 9003 |
| 04H-543 JWJ S-1 | 17398 | 9004 |
| 04H-546 RFH S-1 | 17407 | 9011 |
| 04H-547 WCD S-1 | 17410 | 9014 |
| 04H-548 LKW S-1 | 17413 | 9024 |
| 04H-550 DGA S-1 | 17419 | 9038 |
| 04H-551 TLR S-1 | 17422 | 9020 |
| 04H-552 KS S-1 | 17425 | 9037 |
| 04H-556 MJJ S-1 | 17437 | 9015 |
| 04H-557 MLR S-1 | 17440 | 9034 |
| 04H-559 PH S-1 | 17446 | 9040 |
| 04H-563 AMF S-1 | 17458 | 9033 |
| 04H-565 RCR S-1 | 17464 | 9029 |
| 04H-566 GC S-1 | 17467 | 9039 |
| 04H-567 GWB S-1 | 17470 | 9013 |
| 04H-568 HLB S-1 | 17473 | 9019 |

Genomic DNA was prepared from the sample slides using the Pinpoint Slide DNA Isolation System (Zymo Research, Orange, Calif.) according to the manufacturer's protocol. The final isolated genomic DNA product was dissolved in 500 μL water. The sequences corresponding to exons 18, 19, 20, 21, and 23 of human EGFr, exons 9 and 20 of human PI3K, and exon 15 of human B-Raf were amplified by PCR using primers specific for each exon. Primer sequences for each exon were designed using the intron sequences 5' and 3' to each exon in the wild-type EGFr cDNA sequence (Genbank Accession No. AC006977; SEQ ID NO: 55). The genomic wild-type EGFr nucleotide sequence is found at Genbank Accession No. AC073324. The wild-type EGFr polypeptide sequence is found at Genbank Accession No. AAS83109 (SEQ ID NO: 1). The forward primer for EGFr exon 18 was 5'-GGG CCA TGT CTG GCA CTG CTT TCC-3' (SEQ ID NO: 22), and the reverse primer for EGFr exon 18 was 5'-GAA ATA TAC AGC TTG CAA GGA CTC-3' (SEQ ID NO: 23). The forward primer for EGFr exon 19 was 5'-AAT ATC AGC CTT AGG TGC GGC TCC-3' (SEQ ID NO: 24), and the reverse primer for EGFr exon 19 was 5'-GAG AAA AGG TGG GCC TGA GGT TC-3' (SEQ ID NO: 25). The forward primer for EGFr exon 20 was 5'-CTG CGT AAA CGT CCC TGT GCT AGG TC-3' (SEQ ID NO: 26) and the reverse primer for EGFr exon 20 was 5'-GCA CGC ACA CAC ATA TCC CCA TGG C-3' (SEQ ID NO: 27). The forward primer for EGFr exon 21 was 5'-GCA TGA ACA TGA CCC TGA ATT CGG-3' (SEQ ID NO: 28) and the reverse primer for EGFr exon 21 was 5'-CCT GCA TGT GTT AAA CAA TAC AGC-3' (SEQ ID NO: 29). The forward primer for EGFr exon 23 was 5'-TCA TTC ATG ATC CCA CTG CCT TC-3' (SEQ ID NO: 30), and the reverse primer for EGFr exon 23 was 5'-CAG CTG TTT GGC TAA GAG CAG CC-3' (SEQ ID NO: 31).

The wild-type PI3K polypeptide sequence is found at Genbank Accession No. U79143 (SEQ ID NO: 14). The wild-type PI3K cDNA sequence is shown in FIG. 7 (SEQ ID NO: 58). The forward primer for PI3K exon 9 was 5'-CTG TAA ATC ATC TGT GAA TCC AGA GGG G-3' (SEQ ID NO: 32), and the reverse primer for PI3K exon 9 was 5'-GTA AAT TCT GCT TTA TTT ATT CCA ATA GGT ATG G-3' (SEQ ID NO: 33). The forward primer for PI3K exon 20 was 5'-CTA CGA AAG CCT CTC TAA TTT TGT GAO ATT TGA GC-3' (SEQ ID NO: 34), and the reverse primer for PI3K exon 20 was 5'-CTT GCT GTA AAT TCT AAT GCT GTT CAT GGA TTG TGC-3' (SEQ ID NO: 35). The wild-type B-Raf polypeptide sequence is found at Genbank Accession No. NM004333 (SEQ ID NO: 18). The wild-type B-Raf cDNA sequence is shown in FIG. 8 (SEQ ID NO: 60). The forward primer for B-Raf exon 11 was 5'-GGG GAT CTC TTC CTG TAT CCC TCT CAG GC-3' (SEQ ID NO: 36), and the reverse primer for B-Raf exon 11 was 5'-GTT TAT TGA TGC GAA CAG TGA ATA TTT CC-3' (SEQ ID NO: 37). The forward primer for B-Raf exon 15 was 5'-CAT AAT GCT TGC TCT GAT AGG-3' (SEQ ID NO: 38), and the reverse primer for B-Raf exon 15 was 5'-GTA ACT CAG CAG CAT CTC AG-3' (SEQ ID NO: 39).

PCR was performed using Taq DNA polymerase (Roche Diagnostics Corp) and the following conditions: 5 μL of 10× Taq buffer, 0.5 μL of 24 mM $MgCl_2$, 1 μL genomic DNA (approximately 0.5 ng), 7 μL of 2.5 mM dNTPs, 1 μL Taq polymerase (5 U) and 29.5 μL $ddH_2O$ were combined and mixed. Six μL of combined primer stock (10 μM of each) was added to each tube. The cycle protocol was 1 cycle of 4 minutes at 93° C., 10 seconds at 93° C., 30 seconds at 62° C., 30 seconds at 72° C. for 35 cycles, and 1 cycle of 4 min at 72° C. At the end of the reaction the temperature was held at 4° C.

The PCR products for each individual exon were pooled and gel-purified. The purified amplified exon sequences were subcloned into a pCR2.1 vector using a TOPO-TA Cloning Kit (Invitrogen Corp) according to the manufacturer's instructions. *E. coli* colonies containing the vector and insert exon of interest were picked by a Genetix Colony Picker. Those colonies were grown overnight in liquid medium. Plasmid DNA from each overnight bacterial culture was isolated using a QIAGEN 9600, 3000, or 8000 Bio-robot (Qiagen) according to the manufacturer's instructions.

Isolated plasmid DNA containing each exon was sequenced using a BigDye 3.1 Terminator Kit (Applied Biosystems, Inc.) according to the manufacturer's instructions. Sequencing data was collected using a 3700, 3100, or 3730 Genetic Analyzer (Applied Biosystems, Inc.), and analyzed using the SeQuencher program (GeneCodes Corp.). The exon sequences from the patient samples were compared to the wild-type exon sequences. The results are shown schematically in FIGS. 1 and 2.

The mutational analysis of the NSCLC patient tumor samples (FIG. 1) identified several mutations in EGFr: two different mutations in exon 18 of EGFr in two different patients (Q701H (SEQ ID NO: 40, which encodes the polypeptide of SEQ ID NO: 3) and L688P (SEQ ID NO: 41, which encodes the polypeptide of SEQ ID NO: 2)); a 15 base pair deletion (SEQ ID NO: 42, which encodes the polypeptide of SEQ ID NO: 4) and a mutation (K745N (SEQ ID NO: 43, which encodes the polypeptide of SEQ ID NO: 5)) in exon 19 of EGFr in two different patients; three different mutations in exon 20 of EGFr in three different patients (C781R (SEQ ID NO: 44, which encodes the polypeptide of SEQ ID NO: 6), T790M (SEQ ID NO: 45, which encodes the polypeptide of SEQ ID NO: 8), and a histidine insertion between amino acids 771 and 772 (SEQ ID NO: 46, which encodes the polypeptide of SEQ ID NO: 7)); one mutation (Q849R (SEQ ID NO: 47, which encodes the polypeptide of SEQ ID NO: 10)) in exon 21 of EGFr in a single patient; and two different mutations in exon 23 of EGFr in two different patients (V948A (SEQ ID NO: 48, which encodes the polypeptide of SEQ ID NO: 13) and F910L (SEQ ID NO: 49, which encodes the polypeptide of SEQ ID NO: 12)). Analysis of the PI3K exons in the NSCLC patient samples identified a single mutation (E545A (SEQ ID NO: 50, which encodes the polypeptide of SEQ ID NO: 16)) in exon 9 of PI3K that was observed in seven different patients and no mutations in exon 20 of PI3K. Analysis of B-Raf exon 15 also identified a single mutation (V600E (SEQ ID NO: 51, which encodes the polypeptide of SEQ ID NO: 19)) in two different patients.

The mutational analysis of the CRC patient tumor samples, in contrast, did not identify any mutations of EGFr in the twenty CRC patients (FIG. 2). Thirteen of the twenty patients had the same E545A mutation (SEQ ID NO: 50, which encodes the polypeptide of SEQ ID NO: 16) in exon 9 of PI3K that had been previously identified in the NSCLC patient samples. In addition, the mutation E542K (SEQ ID NO: 53, which encodes the polypeptide of SEQ ID NO: 15) was identified in three other patients in that exon. One mutation (H1047L (SEQ ID NO: 54, which encodes the polypeptide of SEQ ID NO: 17)) was identified in exon 20 of PI3K, in a single patient.

Thus twelve different EGFr mutations, one PI3K mutation, and one B-Raf mutation were identified in the NSCLC patient tumor samples, while three PI3K mutations and no EGFr mutations were identified in the CRC patient tumor samples.

Example 2

Expanded Non Small Cell Lung Carcinoma Mutational Analysis

An expanded mutational study of thirty-nine additional NSCLC patient tumor samples was performed. Double-blinded tumor samples from thirty-nine patients enrolled in a first line NSCLC trial comparing chemotherapeutic treatment alone (carboplatin/paclitaxel) versus chemotherapeutic treatment combined with panitumumab, a human anti-EGFr antibody (Amgen), were obtained prior to patient treatment with chemotherapy and/or panitumumab. Using the identical DNA isolation, amplification, sub-cloning, and analysis procedures as set forth in Example 1, EGFr exons 18, 19, 20, 21, and 23, and B-Raf exons 11 and 15 were analyzed for the presence of mutations. The thirty-nine samples are detailed in Table 3, and the results of the analyses of those samples appear in FIG. 3.

TABLE 3

NSCLC Patient Samples for Expanded Study

| Histology Number | Patient Number | Clinical Trial Patient Number |
|---|---|---|
| 04H-424 JAQ S-2 | 17096 | 4119 |
| 04H-425 JZ-2 | 17099 | 4228 |
| 04H-426 PAP-2 | 17102 | 4233 |
| 04H-427 SFD-2 | 17105 | 4239 |
| 04H-428 AMB S-2 | 17108 | 4167 |
| 04H-429 ELH S-2 | 17111 | 4273 |
| 04H-430 HDD S-2 | 17114 | 4144 |
| 04H-431 CMW S-2 | 17117 | 4213 |
| 04H-432 JL S-2 | 17120 | 4165 |
| 04H-433 RC S-2 | 17123 | 4170 |
| 04H-434 RZ S-2 | 17126 | 4219 |
| 04H-435 GK S-2 | 17129 | 4265 |
| 04H-436 RT S-2 | 17132 | 4248 |
| 04H-437 MMF S-2 | 17135 | 4240 |
| 04H-438 JDR S-2 | 17138 | 4179 |
| 04H-439 LC S-2 | 17141 | 4256 |
| 04H-440 GLP S-2 | 17144 | 4275 |
| 04H-441 MHR S-2 | 17147 | 4206 |
| 04H-442 JEF S-2 | 17150 | 4222 |
| 04H-443 HBA S-2 | 17153 | 4223 |
| 04H-444 DT S-2 | 17156 | 4231 |
| 04H-447 CD S-2 | 17165 | 4207 |
| 04H-449 DWB S-2 | 17171 | 4164 |
| 04H-450 DLR S-2 | 17174 | 4211 |
| 04H-454 NPJ S-2 | 17186 | 4136 |
| 04H-456 NEN S-2 | 17192 | 4151 |
| 04H-461 LWF S-2 | 17207 | 4218 |
| 04H-479 MAT S-2 | 17231 | 4229 |
| 04H-482 GPH S-2 | 17240 | 4221 |
| 04H-484 JP S-2 | 17246 | 4156 |
| 04H-493 JS S-2 | 17273 | 4208 |
| 04H-497 JMP S-2 | 17285 | 4189 |
| 04H-503 SAS S-2 | 17303 | 4254 |
| 04H-504 JDD S-2 | 17306 | 4152 |
| 04H-507 RWR S-2 | 17315 | 4157 |
| 04H-510 CSL S-2 | 17324 | 4180 |
| 04H-513 ALF S-2 | 17333 | 4205 |
| 04H-515 VIT S-2 | 17339 | 4149 |
| 04H-522 VAB S-2 | 17360 | 4257 |

The results of the analysis identified no mutations in EGFr exons 20, or 23. A single mutation was identified in EGFr exon 18 (L688P (SEQ ID NO: 41, which encodes the polypeptide of SEQ ID NO: 2)) in four different patient samples. A single 15 base pair deletion (SEQ ID NO: 42, which encodes the polypeptide of SEQ ID NO: 4) in EGFr exon 19 was identified in a single patient sample. Two mutations were identified in EGFr exon 21 (L858R (SEQ ID NO: 61, which encodes the polypeptide of SEQ ID NO: 11) and L828stop (SEQ ID NO: 56, which encodes the polypeptide of SEQ ID NO: 9)), each in two different patients. No mutations were identified in B-Raf exon 11. One mutation, K601E (SEQ ID NO: 57, which encodes the polypeptide of SEQ ID NO: 20), was identified in B-Raf exon 15 in a single patient sample. Of the observed mutations, two had been previously identified in Example 1 (L688P in EGFr exon 18 and the 15 base pair deletion in EGFr exon 19), and three were newly identified (L858R and L828stop in EGFr exon 21, and K601E in B-Raf exon 15). In all, nine confirmed mutations in the EGFr gene were identified in eight NSCLC patient samples, and one confirmed mutation in the B-Raf gene was identified in one NSCLC patient.

Example 3

Analysis of Autophosphorylation Capability of Mutant EGFr Polypeptide

Typically, EGFr undergoes an autophosphorylation event as a precursor to internalization upon binding to a ligand such as EGF or TGF-α. Accordingly, certain EGFr mutant polypeptides identified in Example 2 were studied to determine inhibition of EGF-induced EGFr phosphorylation in vitro.

Chinese hamster ovary cell lines overexpressing wild-type (SEQ ID NO: 1) or mutated EGFr polypeptide were constructed. Cells from each line were plated and treated with 0-2

μM of either panitumumab or gefitinib Iressa™, 4-quinazolinamine, N-(3-chloro-4-fluorophenyl)-7-methoxy-6-[3-4-morpholin) propoxy], a small molecule kinase inhibitor) prior to stimulation with EGF. The 1050 for EGF-induced autophosphorylation was calculated for the gefitinib and panitumumab-treated samples (Table 4). The raw electrophoresis data for wild-type EGFr and the T790M mutant EGFr polypeptides are shown in FIG. 4.

TABLE 4

IC50 for EGFr Autophosphorylation after Treatment with Gefitinib or Panitumumab

| EGFr Mutation | gefitinib pretreatment IC50 (nM) | panitumumab pretreatment IC50 (nM) |
|---|---|---|
| none (wild-type) | 14.6 | 0.23 |
| 15 base pair deletion in exon 19 | 1.4 | 0.17 |
| L858R in exon 21 | 3.2 | 0.18 |
| T790M in exon 20 | >2000 | 0.23 |

As shown in Table 4, both gefitinib and panatumumab were effective in preventing EGFr autophosphorylation at low concentration for the wild-type EGFr and the 15 base pair deletion and L858R EGFr mutants. Autophosphorylation of the T790M mutant EGFr polypeptide, however, was not inhibited by gefitinib (IC50>2000 nM), yet was effectively inhibited by panitumumab (IC50 of 0.23 nM). Thus, panitumumab may be a more efficacious treatment than gefitinib for NSCLC patients having a T790M mutation in EGFr exon 20 than gefitinib.

Example 4

Correlation of Mutational Analysis with Panitumumab Efficacy

After the mutational analysis of Example 2, the results of the study were unblinded for the patients in which mutations were observed (Table 5). Clinical data was assessed by an investigator every six weeks using the Response Evaluation Criteria In Solid Tumors (RECIST), which provides guidelines for identifying improvement, stable disease, or progressive disease based on tumor size (see Therasse et al., February 2000, "New Guidelines to Evaluate the Response to Treatment in Solid Tumors," J. Natl. Cancer Inst. 92(3): 205-216).

TABLE 5

NSCLC Patient Samples

| Identified Mutation | Gender | Smoking History | Treatment | % EGFr with staining level of 3 or greater) | Response |
|---|---|---|---|---|---|
| 15 base pair deletion exon 19 | male | never | chemo | 60 | stable disease |
| L688P Exon 18 | female | former | chemo | 50 | stable disease |
| L688P Exon 18 | male | former | chemo | 80 | partial response |
| L688P Exon 18 | male | former | chemo | 10 | stable disease |
| T790M Exon 20 | male | former | chemo + panitumumab | 10 | stable disease |
| L858R Exon 21 | male | former | chemo + panitumumab | 90 | stable disease |
| Q701H Exon 18 | female | never | chemo + panitumumab | 20 | progressive disease |
| 15 base pair deletion exon 19 | female | never | chemo + panitumumab | 40 | partial response |

The results demonstrate that panitumumab in combination with chemotherapy yielded stable disease for at least 12 weeks for those patients with a T790M mutation in EGFr Exon 20 and a L858R mutation in EGFr Exon 21. Using the chemotherapy/panitumumab combination therapy, a partial response was observed in a patient with a 15 base pair deletion in EGFr exon 19. In contrast, a patient with the same 15 base pair deletion in EGFr exon 19 achieved only stable disease with chemotherapeutic treatment alone.

Recent studies have identified several EGFr mutations in tumors from NSCLC that display sensitivity to the EGFr tyrosine kinase inhibitors gefitinib Oressa™ (AstraZeneca) and erlotinib (Tarceva™ (Genentech), N-(3-ethynylphenyl)-6,7-bis(2-methoxyethoxy)-4-quinazolinamine). Lynch et al. (2004, "Activating Mutations in the Epidermal Growth Factor Receptor Underlying Responsiveness of Non-Small-Cell Lung Cancer to Gefitinib," New England J. Med. 350(21): 2129-39) found that the following EGFr mutations were associated with the susceptibility of NSCLC patient tumors to treatment with gefitinib: deletions in the amino acid 746-753 region, L858R, L861Q, and G719C. Paez et al. (2004, "EGFR Mutations in Lung Cancer: Correlation with Clinical Response to Gefitinib Therapy," Science 304: 1497-1500) had similar findings to Lynch et al., identifying tumors with EGFr mutations L858R, G7195, and various deletion mutations between amino acids 746 and 759 as being susceptible to treatment with gefitinib. Pao et al., 2004 ("EGF receptor gene mutations are common in lung cancers from "never smokers" and are associated with sensitivity of tumors to gefitinib and erlotinib," Proc. Natl. Acad. Sci. USA 101(36): 13306-13311), found that similar EGFr mutations (E746-A750 deletion, L747-5752 deletion, L858R, and R776C/L858R) were associated with susceptibility of NSCLC tumors to treatment with gefitinib or erlotinib.

Like those studies, the studies discussed in Examples 1 and 2 also identified the 15 base pair deletion mutant in exon 19, and L858R in exon 21 as EGFr mutations associated with NSCLC tumors. Of the data for which unblinded patient outcomes were available, the tumors containing either of those two mutations or T790M were inhibited by panitumumab in combination with chemotherapy. The T790M mutation, however, was not previously identified in the gefitinib/erlotinib experiments. In vitro studies demonstrate that while autophosphorylation of T790M EGFr mutants is effectively inhibited at very low concentrations of panitumumab, gefitinib is not an effective inhibitor of autophosphorylation of that mutant EGFr. Thus, panitumumab combination therapy and not gefitinib may be an effective treatment for T790M EGFr mutants.

Other embodiments will be apparent to those skilled in the art from consideration of the specification and practice of the invention disclosed herein. It is intended that the specification and examples be considered as exemplary only, with a true scope and spirit of the invention being indicated by the following claims.

We claim:

1. An isolated polypeptide comprising the amino acid sequence selected from SEQ ID NO: 2, SEQ ID NO: 3, SEQ ID NO: 5, SEQ ID NO: 6, SEQ ID NO: 7, SEQ ID NO: 10, SEQ ID NO: 12, and SEQ ID NO: 13.

2. An isolated polypeptide consisting of the amino acid sequence selected from SEQ ID NO: 2, SEQ ID NO: 3, SEQ ID NO: 5, SEQ ID NO: 6, SEQ ID NO: 7, SEQ ID NO: 9, SEQ ID NO: 10, SEQ ID NO: 12, and SEQ ID NO: 13.

3. An isolated polypeptide comprising the amino acid sequence selected from SEQ ID NO: 15, SEQ ID NO: 16, and SEQ ID NO: 17.

4. An isolated polypeptide consisting of the amino acid sequence selected from SEQ ID NO: 15, SEQ ID NO: 16, and SEQ ID NO: 17.

5. An isolated polypeptide comprising the amino acid sequence of SEQ ID NO: 20.

6. An isolated polypeptide consisting of the amino acid sequence of SEQ ID NO: 20.

7. A fusion protein comprising the isolated polypeptide of any of claims 1, 2, 3, 4, 5, and 6, fused to a heterologous polypeptide.

* * * * *

SEQUENCE LISTING

```
<160> NUMBER OF SEQ ID NOS: 82

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335
```

```
Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765
```

```
Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
```

```
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210


<210> SEQ ID NO 2
<211> LENGTH: 1210
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
```

```
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Pro
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765
```

```
Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185
```

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 3
<211> LENGTH: 1210
<212> TYPE: PRT
<213> ORGANISM: Homo sapiens

<400> SEQUENCE: 3

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

```
Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn His Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
```

```
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185
```

```
Gly Ser Thr Ala Glu Asn Ala Glu Tyr Leu Arg Val Ala Pro Gln
    1190                1195                1200

Ser Ser Glu Phe Ile Gly Ala
    1205                1210


<210> SEQ ID NO 4
<211> LENGTH: 1205
<212> TYPE: PRT
<213> ORGANISM: Homo sapiens

<400> SEQUENCE: 4

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350
```

```
Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Thr Ser Pro Lys Ala Asn Lys
            740                 745                 750

Glu Ile Leu Asp Glu Ala Tyr Val Met Ala Ser Val Asp Asn Pro His
        755                 760                 765

Val Cys Arg Leu Leu Gly Ile Cys Leu Thr Ser Thr Val Gln Leu Ile
    770                 775                 780
```

```
Thr Gln Leu Met Pro Phe Gly Cys Leu Leu Asp Tyr Val Arg Glu His
785                 790                 795                 800

Lys Asp Asn Ile Gly Ser Gln Tyr Leu Leu Asn Trp Cys Val Gln Ile
                805                 810                 815

Ala Lys Gly Met Asn Tyr Leu Glu Asp Arg Arg Leu Val His Arg Asp
            820                 825                 830

Leu Ala Ala Arg Asn Val Leu Val Lys Thr Pro Gln His Val Lys Ile
        835                 840                 845

Thr Asp Phe Gly Leu Ala Lys Leu Leu Gly Ala Glu Glu Lys Glu Tyr
    850                 855                 860

His Ala Glu Gly Gly Lys Val Pro Ile Lys Trp Met Ala Leu Glu Ser
865                 870                 875                 880

Ile Leu His Arg Ile Tyr Thr His Gln Ser Asp Val Trp Ser Tyr Gly
                885                 890                 895

Val Thr Val Trp Glu Leu Met Thr Phe Gly Ser Lys Pro Tyr Asp Gly
            900                 905                 910

Ile Pro Ala Ser Glu Ile Ser Ser Ile Leu Glu Lys Gly Glu Arg Leu
        915                 920                 925

Pro Gln Pro Pro Ile Cys Thr Ile Asp Val Tyr Met Ile Met Val Lys
    930                 935                 940

Cys Trp Met Ile Asp Ala Asp Ser Arg Pro Lys Phe Arg Glu Leu Ile
945                 950                 955                 960

Ile Glu Phe Ser Lys Met Ala Arg Asp Pro Gln Arg Tyr Leu Val Ile
                965                 970                 975

Gln Gly Asp Glu Arg Met His Leu Pro Ser Pro Thr Asp Ser Asn Phe
            980                 985                 990

Tyr Arg Ala Leu Met Asp Glu Glu  Asp Met Asp Asp Val  Val Asp Ala
        995                 1000                1005

Asp Glu  Tyr Leu Ile Pro Gln  Gln Gly Phe Phe Ser  Ser Pro Ser
    1010                1015                1020

Thr Ser  Arg Thr Pro Leu Leu  Ser Ser Leu Ser Ala  Thr Ser Asn
    1025                1030                1035

Asn Ser  Thr Val Ala Cys Ile  Asp Arg Asn Gly Leu  Gln Ser Cys
    1040                1045                1050

Pro Ile  Lys Glu Asp Ser Phe  Leu Gln Arg Tyr Ser  Ser Asp Pro
    1055                1060                1065

Thr Gly  Ala Leu Thr Glu Asp  Ser Ile Asp Asp Thr  Phe Leu Pro
    1070                1075                1080

Val Pro  Glu Tyr Ile Asn Gln  Ser Val Pro Lys Arg  Pro Ala Gly
    1085                1090                1095

Ser Val  Gln Asn Pro Val Tyr  His Asn Gln Pro Leu  Asn Pro Ala
    1100                1105                1110

Pro Ser  Arg Asp Pro His Tyr  Gln Asp Pro His Ser  Thr Ala Val
    1115                1120                1125

Gly Asn  Pro Glu Tyr Leu Asn  Thr Val Gln Pro Thr  Cys Val Asn
    1130                1135                1140

Ser Thr  Phe Asp Ser Pro Ala  His Trp Ala Gln Lys  Gly Ser His
    1145                1150                1155

Gln Ile  Ser Leu Asp Asn Pro  Asp Tyr Gln Gln Asp  Phe Phe Pro
    1160                1165                1170

Lys Glu  Ala Lys Pro Asn Gly  Ile Phe Lys Gly Ser  Thr Ala Glu
    1175                1180                1185

Asn Ala  Glu Tyr Leu Arg Val  Ala Pro Gln Ser Ser  Glu Phe Ile
```

```
    1190                1195                1200

Gly Ala
    1205


<210> SEQ ID NO 5
<211> LENGTH: 1210
<212> TYPE: PRT
<213> ORGANISM: Homo sapiens

<400> SEQUENCE: 5

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
```

```
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Asn Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780
```

```
Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200
```

```
Ser Ser Glu Phe Ile Gly Ala
    1205                1210


<210> SEQ ID NO 6
<211> LENGTH: 1210
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Arg Leu Thr Ser
    770                 775                 780

Thr Val Gln Leu Ile Thr Gln Leu Met Pro Phe Gly Cys Leu Leu Asp
```

-continued

```
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200
```

```
Ser Ser  Glu Phe Ile Gly Ala
    1205                1210


<210> SEQ ID NO 7
<211> LENGTH: 1211
<212> TYPE: PRT
<213> ORGANISM: Homo sapiens

<400> SEQUENCE: 7

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn His Pro His Val Cys Arg Leu Leu Gly Ile Cys Leu Thr
    770                 775                 780

Ser Thr Val Gln Leu Ile Thr Gln Leu Met Pro Phe Gly Cys Leu Leu
785                 790                 795                 800
```

```
Asp Tyr Val Arg Glu His Lys Asp Asn Ile Gly Ser Gln Tyr Leu Leu
                805                 810                 815

Asn Trp Cys Val Gln Ile Ala Lys Gly Met Asn Tyr Leu Glu Asp Arg
            820                 825                 830

Arg Leu Val His Arg Asp Leu Ala Ala Arg Asn Val Leu Val Lys Thr
        835                 840                 845

Pro Gln His Val Lys Ile Thr Asp Phe Gly Leu Ala Lys Leu Leu Gly
    850                 855                 860

Ala Glu Glu Lys Glu Tyr His Ala Glu Gly Gly Lys Val Pro Ile Lys
865                 870                 875                 880

Trp Met Ala Leu Glu Ser Ile Leu His Arg Ile Tyr Thr His Gln Ser
                885                 890                 895

Asp Val Trp Ser Tyr Gly Val Thr Val Trp Glu Leu Met Thr Phe Gly
            900                 905                 910

Ser Lys Pro Tyr Asp Gly Ile Pro Ala Ser Glu Ile Ser Ser Ile Leu
        915                 920                 925

Glu Lys Gly Glu Arg Leu Pro Gln Pro Pro Ile Cys Thr Ile Asp Val
    930                 935                 940

Tyr Met Ile Met Val Lys Cys Trp Met Ile Asp Ala Asp Ser Arg Pro
945                 950                 955                 960

Lys Phe Arg Glu Leu Ile Ile Glu Phe Ser Lys Met Ala Arg Asp Pro
                965                 970                 975

Gln Arg Tyr Leu Val Ile Gln Gly Asp Glu Arg Met His Leu Pro Ser
            980                 985                 990

Pro Thr Asp Ser Asn Phe Tyr Arg  Ala Leu Met Asp Glu  Glu Asp Met
        995                 1000                1005

Asp Asp  Val Val Asp Ala Asp  Glu Tyr Leu Ile Pro  Gln Gln Gly
    1010                1015                1020

Phe Phe  Ser Ser Pro Ser Thr  Ser Arg Thr Pro Leu  Leu Ser Ser
    1025                1030                1035

Leu Ser  Ala Thr Ser Asn Asn  Ser Thr Val Ala Cys  Ile Asp Arg
    1040                1045                1050

Asn Gly  Leu Gln Ser Cys Pro  Ile Lys Glu Asp Ser  Phe Leu Gln
    1055                1060                1065

Arg Tyr  Ser Ser Asp Pro Thr  Gly Ala Leu Thr Glu  Asp Ser Ile
    1070                1075                1080

Asp Asp  Thr Phe Leu Pro Val  Pro Glu Tyr Ile Asn  Gln Ser Val
    1085                1090                1095

Pro Lys  Arg Pro Ala Gly Ser  Val Gln Asn Pro Val  Tyr His Asn
    1100                1105                1110

Gln Pro  Leu Asn Pro Ala Pro  Ser Arg Asp Pro His  Tyr Gln Asp
    1115                1120                1125

Pro His  Ser Thr Ala Val Gly  Asn Pro Glu Tyr Leu  Asn Thr Val
    1130                1135                1140

Gln Pro  Thr Cys Val Asn Ser  Thr Phe Asp Ser Pro  Ala His Trp
    1145                1150                1155

Ala Gln  Lys Gly Ser His Gln  Ile Ser Leu Asp Asn  Pro Asp Tyr
    1160                1165                1170

Gln Gln  Asp Phe Phe Pro Lys  Glu Ala Lys Pro Asn  Gly Ile Phe
    1175                1180                1185

Lys Gly  Ser Thr Ala Glu Asn  Ala Glu Tyr Leu Arg  Val Ala Pro
    1190                1195                1200

Gln Ser  Ser Glu Phe Ile Gly  Ala
```

```
    1205                1210


<210> SEQ ID NO 8
<211> LENGTH: 1210
<212> TYPE: PRT
<213> ORGANISM: Homo sapiens

<400> SEQUENCE: 8

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
```

```
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Met Gln Leu Met Pro Phe Gly Cys Leu Leu Asp
785                 790                 795                 800
```

```
Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210
```

<210> SEQ ID NO 9
<211> LENGTH: 827
<212> TYPE: PRT
<213> ORGANISM: Homo sapiens

<400> SEQUENCE: 9

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380
```

```
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
```

```
                805                 810                 815

Trp Cys Val Gln Ile Ala Lys Gly Met Asn Tyr
            820                 825


<210> SEQ ID NO 10
<211> LENGTH: 1210
<212> TYPE: PRT
<213> ORGANISM: Homo sapiens

<400> SEQUENCE: 10

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
```

```
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780
```

```
Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Arg His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200
```

```
Ser Ser  Glu Phe Ile Gly Ala
    1205                1210


<210> SEQ ID NO 11
<211> LENGTH: 1210
<212> TYPE: PRT
<213> ORGANISM: Homo sapiens

<400> SEQUENCE: 11

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
```

```
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Arg Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200
```

```
Ser Ser  Glu Phe Ile Gly Ala
    1205                1210


<210> SEQ ID NO 12
<211> LENGTH: 1210
<212> TYPE: PRT
<213> ORGANISM: Homo sapiens

<400> SEQUENCE: 12

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

-continued

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800
```

```
Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Leu Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
```

1205 1210

<210> SEQ ID NO 13
<211> LENGTH: 1210
<212> TYPE: PRT
<213> ORGANISM: Homo sapiens

<400> SEQUENCE: 13

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Val Cys Gln
20 25 30

Gly Thr Ser Asn Lys Leu Thr Gln Leu Gly Thr Phe Glu Asp His Phe
35 40 45

Leu Ser Leu Gln Arg Met Phe Asn Asn Cys Glu Val Val Leu Gly Asn
50 55 60

Leu Glu Ile Thr Tyr Val Gln Arg Asn Tyr Asp Leu Ser Phe Leu Lys
65 70 75 80

Thr Ile Gln Glu Val Ala Gly Tyr Val Leu Ile Ala Leu Asn Thr Val
85 90 95

Glu Arg Ile Pro Leu Glu Asn Leu Gln Ile Ile Arg Gly Asn Met Tyr
100 105 110

Tyr Glu Asn Ser Tyr Ala Leu Ala Val Leu Ser Asn Tyr Asp Ala Asn
115 120 125

Lys Thr Gly Leu Lys Glu Leu Pro Met Arg Asn Leu Gln Glu Ile Leu
130 135 140

His Gly Ala Val Arg Phe Ser Asn Asn Pro Ala Leu Cys Asn Val Glu
145 150 155 160

Ser Ile Gln Trp Arg Asp Ile Val Ser Ser Asp Phe Leu Ser Asn Met
165 170 175

Ser Met Asp Phe Gln Asn His Leu Gly Ser Cys Gln Lys Cys Asp Pro
180 185 190

Ser Cys Pro Asn Gly Ser Cys Trp Gly Ala Gly Glu Glu Asn Cys Gln
195 200 205

Lys Leu Thr Lys Ile Ile Cys Ala Gln Gln Cys Ser Gly Arg Cys Arg
210 215 220

Gly Lys Ser Pro Ser Asp Cys Cys His Asn Gln Cys Ala Ala Gly Cys
225 230 235 240

Thr Gly Pro Arg Glu Ser Asp Cys Leu Val Cys Arg Lys Phe Arg Asp
245 250 255

Glu Ala Thr Cys Lys Asp Thr Cys Pro Pro Leu Met Leu Tyr Asn Pro
260 265 270

Thr Thr Tyr Gln Met Asp Val Asn Pro Glu Gly Lys Tyr Ser Phe Gly
275 280 285

Ala Thr Cys Val Lys Lys Cys Pro Arg Asn Tyr Val Val Thr Asp His
290 295 300

Gly Ser Cys Val Arg Ala Cys Gly Ala Asp Ser Tyr Glu Met Glu Glu
305 310 315 320

Asp Gly Val Arg Lys Cys Lys Lys Cys Glu Gly Pro Cys Arg Lys Val
325 330 335

Cys Asn Gly Ile Gly Ile Gly Glu Phe Lys Asp Ser Leu Ser Ile Asn
340 345 350

Ala Thr Asn Ile Lys His Phe Lys Asn Cys Thr Ser Ile Ser Gly Asp
355 360 365

Leu His Ile Leu Pro Val Ala Phe Arg Gly Asp Ser Phe Thr His Thr

```
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800
```

```
Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Ala Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210
```

<210> SEQ ID NO 14
<211> LENGTH: 1068
<212> TYPE: PRT
<213> ORGANISM: Homo sapiens

<400> SEQUENCE: 14

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380
```

```
Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
```

```
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065


<210> SEQ ID NO 15
<211> LENGTH: 1068
<212> TYPE: PRT
<213> ORGANISM: Homo sapiens

<400> SEQUENCE: 15

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
```

```
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Lys Ile Thr
    530                 535                 540
```

```
Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975
```

```
Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065
```

<210> SEQ ID NO 16
<211> LENGTH: 1069
<212> TYPE: PRT
<213> ORGANISM: Homo sapiens

<400> SEQUENCE: 16

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285
```

```
Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Ala Gln Glu Lys Asp Phe Leu Trp Thr Thr Gly Lys His Tyr Cys Val
545                 550                 555                 560

Thr Ile Pro Glu Ile Leu Pro Lys Leu Leu Leu Ser Val Lys Trp Asn
                565                 570                 575

Ser Arg Asp Glu Val Ala Gln Met Tyr Cys Leu Val Lys Asp Trp Pro
            580                 585                 590

Pro Ile Lys Pro Glu Gln Ala Met Glu Leu Leu Asp Cys Asn Tyr Pro
        595                 600                 605

Asp Pro Met Val Arg Gly Phe Ala Val Arg Cys Leu Glu Lys Tyr Leu
    610                 615                 620

Thr Asp Asp Lys Leu Ser Gln Tyr Leu Ile Gln Leu Val Gln Val Leu
625                 630                 635                 640

Lys Tyr Glu Gln Tyr Leu Asp Asn Leu Leu Val Arg Phe Leu Leu Lys
                645                 650                 655

Lys Ala Leu Thr Asn Gln Arg Ile Gly His Phe Phe Phe Trp His Leu
            660                 665                 670

Lys Ser Glu Met His Asn Lys Thr Val Ser Gln Arg Phe Gly Leu Leu
        675                 680                 685

Leu Glu Ser Tyr Cys Arg Ala Cys Gly Met Tyr Leu Lys His Leu Asn
    690                 695                 700

Arg Gln Val Glu Ala Met Glu Lys Leu Ile Asn Leu Thr Asp Ile Leu
```

```
705                 710                 715                 720

Lys Gln Glu Lys Lys Asp Glu Thr Gln Lys Val Gln Met Lys Phe Leu
                725                 730                 735

Val Glu Gln Met Arg Arg Pro Asp Phe Met Asp Ala Leu Gln Gly Phe
            740                 745                 750

Leu Ser Pro Leu Asn Pro Ala His Gln Leu Gly Asn Leu Arg Leu Glu
        755                 760                 765

Glu Cys Arg Ile Met Ser Ser Ala Lys Arg Pro Leu Trp Leu Asn Trp
    770                 775                 780

Glu Asn Pro Asp Ile Met Ser Glu Leu Leu Phe Gln Asn Asn Glu Ile
785                 790                 795                 800

Ile Phe Lys Asn Gly Asp Asp Leu Arg Gln Asp Met Leu Thr Leu Gln
                805                 810                 815

Ile Ile Arg Ile Met Glu Asn Ile Trp Gln Asn Gln Gly Leu Asp Leu
            820                 825                 830

Arg Met Leu Pro Tyr Gly Cys Leu Ser Ile Gly Asp Cys Val Gly Leu
        835                 840                 845

Ile Glu Val Val Arg Asn Ser His Thr Ile Met Gln Ile Gln Cys Lys
    850                 855                 860

Gly Gly Leu Lys Gly Ala Leu Gln Phe Asn Ser His Thr Leu His Gln
865                 870                 875                 880

Trp Leu Lys Asp Lys Asn Lys Gly Glu Ile Tyr Asp Ala Ala Ile Asp
                885                 890                 895

Leu Phe Thr Arg Ser Cys Ala Gly Tyr Cys Val Ala Thr Phe Ile Leu
            900                 905                 910

Gly Ile Gly Asp Arg His Asn Ser Asn Ile Met Val Lys Asp Asp Gly
        915                 920                 925

Gln Leu Phe His Ile Asp Phe Gly His Phe Leu Asp His Lys Lys Lys
    930                 935                 940

Lys Phe Gly Tyr Lys Arg Glu Arg Val Pro Phe Val Leu Thr Gln Asp
945                 950                 955                 960

Phe Leu Ile Val Ile Ser Lys Gly Ala Gln Glu Cys Thr Lys Thr Arg
                965                 970                 975

Glu Phe Glu Arg Phe Gln Glu Met Cys Tyr Lys Ala Tyr Leu Ala Ile
            980                 985                 990

Arg Gln His Ala Asn Leu Phe Ile  Asn Leu Phe Ser Met  Met Leu Gly
        995                 1000                1005

Ser Gly  Met Pro Glu Leu Gln  Ser Phe Asp Asp Ile  Ala Tyr Ile
    1010                 1015                1020

Arg Lys  Thr Leu Ala Leu Asp  Lys Thr Glu Gln Glu  Ala Leu Glu
    1025                 1030                1035

Tyr Phe  Met Lys Gln Met Asn  Asp Ala His His Gly  Gly Trp Thr
    1040                 1045                1050

Thr Lys  Met Asp Trp Ile Phe  His Thr Ile Lys Gln  His Ala Leu
    1055                 1060                1065

Asn


<210> SEQ ID NO 17
<211> LENGTH: 1068
<212> TYPE: PRT
<213> ORGANISM: Homo sapiens

<400> SEQUENCE: 17

Met Pro Pro Arg Pro Ser Ser Gly Glu Leu Trp Gly Ile His Leu Met
1               5                   10                  15
```

```
Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
```

```
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860
```

```
Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala Leu His Gly Gly  Trp Thr Thr
    1040                1045                1050

Lys Met  Asp Trp Ile Phe His  Thr Ile Lys Gln His  Ala Leu Asn
    1055                1060                1065


<210> SEQ ID NO 18
<211> LENGTH: 766
<212> TYPE: PRT
<213> ORGANISM: Homo sapiens

<400> SEQUENCE: 18

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175
```

```
Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605
```

```
Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765


<210> SEQ ID NO 19
<211> LENGTH: 766
<212> TYPE: PRT
<213> ORGANISM: Homo sapiens

<400> SEQUENCE: 19

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220
```

```
Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Glu Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
```

```
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765


<210> SEQ ID NO 20
<211> LENGTH: 766
<212> TYPE: PRT
<213> ORGANISM: Homo sapiens

<400> SEQUENCE: 20

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
```

```
                260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Glu Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685
```

```
Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765


<210> SEQ ID NO 21
<211> LENGTH: 63
<212> TYPE: PRT
<213> ORGANISM: Homo sapiens

<400> SEQUENCE: 21

Glu Ala Tyr Val Met Ala Ser Val Asp Asn His Pro His Val Cys Arg
1               5                   10                  15

Leu Leu Gly Ile Cys Leu Thr Ser Thr Val Gln Leu Ile Thr Gln Leu
            20                  25                  30

Met Pro Phe Gly Cys Leu Leu Asp Tyr Val Arg Glu His Lys Asp Asn
        35                  40                  45

Ile Gly Ser Gln Tyr Leu Leu Asn Trp Cys Val Gln Ile Ala Lys
    50                  55                  60


<210> SEQ ID NO 22
<211> LENGTH: 24
<212> TYPE: DNA
<213> ORGANISM: Artificial
<220> FEATURE:
<223> OTHER INFORMATION: oligonucleotide primer

<400> SEQUENCE: 22

gggccatgtc tggcactgct ttcc                                            24


<210> SEQ ID NO 23
<211> LENGTH: 24
<212> TYPE: DNA
<213> ORGANISM: Artificial
<220> FEATURE:
<223> OTHER INFORMATION: oligonucleotide primer

<400> SEQUENCE: 23

gaaatataca gcttgcaagg actc                                            24


<210> SEQ ID NO 24
<211> LENGTH: 24
<212> TYPE: DNA
<213> ORGANISM: Artificial
<220> FEATURE:
<223> OTHER INFORMATION: oligonucleotide primer

<400> SEQUENCE: 24

aatatcagcc ttaggtgcgg ctcc                                            24


<210> SEQ ID NO 25
<211> LENGTH: 23
<212> TYPE: DNA
<213> ORGANISM: Artificial
<220> FEATURE:
<223> OTHER INFORMATION: oligonucleotide primer

<400> SEQUENCE: 25
```

gagaaaaggt gggcctgagg ttc 23

<210> SEQ ID NO 26
<211> LENGTH: 26
<212> TYPE: DNA
<213> ORGANISM: Artificial
<220> FEATURE:
<223> OTHER INFORMATION: oligonucleotide primer

<400> SEQUENCE: 26
ctgcgtaaac gtccctgtgc taggtc 26

<210> SEQ ID NO 27
<211> LENGTH: 25
<212> TYPE: DNA
<213> ORGANISM: Artificial
<220> FEATURE:
<223> OTHER INFORMATION: oligonucleotide primer

<400> SEQUENCE: 27
gcacgcacac acatatcccc atggc 25

<210> SEQ ID NO 28
<211> LENGTH: 24
<212> TYPE: DNA
<213> ORGANISM: Artificial
<220> FEATURE:
<223> OTHER INFORMATION: oligonucleotide primer

<400> SEQUENCE: 28
gcatgaacat gaccctgaat tcgg 24

<210> SEQ ID NO 29
<211> LENGTH: 24
<212> TYPE: DNA
<213> ORGANISM: Artificial
<220> FEATURE:
<223> OTHER INFORMATION: oligonucleotide primer

<400> SEQUENCE: 29
cctgcatgtg ttaaacaata cagc 24

<210> SEQ ID NO 30
<211> LENGTH: 23
<212> TYPE: DNA
<213> ORGANISM: Artificial
<220> FEATURE:
<223> OTHER INFORMATION: oligonucleotide primer

<400> SEQUENCE: 30
tcattcatga tcccactgcc ttc 23

<210> SEQ ID NO 31
<211> LENGTH: 23
<212> TYPE: DNA
<213> ORGANISM: Artificial
<220> FEATURE:
<223> OTHER INFORMATION: oligonucleotide primer

<400> SEQUENCE: 31
cagctgtttg gctaagagca gcc 23

<210> SEQ ID NO 32
<211> LENGTH: 28
<212> TYPE: DNA
<213> ORGANISM: Artificial

<220> FEATURE:
<223> OTHER INFORMATION: oligonucleotide primer

<400> SEQUENCE: 32
ctgtaaatca tctgtgaatc cagagggg 28

<210> SEQ ID NO 33
<211> LENGTH: 34
<212> TYPE: DNA
<213> ORGANISM: Artificial
<220> FEATURE:
<223> OTHER INFORMATION: oligonucleotide primer

<400> SEQUENCE: 33
gtaaattctg ctttatttat tccaataggt atgg 34

<210> SEQ ID NO 34
<211> LENGTH: 35
<212> TYPE: DNA
<213> ORGANISM: Artificial
<220> FEATURE:
<223> OTHER INFORMATION: oligonucleotide primer

<400> SEQUENCE: 34
ctacgaaagc ctctctaatt ttgtgacatt tgagc 35

<210> SEQ ID NO 35
<211> LENGTH: 36
<212> TYPE: DNA
<213> ORGANISM: Artificial
<220> FEATURE:
<223> OTHER INFORMATION: oligonucleotide primer

<400> SEQUENCE: 35
cttgctgtaa attctaatgc tgttcatgga ttgtgc 36

<210> SEQ ID NO 36
<211> LENGTH: 29
<212> TYPE: DNA
<213> ORGANISM: Artificial
<220> FEATURE:
<223> OTHER INFORMATION: oligonucleotide primer

<400> SEQUENCE: 36
ggggatctct tcctgtatcc ctctcaggc 29

<210> SEQ ID NO 37
<211> LENGTH: 29
<212> TYPE: DNA
<213> ORGANISM: Artificial
<220> FEATURE:
<223> OTHER INFORMATION: oligonucleotide primer

<400> SEQUENCE: 37
gtttattgat gcgaacagtg aatatttcc 29

<210> SEQ ID NO 38
<211> LENGTH: 21
<212> TYPE: DNA
<213> ORGANISM: Artificial
<220> FEATURE:
<223> OTHER INFORMATION: oligonucleotide primer

<400> SEQUENCE: 38
cataatgctt gctctgatag g 21

<210> SEQ ID NO 39
<211> LENGTH: 20
<212> TYPE: DNA
<213> ORGANISM: Artificial
<220> FEATURE:
<223> OTHER INFORMATION: oligonucleotide primer

<400> SEQUENCE: 39
gtaactcagc agcatctcag 20

<210> SEQ ID NO 40
<211> LENGTH: 3633
<212> TYPE: DNA
<213> ORGANISM: Homo sapiens

<400> SEQUENCE: 40
atgcgaccct ccgggacggc cggggcagcg ctcctggcgc tgctggctgc gctctgcccg 60
gcgagtcggg ctctggagga aaagaaagtt tgccaaggca cgagtaacaa gctcacgcag 120
ttgggcactt ttgaagatca ttttctcagc ctccagagga tgttcaataa ctgtgaggtg 180
gtccttggga atttggaaat tacctatgtg cagaggaatt atgatctttc cttcttaaag 240
accatccagg aggtggctgg ttatgtcctc attgccctca acacagtgga gcgaattcct 300
ttggaaaacc tgcagatcat cagaggaaat atgtactacg aaaattccta tgccttagca 360
gtcttatcta actatgatgc aaataaaacc ggactgaagg agctgcccat gagaaattta 420
caggaaatcc tgcatggcgc cgtgcggttc agcaacaacc ctgccctgtg caacgtggag 480
agcatccagt ggcgggacat agtcagcagt gactttctca gcaacatgtc gatggacttc 540
cagaaccacc tgggcagctg ccaaaagtgt gatccaagct gtcccaatgg gagctgctgg 600
ggtgcaggag aggagaactg ccagaaactg accaaaatca tctgtgccca gcagtgctcc 660
gggcgctgcc gtggcaagtc ccccagtgac tgctgccaca accagtgtgc tgcaggctgc 720
acaggccccc gggagagcga ctgcctggtc tgccgcaaat tccgagacga agccacgtgc 780
aaggacacct gcccccact catgctctac aaccccacca cgtaccagat ggatgtgaac 840
cccgagggca aatacagctt tggtgccacc tgcgtgaaga agtgtccccg taattatgtg 900
gtgacagatc acggctcgtg cgtccgagcc tgtggggccg acagctatga gatggaggaa 960
gacggcgtcc gcaagtgtaa gaagtgcgaa gggccttgcc gcaaagtgtg taacggaata 1020
ggtattggtg aatttaaaga ctcactctcc ataaatgcta cgaatattaa acacttcaaa 1080
aactgcacct ccatcagtgg cgatctccac atcctgccgg tggcatttag ggtgactcc 1140 ttcacacata ctcctcctct ggatccacag gaactggata ttctgaaaac cgtaaaggaa 1200
atcacagggt ttttgctgat tcaggcttgg cctgaaaaca ggacggacct ccatgccttt 1260
gagaacctag aaatcatacg cggcaggacc aagcaacatg gtcagttttc tcttgcagtc 1320
gtcagcctga acataacatc cttgggatta cgctccctca aggagataag tgatggagat 1380
gtgataattt caggaaacaa aaatttgtgc tatgcaaata caataaactg gaaaaaactg 1440
tttgggacct ccggtcagaa aaccaaaatt ataagcaaca gaggtgaaaa cagctgcaag 1500
gccacaggcc aggtctgcca tgccttgtgc tcccccgagg gctgctgggg cccggagccc 1560
agggactgcg tctcttgccg gaatgtcagc cgaggcaggg aatgcgtgga caagtgcaag 1620
cttctggagg gtgagccaag ggagtttgtg gagaactctg agtgcataca gtgccaccca 1680
gagtgcctgc ctcaggccat gaacatcacc tgcacaggac ggggaccaga caactgtatc 1740
cagtgtgccc actacattga cggcccccac tgcgtcaaga cctgcccggc aggagtcatg 1800
ggagaaaaca acaccctggt ctggaagtac gcagacgccg gccatgtgtg ccacctgtgc 1860

```
catccaaact gcacctacgg atgcactggg ccaggtcttg aaggctgtcc aacgaatggg   1920

cctaagatcc cgtccatcgc cactgggatg gtgggggccc tcctcttgct gctggtggtg   1980

gccctgggga tcggcctctt catgcgaagg cgccacatcg ttcggaagcg cacgctgcgg   2040

aggctgctgc aggagaggga gcttgtggag cctcttacac ccagtggaga agctcccaac   2100

cacgctctct tgaggatctt gaaggaaact gaattcaaaa agatcaaagt gctgggctcc   2160

ggtgcgttcg gcacggtgta taagggactc tggatcccag aaggtgagaa agttaaaatt   2220

cccgtcgcta tcaaggaatt aagagaagca acatctccga aagccaacaa ggaaatcctc   2280

gatgaagcct acgtgatggc cagcgtggac aacccccacg tgtgccgcct gctgggcatc   2340

tgcctcacct ccaccgtgca actcatcacg cagctcatgc ccttcggctg cctcctggac   2400

tatgtccggg aacacaaaga caatattggc tcccagtacc tgctcaactg gtgtgtgcag   2460

atcgcaaagg gcatgaacta cttggaggac cgtcgcttgg tgcaccgcga cctggcagcc   2520

aggaacgtac tggtgaaaac accgcagcat gtcaagatca cagattttgg gctggccaaa   2580

ctgctgggtg cggaagagaa agaataccat gcagaaggag gcaaagtgcc tatcaagtgg   2640

atggcattgg aatcaatttt acacagaatc tatacccacc agagtgatgt ctggagctac   2700

ggggtgaccg tttgggagtt gatgaccttt ggatccaagc catatgacgg aatccctgcc   2760

agcgagatct cctccatcct ggagaaagga gaacgcctcc ctcagccacc catatgtacc   2820

atcgatgtct acatgatcat ggtcaagtgc tggatgatag acgcagatag tcgcccaaag   2880

ttccgtgagt tgatcatcga attctccaaa atggcccgag acccccagcg ctaccttgtc   2940

attcaggggg atgaaagaat gcatttgcca agtcctacag actccaactt ctaccgtgcc   3000

ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 41
<211> LENGTH: 3633
<212> TYPE: DNA
<213> ORGANISM: Homo sapiens

<400> SEQUENCE: 41

```
atgcgaccct ccgggacggc cggggcagcg ctcctggcgc tgctggctgc gctctgcccg     60

gcgagtcggg ctctggagga aaagaaagtt tgccaaggca cgagtaacaa gctcacgcag    120

ttgggcactt ttgaagatca ttttctcagc ctccagagga tgttcaataa ctgtgaggtg    180

gtccttggga atttggaaat tacctatgtg cagaggaatt atgatctttc cttcttaaag    240

accatccagg aggtggctgg ttatgtcctc attgccctca acacagtgga gcgaattcct    300

ttggaaaacc tgcagatcat cagaggaaat atgtactacg aaaattccta tgccttagca    360
```

```
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gcccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggtgactcc    1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcctgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
```

```
agcgagatct cctccatcct ggagaaagga gaacgcctcc ctcagccacc catatgtacc   2820

atcgatgtct acatgatcat ggtcaagtgc tggatgatag acgcagatag tcgcccaaag   2880

ttccgtgagt tgatcatcga attctccaaa atggcccgag acccccagcg ctaccttgtc   2940

attcaggggg atgaaagaat gcatttgcca agtcctacag actccaactt ctaccgtgcc   3000

ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 42
<211> LENGTH: 3618
<212> TYPE: DNA
<213> ORGANISM: Homo sapiens

<400> SEQUENCE: 42

```
atgcgaccct ccgggacggc cggggcagcg ctcctggcgc tgctggctgc gctctgcccg     60

gcgagtcggg ctctggagga aaagaaagtt tgccaaggca cgagtaacaa gctcacgcag    120

ttgggcactt ttgaagatca ttttctcagc ctccagagga tgttcaataa ctgtgaggtg    180

gtccttggga atttggaaat tacctatgtg cagaggaatt atgatctttc cttcttaaag    240

accatccagg aggtggctgg ttatgtcctc attgccctca acacagtgga gcgaattcct    300

ttggaaaacc tgcagatcat cagaggaaat atgtactacg aaaattccta tgccttagca    360

gtcttatcta actatgatgc aaataaaacc ggactgaagg agctgcccat gagaaattta    420

caggaaatcc tgcatggcgc cgtgcggttc agcaacaacc ctgccctgtg caacgtggag    480

agcatccagt ggcgggacat agtcagcagt gactttctca gcaacatgtc gatggacttc    540

cagaaccacc tgggcagctg ccaaaagtgt gatccaagct gtcccaatgg gagctgctgg    600

ggtgcaggag aggagaactg ccagaaactg accaaaatca tctgtgccca gcagtgctcc    660

gggcgctgcc gtggcaagtc ccccagtgac tgctgccaca accagtgtgc tgcaggctgc    720

acaggccccc gggagagcga ctgcctggtc tgccgcaaat tccgagacga agccacgtgc    780

aaggacacct gcccccccact catgctctac aaccccacca cgtaccagat ggatgtgaac    840

cccgagggca aatacagctt tggtgccacc tgcgtgaaga agtgtccccg taattatgtg    900

gtgacagatc acggctcgtg cgtccgagcc tgtggggccg acagctatga gatggaggaa    960

gacggcgtcc gcaagtgtaa gaagtgcgaa gggccttgcc gcaaagtgtg taacggaata   1020

ggtattggtg aatttaaaga ctcactctcc ataaatgcta cgaatattaa acacttcaaa   1080

aactgcacct ccatcagtgg cgatctccac atcctgccgg tggcatttag ggggtgactcc  1140

ttcacacata ctcctcctct ggatccacag gaactggata ttctgaaaac cgtaaaggaa   1200

atcacagggt ttttgctgat tcaggcttgg cctgaaaaca ggacggacct ccatgccttt   1260
```

```
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaaacatc tccgaaagcc aacaaggaaa tcctcgatga agcctacgtg   2280
atggccagcg tggacaaccc ccacgtgtgc cgcctgctgg gcatctgcct cacctccacc   2340
gtgcaactca tcacgcagct catgcccttc ggctgcctcc tggactatgt ccgggaacac   2400
aaagacaata ttggctccca gtacctgctc aactggtgtg tgcagatcgc aaagggcatg   2460
aactacttgg aggaccgtcg cttggtgcac cgcgacctgg cagccaggaa cgtactggtg   2520
aaaacaccgc agcatgtcaa gatcacagat tttgggctgg ccaaactgct gggtgcggaa   2580
gagaaagaat accatgcaga aggaggcaaa gtgcctatca agtggatggc attggaatca   2640
attttacaca gaatctatac ccaccagagt gatgtctgga gctacggggt gaccgtttgg   2700
gagttgatga cctttggatc caagccatat gacggaatcc ctgccagcga gatctcctcc   2760
atcctggaga aaggagaacg cctccctcag ccacccatat gtaccatcga tgtctacatg   2820
atcatggtca agtgctggat gatagacgca gatagtcgcc caaagttccg tgagttgatc   2880
atcgaattct ccaaaatggc ccgagacccc cagcgctacc ttgtcattca ggggggatgaa   2940
agaatgcatt tgccaagtcc tacagactcc aacttctacc gtgccctgat ggatgaagaa   3000
gacatggacg acgtggtgga tgccgacgag tacctcatcc cacagcaggg cttcttcagc   3060
agcccctcca cgtcacggac tcccctcctg agctctctga gtgcaaccag caacaattcc   3120
accgtggctt gcattgatag aaatgggctg caaagctgtc ccatcaagga agacagcttc   3180
ttgcagcgat acagctcaga ccccacaggc gccttgactg aggacagcat agacgacacc   3240
ttcctcccag tgcctgaata cataaaccag tccgttccca aaaggcccgc tggctctgtg   3300
cagaatcctg tctatcacaa tcagcctctg aaccccgcgc ccagcagaga cccacactac   3360
caggaccccc acagcactgc agtgggcaac cccgagtatc tcaacactgt ccagcccacc   3420
tgtgtcaaca gcacattcga cagccctgcc cactgggccc agaaaggcag ccaccaaatt   3480
agcctggaca accctgacta ccagcaggac ttctttccca aggaagccaa gccaaatggc   3540
atctttaagg gctccacagc tgaaaatgca gaatacctaa gggtcgcgcc acaaagcagt   3600
gaatttattg gagcatga                                                  3618
```

<210> SEQ ID NO 43
<211> LENGTH: 3633
<212> TYPE: DNA
<213> ORGANISM: Homo sapiens

<400> SEQUENCE: 43

```
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gcccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggggtgactcc  1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
```

```
ggtgcgttcg gcacggtgta taagggactc tggatcccag aaggtgagaa agttaaaatt   2220

cccgtcgcta tcaatgaatt aagagaagca acatctccga aagccaacaa ggaaatcctc   2280

gatgaagcct acgtgatggc cagcgtggac aacccccacg tgtgccgcct gctgggcatc   2340

tgcctcacct ccaccgtgca actcatcacg cagctcatgc ccttcggctg cctcctggac   2400

tatgtccggg aacacaaaga caatattggc tcccagtacc tgctcaactg gtgtgtgcag   2460

atcgcaaagg gcatgaacta cttggaggac cgtcgcttgg tgcaccgcga cctggcagcc   2520

aggaacgtac tggtgaaaac accgcagcat gtcaagatca cagattttgg gctggccaaa   2580

ctgctgggtg cggaagagaa agaataccat gcagaaggag gcaaagtgcc tatcaagtgg   2640

atggcattgg aatcaatttt acacagaatc tatacccacc agagtgatgt ctggagctac   2700

ggggtgaccg tttgggagtt gatgaccttt ggatccaagc catatgacgg aatccctgcc   2760

agcgagatct cctccatcct ggagaaagga gaacgcctcc ctcagccacc catatgtacc   2820

atcgatgtct acatgatcat ggtcaagtgc tggatgatag acgcagatag tcgcccaaag   2880

ttccgtgagt tgatcatcga attctccaaa atggcccgag acccccagcg ctaccttgtc   2940

attcaggggg atgaaagaat gcatttgcca agtcctacag actccaactt ctaccgtgcc   3000

ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 44
<211> LENGTH: 3633
<212> TYPE: DNA
<213> ORGANISM: Homo sapiens

<400> SEQUENCE: 44

```
atgcgaccct ccgggacggc cggggcagcg ctcctggcgc tgctggctgc gctctgcccg     60

gcgagtcggg ctctggagga aaagaaagtt tgccaaggca cgagtaacaa gctcacgcag    120

ttgggcactt ttgaagatca ttttctcagc ctccagagga tgttcaataa ctgtgaggtg    180

gtccttggga atttggaaat tacctatgtg cagaggaatt atgatctttc cttcttaaag    240

accatccagg aggtggctgg ttatgtcctc attgccctca acacagtgga gcgaattcct    300

ttggaaaacc tgcagatcat cagaggaaat atgtactacg aaaattccta tgccttagca    360

gtcttatcta actatgatgc aaataaaacc ggactgaagg agctgcccat gagaaattta    420

caggaaatcc tgcatggcgc cgtgcggttc agcaacaacc ctgccctgtg caacgtggag    480

agcatccagt ggcgggacat agtcagcagt gactttctca gcaacatgtc gatggacttc    540

cagaaccacc tgggcagctg ccaaaagtgt gatccaagct gtcccaatgg gagctgctgg    600

ggtgcaggag aggagaactg ccagaaactg accaaaatca tctgtgccca gcagtgctcc    660
```

```
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggtgactcc    1140
ttcacacata ctcctcctct ggatccacag gaactggata ttctgaaaac cgtaaaggaa   1200
atcacagggt tttgctgat tcaggcttgg cctgaaaaca ggacggacct ccatgccttt    1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
cgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
```

cagggcttct tcagcagccc ctccacgtca cggactcccc tcctgagctc tctgagtgca 3120
accagcaaca attccaccgt ggcttgcatt gatagaaatg ggctgcaaag ctgtcccatc 3180
aaggaagaca gcttcttgca gcgatacagc tcagacccca caggcgcctt gactgaggac 3240
agcatagacg acaccttcct cccagtgcct gaatacataa accagtccgt tcccaaaagg 3300
cccgctggct ctgtgcagaa tcctgtctat cacaatcagc ctctgaaccc cgcgcccagc 3360
agagacccac actaccagga cccccacagc actgcagtgg gcaaccccga gtatctcaac 3420
actgtccagc ccacctgtgt caacagcaca ttcgacagcc ctgcccactg ggcccagaaa 3480
ggcagccacc aaattagcct ggacaaccct gactaccagc aggacttctt tcccaaggaa 3540
gccaagccaa atggcatctt taagggctcc acagctgaaa atgcagaata cctaagggtc 3600
gcgccacaaa gcagtgaatt tattggagca tga 3633

<210> SEQ ID NO 45
<211> LENGTH: 3633
<212> TYPE: DNA
<213> ORGANISM: Homo sapiens

<400> SEQUENCE: 45
atgcgaccct ccgggacggc cggggcagcg ctcctggcgc tgctggctgc gctctgcccg 60
gcgagtcggg ctctggagga aaagaaagtt tgccaaggca cgagtaacaa gctcacgcag 120
ttgggcactt ttgaagatca ttttctcagc ctccagagga tgttcaataa ctgtgaggtg 180
gtccttggga atttggaaat tacctatgtg cagaggaatt atgatctttc cttcttaaag 240
accatccagg aggtggctgg ttatgtcctc attgccctca acacagtgga gcgaattcct 300
ttggaaaacc tgcagatcat cagaggaaat atgtactacg aaaattccta tgccttagca 360
gtcttatcta actatgatgc aaataaaacc ggactgaagg agctgcccat gagaaattta 420
caggaaatcc tgcatggcgc cgtgcggttc agcaacaacc ctgccctgtg caacgtggag 480
agcatccagt ggcgggacat agtcagcagt gactttctca gcaacatgtc gatggacttc 540
cagaaccacc tgggcagctg ccaaaagtgt gatccaagct gtcccaatgg gagctgctgg 600
ggtgcaggag aggagaactg ccagaaactg accaaaatca tctgtgccca gcagtgctcc 660
gggcgctgcc gtggcaagtc ccccagtgac tgctgccaca accagtgtgc tgcaggctgc 720
acaggccccc gggagagcga ctgcctggtc tgccgcaaat tccgagacga agccacgtgc 780
aaggacacct gccccccact catgctctac aaccccacca cgtaccagat ggatgtgaac 840
cccgagggca aatacagctt tggtgccacc tgcgtgaaga agtgtccccg taattatgtg 900
gtgacagatc acggctcgtg cgtccgagcc tgtggggccg acagctatga gatggaggaa 960
gacggcgtcc gcaagtgtaa gaagtgcgaa gggccttgcc gcaaagtgtg taacggaata 1020
ggtattggtg aatttaaaga ctcactctcc ataaatgcta cgaatattaa acacttcaaa 1080
aactgcacct ccatcagtgg cgatctccac atcctgccgg tggcatttag ggggtgactcc 1140
ttcacacata ctcctcctct ggatccacag gaactggata ttctgaaaac cgtaaaggaa 1200
atcacagggt ttttgctgat tcaggcttgg cctgaaaaca ggacggacct ccatgccttt 1260
gagaacctag aaatcatacg cggcaggacc aagcaacatg gtcagttttc tcttgcagtc 1320
gtcagcctga acataacatc cttgggatta cgctccctca aggagataag tgatggagat 1380
gtgataattt caggaaacaa aaatttgtgc tatgcaaata caataaactg gaaaaaactg 1440
tttgggacct ccggtcagaa aaccaaaatt ataagcaaca gaggtgaaaa cagctgcaag 1500
gccacaggcc aggtctgcca tgccttgtgc tcccccgagg gctgctgggg cccggagccc 1560

```
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcatg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
accagcaaca attccaccgt ggcttgcatt gatagaaatg ggctgcaaag ctgtcccatc   3180
aaggaagaca gcttcttgca gcgatacagc tcagacccca caggcgcctt gactgaggac   3240
agcatagacg acaccttcct cccagtgcct gaatacataa accagtccgt tcccaaaagg   3300
cccgctggct ctgtgcagaa tcctgtctat cacaatcagc ctctgaaccc cgcgcccagc   3360
agagacccac actaccagga cccccacagc actgcagtgg gcaaccccga gtatctcaac   3420
actgtccagc ccacctgtgt caacagcaca ttcgacagcc ctgcccactg ggcccagaaa   3480
ggcagccacc aaattagcct ggacaaccct gactaccagc aggacttctt tcccaaggaa   3540
gccaagccaa atggcatctt taagggctcc acagctgaaa atgcagaata cctaagggtc   3600
gcgccacaaa gcagtgaatt tattggagca tga                                3633
```

<210> SEQ ID NO 46
<211> LENGTH: 3636
<212> TYPE: DNA
<213> ORGANISM: Homo sapiens

<400> SEQUENCE: 46

```
atgcgaccct ccgggacggc cggggcagcg ctcctggcgc tgctggctgc gctctgcccg     60
```

```
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gcccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggtgactcc    1140
ttcacacata ctcctcctct ggatccacag gaactggata ttctgaaaac cgtaaaggaa   1200
atcacagggt tttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccacccc acgtgtgccg cctgctgggc   2340
atctgcctca cctccaccgt gcaactcatc acgcagctca tgcccttcgg ctgcctcctg   2400
gactatgtcc gggaacacaa agacaatatt ggctcccagt acctgctcaa ctggtgtgtg   2460
```

cagatcgcaa agggcatgaa ctacttggag gaccgtcgct tggtgcaccg cgacctggca 2520
gccaggaacg tactggtgaa aacaccgcag catgtcaaga tcacagattt tgggctggcc 2580
aaactgctgg gtgcggaaga gaaagaatac catgcagaag gaggcaaagt gcctatcaag 2640
tggatggcat tggaatcaat tttacacaga atctataccc accagagtga tgtctggagc 2700
tacggggtga ccgtttggga gttgatgacc tttggatcca agccatatga cggaatccct 2760
gccagcgaga tctcctccat cctggagaaa ggagaacgcc tccctcagcc acccatatgt 2820
accatcgatg tctacatgat catggtcaag tgctggatga tagacgcaga tagtcgccca 2880
aagttccgtg agttgatcat cgaattctcc aaaatggccc gagacccccca gcgctacctt 2940 gtcattcagg gggatgaaag aatgcatttg ccaagtccta cagactccaa cttctaccgt 3000
gccctgatgg atgaagaaga catggacgac gtggtggatg ccgacgagta cctcatccca 3060
cagcagggct tcttcagcag cccctccacg tcacggactc ccctcctgag ctctctgagt 3120
gcaaccagca acaattccac cgtggcttgc attgatagaa atgggctgca aagctgtccc 3180
atcaaggaag acagcttctt gcagcgatac agctcagacc ccacaggcgc cttgactgag 3240
gacagcatag acgacacctt cctcccagtg cctgaataca taaaccagtc cgttcccaaa 3300
aggcccgctg gctctgtgca gaatcctgtc tatcacaatc agcctctgaa ccccgcgccc 3360
agcagagacc cacactacca ggacccccac agcactgcag tgggcaaccc cgagtatctc 3420
aacactgtcc agcccacctg tgtcaacagc acattcgaca gccctgccca ctgggcccag 3480
aaaggcagcc accaaattag cctggacaac cctgactacc agcaggactt ctttcccaag 3540
gaagccaagc caaatggcat ctttaagggc tccacagctg aaaatgcaga atacctaagg 3600
gtcgcgccac aaagcagtga atttattgga gcatga 3636

<210> SEQ ID NO 47
<211> LENGTH: 3633
<212> TYPE: DNA
<213> ORGANISM: Homo sapiens

<400> SEQUENCE: 47
atgcgaccct ccgggacggc cggggcagcg ctcctggcgc tgctggctgc gctctgcccg 60
gcgagtcggg ctctggagga aaagaaagtt tgccaaggca cgagtaacaa gctcacgcag 120
ttgggcactt ttgaagatca ttttctcagc ctccagagga tgttcaataa ctgtgaggtg 180
gtccttggga atttggaaat tacctatgtg cagaggaatt atgatctttc cttcttaaag 240
accatccagg aggtggctgg ttatgtcctc attgccctca acacagtgga gcgaattcct 300
ttggaaaacc tgcagatcat cagaggaaat atgtactacg aaaattccta tgccttagca 360
gtcttatcta actatgatgc aaataaaacc ggactgaagg agctgcccat gagaaattta 420
caggaaatcc tgcatggcgc cgtgcggttc agcaacaacc ctgccctgtg caacgtggag 480
agcatccagt ggcgggacat agtcagcagt gactttctca gcaacatgtc gatggacttc 540
cagaaccacc tgggcagctg ccaaaagtgt gatccaagct gtcccaatgg gagctgctgg 600
ggtgcaggag aggagaactg ccagaaactg accaaaatca tctgtgccca gcagtgctcc 660
gggcgctgcc gtggcaagtc ccccagtgac tgctgccaca accagtgtgc tgcaggctgc 720
acaggccccc gggagagcga ctgcctggtc tgccgcaaat tccgagacga agccacgtgc 780
aaggacacct gccccccact catgctctac aaccccacca cgtaccagat ggatgtgaac 840
cccgagggca aatacagctt tggtgccacc tgcgtgaaga agtgtccccg taattatgtg 900
gtgacagatc acggctcgtg cgtccgagcc tgtggggccg acagctatga gatggaggaa 960

```
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggtgactcc    1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcggcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
accagcaaca attccaccgt ggcttgcatt gatagaaatg ggctgcaaag ctgtcccatc   3180
aaggaagaca gcttcttgca gcgatacagc tcagacccca caggcgcctt gactgaggac   3240
agcatagacg acaccttcct cccagtgcct gaatacataa accagtccgt tcccaaaagg   3300
cccgctggct ctgtgcagaa tcctgtctat cacaatcagc ctctgaaccc cgcgcccagc   3360
```

```
agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 48
<211> LENGTH: 3633
<212> TYPE: DNA
<213> ORGANISM: Homo sapiens

<400> SEQUENCE: 48

```
atgcgaccct ccgggacggc cggggcagcg ctcctggcgc tgctggctgc gctctgcccg     60

gcgagtcggg ctctggagga aaagaaagtt tgccaaggca cgagtaacaa gctcacgcag    120

ttgggcactt ttgaagatca ttttctcagc ctccagagga tgttcaataa ctgtgaggtg    180

gtccttggga atttggaaat tacctatgtg cagaggaatt atgatctttc cttcttaaag    240

accatccagg aggtggctgg ttatgtcctc attgccctca acacagtgga gcgaattcct    300

ttggaaaacc tgcagatcat cagaggaaat atgtactacg aaaattccta tgccttagca    360

gtcttatcta actatgatgc aaataaaacc ggactgaagg agctgcccat gagaaattta    420

caggaaatcc tgcatggcgc cgtgcggttc agcaacaacc ctgccctgtg caacgtggag    480

agcatccagt ggcgggacat agtcagcagt gactttctca gcaacatgtc gatggacttc    540

cagaaccacc tgggcagctg ccaaaagtgt gatccaagct gtcccaatgg gagctgctgg    600

ggtgcaggag aggagaactg ccagaaactg accaaaatca tctgtgccca gcagtgctcc    660

gggcgctgcc gtggcaagtc ccccagtgac tgctgccaca accagtgtgc tgcaggctgc    720

acaggccccc gggagagcga ctgcctggtc tgccgcaaat tccgagacga agccacgtgc    780

aaggacacct gcccccccact catgctctac aaccccacca cgtaccagat ggatgtgaac   840

cccgagggca aatacagctt tggtgccacc tgcgtgaaga agtgtccccg taattatgtg    900

gtgacagatc acggctcgtg cgtccgagcc tgtggggccg acagctatga gatggaggaa    960

gacggcgtcc gcaagtgtaa gaagtgcgaa gggccttgcc gcaaagtgtg taacggaata   1020

ggtattggtg aatttaaaga ctcactctcc ataaatgcta cgaatattaa acacttcaaa   1080

aactgcacct ccatcagtgg cgatctccac atcctgccgg tggcatttag ggtgactcc    1140

ttcacacata ctcctcctct ggatccacag gaactggata ttctgaaaac cgtaaaggaa   1200

atcacagggt ttttgctgat tcaggcttgg cctgaaaaca ggacggacct ccatgccttt   1260

gagaacctag aaatcatacg cggcaggacc aagcaacatg gtcagttttc tcttgcagtc   1320

gtcagcctga acataacatc cttgggatta cgctccctca aggagataag tgatggagat   1380

gtgataattt caggaaacaa aaatttgtgc tatgcaaata caataaactg gaaaaaactg   1440

tttgggacct ccggtcagaa aaccaaaatt ataagcaaca gaggtgaaaa cagctgcaag   1500

gccacaggcc aggtctgcca tgccttgtgc tcccccgagg gctgctgggg cccggagccc   1560

agggactgcg tctcttgccg gaatgtcagc cgaggcaggg aatgcgtgga caagtgcaag   1620

cttctggagg gtgagccaag ggagtttgtg gagaactctg agtgcataca gtgccaccca   1680

gagtgcctgc ctcaggccat gaacatcacc tgcacaggac ggggaccaga caactgtatc   1740

cagtgtgccc actacattga cggcccccac tgcgtcaaga cctgcccggc aggagtcatg   1800

ggagaaaaca acaccctggt ctggaagtac gcagacgccg gccatgtgtg ccacctgtgc   1860
```

```
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggccaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
accagcaaca attccaccgt ggcttgcatt gatagaaatg ggctgcaaag ctgtcccatc   3180
aaggaagaca gcttcttgca gcgatacagc tcagacccca caggcgcctt gactgaggac   3240
agcatagacg acaccttcct cccagtgcct gaatacataa accagtccgt tcccaaaagg   3300
cccgctggct ctgtgcagaa tcctgtctat cacaatcagc ctctgaaccc cgcgcccagc   3360
agagacccac actaccagga cccccacagc actgcagtgg gcaaccccga gtatctcaac   3420
actgtccagc ccacctgtgt caacagcaca ttcgacagcc ctgcccactg ggcccagaaa   3480
ggcagccacc aaattagcct ggacaaccct gactaccagc aggacttctt tcccaaggaa   3540
gccaagccaa atggcatctt taagggctcc acagctgaaa atgcagaata cctaagggtc   3600
gcgccacaaa gcagtgaatt tattggagca tga                                3633
```

<210> SEQ ID NO 49
<211> LENGTH: 3633
<212> TYPE: DNA
<213> ORGANISM: Homo sapiens

<400> SEQUENCE: 49

```
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
```

```
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gcccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggtgactcc    1140
ttcacacata ctcctcctct ggatccacag gaactggata ttctgaaaac cgtaaaggaa   1200
atcacagggt tttgctgat tcaggcttgg cctgaaaaca ggacggacct ccatgccttt    1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccctt ggatccaagc catatgacgg aatccctgcc   2760
```

```
agcgagatct cctccatcct ggagaaagga gaacgcctcc ctcagccacc catatgtacc   2820

atcgatgtct acatgatcat ggtcaagtgc tggatgatag acgcagatag tcgcccaaag   2880

ttccgtgagt tgatcatcga attctccaaa atggcccgag acccccagcg ctaccttgtc   2940

attcaggggg atgaaagaat gcatttgcca agtcctacag actccaactt ctaccgtgcc   3000

ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                              3633
```

<210> SEQ ID NO 50
<211> LENGTH: 3210
<212> TYPE: DNA
<213> ORGANISM: Homo sapiens

<400> SEQUENCE: 50

```
atgcctccaa gaccatcatc aggtgaactg tggggcatcc acttgatgcc cccaagaatc     60

ctagtagaat gtttactacc aaatggaatg atagtgactt tagaatgcct ccgtgaggct    120

acattaataa ccataaagca tgaactattt aaagaagcaa gaaaataccc cctccatcaa    180

cttcttcaag atgaatcttc ttacattttc gtaagtgtta cccaagaagc agaaagggaa    240

gaattttttg atgaaacaag acgactttgt gaccttcggc tttttcaacc ctttttaaaa    300

gtaattgaac cagtaggcaa ccgtgaagaa aagatcctca atcgagaaat tggttttgct    360

atcggcatgc cagtgtgtga atttgatatg gttaaagatc cagaagtaca ggacttccga    420

agaaatattc tgaacgtttg taaagaagct gtggatctta gggacctcaa ttcacctcat    480

agtagagcaa tgtatgtcta tcctccaaat gtagaatctt caccagaatt gccaaagcac    540

atatataata aattagataa agggcaaata atagtggtga tctgggtaat agtttctcca    600

aataatgaca agcagaagta tactctgaaa atcaaccatg actgtgtacc agaacaagta    660

attgctgaag caatcaggaa aaaaactcga agtatgttgc tatcctctga acaactaaaa    720

ctctgtgttt tagaatatca gggcaagtat attttaaaag tgtgtggatg tgatgaatac    780

ttcctagaaa aatatcctct gagtcagtat aagtatataa gaagctgtat aatgcttggg    840

aggatgccca atttgatgtt gatggctaaa gaaagcctct attctcaact gccaatggac    900

tgttttacaa tgccatctta ttccagacgc atttccacag ctacaccata tatgaatgga    960

gaaacatcta caaaatccct ttgggttata aatagtgcac tcagaataaa aattctttgt   1020

gcaacctacg tgaatgtaaa tattcgagac attgataaga tctatgttcg aacaggtatc   1080

taccatggag gagaaccctt atgtgacaat gtgaacactc aaagagtacc ttgttccaat   1140

cccaggtgga atgaatggct gaattatgat atatacattc ctgatcttcc tcgtgctgct   1200

cgactttgcc tttccatttg ctctgttaaa ggccgaaagg gtgctaaaga ggaacactgt   1260
```

```
ccattggcat ggggaaatat aaacttgttt gattacacag acactctagt atctggaaaa   1320

atggctttga atctttggcc agtacctcat ggactagaag atttgctgaa ccctattggt   1380

gttactggat caaatccaaa taaagaaact ccatgcttag agttggagtt tgactggttc   1440

agcagtgtgg taaagttccc agatatgtca gtgattgaag agcatgccaa ttggtctgta   1500

tcccgagaag caggatttag ctattcccac gcaggactga gtaacagact agctagagac   1560

aatgaattaa gggaaaatga caaagaacag ctcaaagcaa tttctacacg agatcctctc   1620

tctgaaatca ctgcgcagga gaaagatttt ctatggacca caggtaaaca ctattgtgta   1680

actatccccg aaattctacc caaattgctt ctgtctgtta aatggaattc tagagatgaa   1740

gtagcccaga tgtattgctt ggtaaaagat tggcctccaa tcaaacctga acaggctatg   1800

gaacttctgg actgtaatta cccagatcct atggttcgag gttttgctgt tcggtgcttg   1860

gaaaaatatt taacagatga caaactttct cagtatttaa ttcagctagt acaggtccta   1920

aaatatgaac aatatttgga taacttgctt gtgagatttt tactgaagaa agcattgact   1980

aatcaaagga ttgggcactt tttcttttgg catttaaaat ctgagatgca caataaaaca   2040

gttagccaga ggtttggcct gcttttggag tcctattgtc gtgcatgtgg gatgtatttg   2100

aagcacctga ataggcaagt cgaggcaatg gaaaagctca ttaacttaac tgacattctc   2160

aaacaggaga agaaggatga aacacaaaag gtacagatga agtttttagt tgagcaaatg   2220

aggcgaccag atttcatgga tgctctacag ggctttctgt ctcctctaaa ccctgctcat   2280

caactaggaa acctcaggct tgaagagtgt cgaattatgt cctctgcaaa aaggccactg   2340

tggttgaatt gggagaaccc agacatcatg tcagagttac tgtttcagaa caatgagatc   2400

atctttaaaa atggggatga tttacggcaa gatatgctaa cacttcaaat tattcgtatt   2460

atggaaaata tctggcaaaa tcaaggtctt gatcttcgaa tgttacctta tggttgtctg   2520

tcaatcggtg actgtgtggg acttattgag gtggtgcgaa attctcacac tattatgcaa   2580

attcagtgca aaggcggctt gaaaggtgca ctgcagttca acagccacac actacatcag   2640

tggctcaaag acaagaacaa aggagaaata tatgatgcag ccattgacct gtttacacgt   2700

tcatgtgctg gatactgtgt agctaccttc attttgggaa ttggagatcg tcacaatagt   2760

aacatcatgg tgaaagacga tggacagctg tttcatatag attttggaca ctttttggat   2820

cacaagaaga aaaaatttgg ttataaacga gaacgtgtgc catttgtttt gacacaggat   2880

ttcttaatag tgattagtaa aggagcccaa gaatgcacaa agacaagaga atttgagagg   2940

tttcaggaga tgtgttacaa ggcttatcta gctattcgac agcatgccaa tctcttcata   3000

aatcttttct caatgatgct tggctctgga atgccagaac tacaatcttt tgatgacatt   3060

gcatacattc gaaagaccct agccttagat aaaactgagc aagaggcttt ggagtatttc   3120

atgaaacaaa tgaatgatgc acatcatggt ggctggacaa caaaaatgga ttggatcttc   3180

cacacaatta aacagcatgc attgaactga                                    3210
```

<210> SEQ ID NO 51
<211> LENGTH: 2301
<212> TYPE: DNA
<213> ORGANISM: Homo sapiens

<400> SEQUENCE: 51

```
atggcggcgc tgagcggtgg cggtggtggc ggcgcggagc cgggccaggc tctgttcaac     60

ggggacatgg agcccgaggc cggcgccggc gccggcgccg cggcctcttc ggctgcggac    120

cctgccattc cggaggaggt gtggaatatc aaacaaatga ttaagttgac acaggaacat    180
```

```
atagaggccc tattggacaa atttggtggg gagcataatc caccatcaat atatctggag    240
gcctatgaag aatacaccag caagctagat gcactccaac aaagagaaca acagttattg    300
gaatctctgg ggaacggaac tgatttttct gtttctagct ctgcatcaat ggataccgtt    360
acatcttctt cctcttctag cctttcagtg ctaccttcat ctctttcagt tttcaaaat     420
cccacagatg tggcacggag caaccccaag tcaccacaaa aacctatcgt tagagtcttc    480
ctgcccaaca aacagaggac agtggtacct gcaaggtgtg gagttacagt ccgagacagt    540
ctaaagaaag cactgatgat gagaggtcta atcccagagt gctgtgctgt ttacagaatt    600
caggatggag agaagaaacc aattggttgg gacactgata tttcctggct tactggagaa    660
gaattgcatg tggaagtgtt ggagaatgtt ccacttacaa cacacaactt tgtacgaaaa    720
acgtttttca ccttagcatt ttgtgacttt tgtcgaaagc tgcttttcca gggtttccgc    780
tgtcaaacat gtggttataa atttcaccag cgttgtagta cagaagttcc actgatgtgt    840
gttaattatg accaacttga tttgctgttt gtctccaagt tctttgaaca ccacccaata    900
ccacaggaag aggcgtcctt agcagagact gccctaacat ctggatcatc cccttccgca    960
cccgcctcgg actctattgg gccccaaatt ctcaccagtc cgtctccttc aaaatccatt   1020
ccaattccac agcccttccg accagcagat gaagatcatc gaaatcaatt tgggcaacga   1080
gaccgatcct catcagctcc caatgtgcat ataaacacaa tagaacctgt caatattgat   1140
gacttgatta gagaccaagg atttcgtggt gatggaggat caaccacagg tttgtctgct   1200
acccccccctg cctcattacc tggctcacta actaacgtga aagccttaca gaaatctcca  1260
ggacctcagc gagaaaggaa gtcatcttca tcctcagaag acaggaatcg aatgaaaaca   1320
cttggtagac gggactcgag tgatgattgg gagattcctg atgggcagat tacagtggga   1380
caaagaattg gatctggatc atttggaaca gtctacaagg gaaagtggca tggtgatgtg   1440
gcagtgaaaa tgttgaatgt gacagcacct acacctcagc agttacaagc cttcaaaaat   1500
gaagtaggag tactcaggaa aacacgacat gtgaatatcc tactcttcat gggctattcc   1560
acaaagccac aactggctat tgttacccag tggtgtgagg gctccagctt gtatcaccat   1620
ctccatatca ttgagaccaa atttgagatg atcaaactta tagatattgc acgacagact   1680
gcacagggca tggattactt acacgccaag tcaatcatcc acagagacct caagagtaat   1740
aatatatttc ttcatgaaga cctcacagta aaaataggtg attttggtct agctacagag   1800
aaatctcgat ggagtgggtc ccatcagttt gaacagttgt ctggatccat tttgtggatg   1860
gcaccagaag tcatcagaat gcaagataaa aatccataca gctttcagtc agatgtatat   1920
gcatttggaa ttgttctgta tgaattgatg actggacagt taccttattc aaacatcaac   1980
aacagggacc agataatttt tatggtggga cgaggatacc tgtctccaga tctcagtaag   2040
gtacggagta actgtccaaa agccatgaag agattaatgg cagagtgcct caaaaagaaa   2100
agagatgaga gaccactctt tccccaaatt ctcgcctcta ttgagctgct ggcccgctca   2160
ttgccaaaaa ttcaccgcag tgcatcagaa ccctccttga atcgggctgg tttccaaaca   2220
gaggatttta gtctatatgc ttgtgcttct ccaaaaacac ccatccaggc agggggatat   2280
ggtgcgtttc ctgtccactg a                                             2301
```

```
<210> SEQ ID NO 52
<211> LENGTH: 186
<212> TYPE: DNA
<213> ORGANISM: Homo sapiens

<400> SEQUENCE: 52
```

gaagcctacg tgatggccag cgtggacaac ccccacgtgt gccgcctgct gggcatctgc 60
ctcacctcca ccgtgcaact catcacgcag ctcatgccct tcggctgcct cctggactat 120
gtccgggaac acaaagacaa tattggctcc cagtacctgc tcaactggtg tgtgcagatc 180
gcaaag 186

<210> SEQ ID NO 53
<211> LENGTH: 3207
<212> TYPE: DNA
<213> ORGANISM: Homo sapiens

<400> SEQUENCE: 53
atgcctccaa gaccatcatc aggtgaactg tggggcatcc acttgatgcc cccaagaatc 60
ctagtagaat gtttactacc aaatggaatg atagtgactt tagaatgcct ccgtgaggct 120
acattaataa ccataaagca tgaactattt aaagaagcaa gaaaataccc cctccatcaa 180
cttcttcaag atgaatcttc ttacattttc gtaagtgtta cccaagaagc agaaagggaa 240 gaatttttg atgaaacaag acgactttgt gaccttcggc tttttcaacc ctttttaaaa 300
gtaattgaac cagtaggcaa ccgtgaagaa aagatcctca atcgagaaat tggttttgct 360
atcggcatgc cagtgtgtga atttgatatg gttaaagatc cagaagtaca ggacttccga 420
agaaatattc tgaacgtttg taaagaagct gtggatctta gggacctcaa ttcacctcat 480
agtagagcaa tgtatgtcta tcctccaaat gtagaatctt caccagaatt gccaaagcac 540
atatataata aattagataa agggcaaata atagtggtga tctgggtaat agtttctcca 600
aataatgaca agcagaagta tactctgaaa atcaaccatg actgtgtacc agaacaagta 660
attgctgaag caatcaggaa aaaaactcga agtatgttgc tatcctctga acaactaaaa 720
ctctgtgttt tagaatatca gggcaagtat attttaaaag tgtgtggatg tgatgaatac 780
ttcctagaaa aatatcctct gagtcagtat aagtatataa gaagctgtat aatgcttggg 840
aggatgccca atttgatgtt gatggctaaa gaaagcctct attctcaact gccaatggac 900
tgttttacaa tgccatctta ttccagacgc atttccacag ctacaccata tatgaatgga 960
gaaacatcta caaaatccct ttgggttata aatagtgcac tcagaataaa aattctttgt 1020
gcaacctacg tgaatgtaaa tattcgagac attgataaga tctatgttcg aacaggtatc 1080
taccatggag gagaaccctt atgtgacaat gtgaacactc aaagagtacc ttgttccaat 1140
cccaggtgga atgaatggct gaattatgat atatacattc ctgatcttcc tcgtgctgct 1200
cgactttgcc tttccatttg ctctgttaaa ggccgaaagg gtgctaaaga ggaacactgt 1260
ccattggcat ggggaaatat aaacttgttt gattacacag acactctagt atctggaaaa 1320
atggctttga atctttggcc agtacctcat ggactagaag atttgctgaa ccctattggt 1380
gttactggat caaatccaaa taaagaaact ccatgcttag agttggagtt tgactggttc 1440
agcagtgtgg taaagttccc agatatgtca gtgattgaag agcatgccaa ttggtctgta 1500
tcccgagaag caggatttag ctattcccac gcaggactga gtaacagact agctagagac 1560
aatgaattaa gggaaaatga caaagaacag ctcaaagcaa tttctacacg agatcctctc 1620
tctaaaatca ctgagcagga gaaagatttt ctatggagtc acagacacta ttgtgtaact 1680
atccccgaaa ttctacccaa attgcttctg tctgttaaat ggaattctag agatgaagta 1740
gcccagatgt attgcttggt aaaagattgg cctccaatca aacctgaaca ggctatggaa 1800
cttctggact gtaattaccc agatcctatg gttcgaggtt ttgctgttcg gtgcttggaa 1860
aaatatttaa cagatgacaa actttctcag tatttaattc agctagtaca ggtcctaaaa 1920

```
tatgaacaat atttggataa cttgcttgtg agatttttac tgaagaaagc attgactaat   1980

caaaggattg ggcacttttt cttttggcat ttaaaatctg agatgcacaa taaaacagtt   2040

agccagaggt ttggcctgct tttggagtcc tattgtcgtg catgtgggat gtatttgaag   2100

cacctgaata ggcaagtcga ggcaatggaa aagctcatta acttaactga cattctcaaa   2160

caggagaaga aggatgaaac acaaaaggta cagatgaagt tttagttga gcaaatgagg    2220

cgaccagatt tcatggatgc tctacagggc tttctgtctc ctctaaaccc tgctcatcaa   2280

ctaggaaacc tcaggcttga agagtgtcga attatgtcct ctgcaaaaag gccactgtgg   2340

ttgaattggg agaacccaga catcatgtca gagttactgt ttcagaacaa tgagatcatc   2400

tttaaaaatg gggatgattt acggcaagat atgctaacac ttcaaattat tcgtattatg   2460

gaaaatatct ggcaaaatca aggtcttgat cttcgaatgt taccttatgg ttgtctgtca   2520

atcggtgact gtgtgggact tattgaggtg gtgcgaaatt ctcacactat tatgcaaatt   2580

cagtgcaaag gcggcttgaa aggtgcactg cagttcaaca gccacacact acatcagtgg   2640

ctcaaagaca agaacaaagg agaaatatat gatgcagcca ttgacctgtt tacacgttca   2700

tgtgctggat actgtgtagc taccttcatt ttgggaattg gagatcgtca caatagtaac   2760

atcatggtga aagacgatgg acagctgttt catatagatt ttggacactt tttggatcac   2820

aagaagaaaa aatttggtta taaacgagaa cgtgtgccat ttgttttgac acaggatttc   2880

ttaatagtga ttagtaaagg agcccaagaa tgcacaaaga caagagaatt tgagaggttt   2940

caggagatgt gttacaaggc ttatctagct attcgacagc atgccaatct cttcataaat   3000

cttttctcaa tgatgcttgg ctctggaatg ccagaactac aatcttttga tgacattgca   3060

tacattcgaa agaccctagc cttagataaa actgagcaag aggctttgga gtatttcatg   3120

aaacaaatga atgatgcaca tcatggtggc tggacaacaa aaatggattg gatcttccac   3180

acaattaaac agcatgcatt gaactga                                       3207
```

<210> SEQ ID NO 54
<211> LENGTH: 3207
<212> TYPE: DNA
<213> ORGANISM: Homo sapiens

<400> SEQUENCE: 54

```
atgcctccaa gaccatcatc aggtgaactg tggggcatcc acttgatgcc cccaagaatc     60

ctagtagaat gtttactacc aaatggaatg atagtgactt tagaatgcct ccgtgaggct    120

acattaataa ccataaagca tgaactattt aaagaagcaa gaaaataccc cctccatcaa    180

cttcttcaag atgaatcttc ttacatttc gtaagtgtta cccaagaagc agaaagggaa     240

gaattttttg atgaaacaag acgactttgt gaccttcggc tttttcaacc ctttttaaaa    300

gtaattgaac cagtaggcaa ccgtgaagaa aagatcctca atcgagaaat tggttttgct    360

atcggcatgc cagtgtgtga atttgatatg gttaaagatc cagaagtaca ggacttccga    420

agaaatattc tgaacgtttg taaagaagct gtggatctta gggacctcaa ttcacctcat    480

agtagagcaa tgtatgtcta tcctccaaat gtagaatctt caccagaatt gccaaagcac    540

atatataata aattagataa agggcaaata atagtggtga tctgggtaat agtttctcca    600

aataatgaca agcagaagta tactctgaaa atcaaccatg actgtgtacc agaacaagta    660

attgctgaag caatcaggaa aaaaactcga agtatgttgc tatcctctga acaactaaaa    720

ctctgtgttt tagaatatca gggcaagtat attttaaaag tgtgtggatg tgatgaatac    780

ttcctagaaa aatatcctct gagtcagtat aagtatataa gaagctgtat aatgcttggg    840
```

```
aggatgccca atttgatgtt gatggctaaa gaaagcctct attctcaact gccaatggac    900
tgttttacaa tgccatctta ttccagacgc atttccacag ctacaccata tatgaatgga    960
gaaacatcta caaaatccct ttgggttata aatagtgcac tcagaataaa aattctttgt   1020
gcaacctacg tgaatgtaaa tattcgagac attgataaga tctatgttcg aacaggtatc   1080
taccatggag gagaaccctt atgtgacaat gtgaacactc aaagagtacc ttgttccaat   1140
cccaggtgga atgaatggct gaattatgat atatacattc ctgatcttcc tcgtgctgct   1200
cgactttgcc tttccatttg ctctgttaaa ggccgaaagg gtgctaaaga ggaacactgt   1260
ccattggcat ggggaaatat aaacttgttt gattacacag acactctagt atctggaaaa   1320
atggctttga atctttggcc agtacctcat ggactagaag atttgctgaa ccctattggt   1380
gttactggat caaatccaaa taaagaaact ccatgcttag agttggagtt tgactggttc   1440
agcagtgtgg taaagttccc agatatgtca gtgattgaag agcatgccaa ttggtctgta   1500
tcccgagaag caggatttag ctattcccac gcaggactga gtaacagact agctagagac   1560
aatgaattaa gggaaaatga caaagaacag ctcaaagcaa tttctacacg agatcctctc   1620
tctgaaatca ctgagcagga gaaagatttt ctatggagtc acagacacta ttgtgtaact   1680
atccccgaaa ttctacccaa attgcttctg tctgttaaat ggaattctag agatgaagta   1740
gcccagatgt attgcttggt aaaagattgg cctccaatca aacctgaaca ggctatggaa   1800
cttctggact gtaattaccc agatcctatg gttcgaggtt ttgctgttcg gtgcttggaa   1860
aaatatttaa cagatgacaa actttctcag tatttaattc agctagtaca ggtcctaaaa   1920
tatgaacaat atttggataa cttgcttgtg agatttttac tgaagaaagc attgactaat   1980
caaaggattg ggcacttttt cttttggcat ttaaaatctg agatgcacaa taaaacagtt   2040
agccagaggt ttggcctgct tttggagtcc tattgtcgtg catgtgggat gtatttgaag   2100
cacctgaata ggcaagtcga ggcaatggaa aagctcatta acttaactga cattctcaaa   2160
caggagaaga aggatgaaac acaaaaggta cagatgaagt ttttagttga gcaaatgagg   2220
cgaccagatt tcatggatgc tctacagggc tttctgtctc ctctaaaccc tgctcatcaa   2280
ctaggaaacc tcaggcttga agagtgtcga attatgtcct ctgcaaaaag gccactgtgg   2340
ttgaattggg agaacccaga catcatgtca gagttactgt ttcagaacaa tgagatcatc   2400
tttaaaaatg gggatgattt acggcaagat atgctaacac ttcaaattat tcgtattatg   2460
gaaaatatct ggcaaaatca aggtcttgat cttcgaatgt taccttatgg ttgtctgtca   2520
atcggtgact gtgtgggact tattgaggtg gtgcgaaatt ctcacactat tatgcaaatt   2580
cagtgcaaag gcggcttgaa aggtgcactg cagttcaaca gccacacact acatcagtgg   2640
ctcaaagaca agaacaaagg agaaatatat gatgcagcca ttgacctgtt tacacgttca   2700
tgtgctggat actgtgtagc taccttcatt ttgggaattg gagatcgtca caatagtaac   2760
atcatggtga aagacgatgg acagctgttt catatagatt ttggacactt tttggatcac   2820
aagaagaaaa aatttggtta taaacgagaa cgtgtgccat ttgttttgac acaggatttc   2880
ttaatagtga ttagtaaagg agcccaagaa tgcacaaaga caagagaatt tgagaggttt   2940
caggagatgt gttacaaggc ttatctagct attcgacagc atgccaatct cttcataaat   3000
cttttctcaa tgatgcttgg ctctggaatg ccagaactac aatcttttga tgacattgca   3060
tacattcgaa agaccctagc cttagataaa actgagcaag aggctttgga gtatttcatg   3120
aaacaaatga atgatgcact tcatggtggc tggacaacaa aaatggattg gatcttccac   3180
acaattaaac agcatgcatt gaactga                                        3207
```

<210> SEQ ID NO 55
<211> LENGTH: 3633
<212> TYPE: DNA
<213> ORGANISM: Homo sapiens

<400> SEQUENCE: 55

```
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
```

```
ggtgcgttcg gcacggtgta taagggactc tggatcccag aaggtgagaa agttaaaatt   2220

cccgtcgcta tcaaggaatt aagagaagca acatctccga aagccaacaa ggaaatcctc   2280

gatgaagcct acgtgatggc cagcgtggac aacccccacg tgtgccgcct gctgggcatc   2340

tgcctcacct ccaccgtgca actcatcacg cagctcatgc ccttcggctg cctcctggac   2400

tatgtccggg aacacaaaga caatattggc tcccagtacc tgctcaactg gtgtgtgcag   2460

atcgcaaagg gcatgaacta cttggaggac cgtcgcttgg tgcaccgcga cctggcagcc   2520

aggaacgtac tggtgaaaac accgcagcat gtcaagatca cagattttgg gctggccaaa   2580

ctgctgggtg cggaagagaa agaataccat gcagaaggag gcaaagtgcc tatcaagtgg   2640

atggcattgg aatcaatttt acacagaatc tatacccacc agagtgatgt ctggagctac   2700

ggggtgaccg tttgggagtt gatgaccttt ggatccaagc catatgacgg aatccctgcc   2760

agcgagatct cctccatcct ggagaaagga gaacgcctcc ctcagccacc catatgtacc   2820

atcgatgtct acatgatcat ggtcaagtgc tggatgatag acgcagatag tcgcccaaag   2880

ttccgtgagt tgatcatcga attctccaaa atggcccgag acccccagcg ctaccttgtc   2940

attcaggggg atgaaagaat gcatttgcca agtcctacag actccaactt ctaccgtgcc   3000

ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 56
<211> LENGTH: 2484
<212> TYPE: DNA
<213> ORGANISM: Homo sapiens

<400> SEQUENCE: 56

```
atgcgaccct ccgggacggc cggggcagcg ctcctggcgc tgctggctgc gctctgcccg     60

gcgagtcggg ctctggagga aaagaaagtt tgccaaggca cgagtaacaa gctcacgcag    120

ttgggcactt ttgaagatca ttttctcagc ctccagagga tgttcaataa ctgtgaggtg    180

gtccttggga atttggaaat tacctatgtg cagaggaatt atgatctttc cttcttaaag    240

accatccagg aggtggctgg ttatgtcctc attgccctca acacagtgga gcgaattcct    300

ttggaaaacc tgcagatcat cagaggaaat atgtactacg aaaattccta tgccttagca    360

gtcttatcta actatgatgc aaataaaacc ggactgaagg agctgcccat gagaaattta    420

caggaaatcc tgcatggcgc cgtgcggttc agcaacaacc ctgccctgtg caacgtggag    480

agcatccagt ggcgggacat agtcagcagt gactttctca gcaacatgtc gatggacttc    540

cagaaccacc tgggcagctg ccaaaagtgt gatccaagct gtcccaatgg gagctgctgg    600

ggtgcaggag aggagaactg ccagaaactg accaaaatca tctgtgccca gcagtgctcc    660
```

gggcgctgcc gtggcaagtc ccccagtgac tgctgccaca accagtgtgc tgcaggctgc 720
acaggccccc gggagagcga ctgcctggtc tgccgcaaat tccgagacga agccacgtgc 780
aaggacacct gccccccact catgctctac aaccccacca cgtaccagat ggatgtgaac 840
cccgagggca aatacagctt tggtgccacc tgcgtgaaga agtgtccccg taattatgtg 900
gtgacagatc acggctcgtg cgtccgagcc tgtggggccg acagctatga gatggaggaa 960
gacggcgtcc gcaagtgtaa gaagtgcgaa gggccttgcc gcaaagtgtg taacggaata 1020
ggtattggtg aatttaaaga ctcactctcc ataaatgcta cgaatattaa acacttcaaa 1080
aactgcacct ccatcagtgg cgatctccac atcctgccgg tggcatttag ggtgactcc 1140 ttcacacata ctcctcctct ggatccacag gaactggata ttctgaaaac cgtaaaggaa 1200
atcacagggt ttttgctgat tcaggcttgg cctgaaaaca ggacggacct ccatgccttt 1260
gagaacctag aaatcatacg cggcaggacc aagcaacatg gtcagttttc tcttgcagtc 1320
gtcagcctga acataacatc cttgggatta cgctccctca aggagataag tgatggagat 1380
gtgataattt caggaaacaa aaatttgtgc tatgcaaata caataaactg gaaaaaactg 1440
tttgggacct ccggtcagaa aaccaaaatt ataagcaaca gaggtgaaaa cagctgcaag 1500
gccacaggcc aggtctgcca tgccttgtgc tcccccgagg gctgctgggg cccggagccc 1560
agggactgcg tctcttgccg gaatgtcagc cgaggcaggg aatgcgtgga caagtgcaag 1620
cttctggagg gtgagccaag ggagtttgtg gagaactctg agtgcataca gtgccaccca 1680
gagtgcctgc ctcaggccat gaacatcacc tgcacaggac ggggaccaga caactgtatc 1740
cagtgtgccc actacattga cggcccccac tgcgtcaaga cctgcccggc aggagtcatg 1800
ggagaaaaca acaccctggt ctggaagtac gcagacgccg gccatgtgtg ccacctgtgc 1860
catccaaact gcacctacgg atgcactggg ccaggtcttg aaggctgtcc aacgaatggg 1920
cctaagatcc cgtccatcgc cactgggatg gtgggggccc tcctcttgct gctggtggtg 1980
gccctgggga tcggcctctt catgcgaagg cgccacatcg ttcggaagcg cacgctgcgg 2040
aggctgctgc aggagaggga gcttgtggag cctcttacac ccagtggaga agctcccaac 2100
caagctctct tgaggatctt gaaggaaact gaattcaaaa agatcaaagt gctgggctcc 2160
ggtgcgttcg gcacggtgta taagggactc tggatcccag aaggtgagaa agttaaaatt 2220
cccgtcgcta tcaaggaatt aagagaagca acatctccga aagccaacaa ggaaatcctc 2280
gatgaagcct acgtgatggc cagcgtggac aacccccacg tgtgccgcct gctgggcatc 2340
tgcctcacct ccaccgtgca actcatcacg cagctcatgc ccttcggctg cctcctggac 2400
tatgtccggg aacacaaaga caatattggc tcccagtacc tgctcaactg gtgtgtgcag 2460
atcgcaaagg gcatgaacta ctag 2484

<210> SEQ ID NO 57
<211> LENGTH: 2301
<212> TYPE: DNA
<213> ORGANISM: Homo sapiens

<400> SEQUENCE: 57
atggcggcgc tgagcggtgg cggtggtggc ggcgcggagc cgggccaggc tctgttcaac 60
ggggacatgg agcccgaggc cggcgccggc gccggcgccg cggcctcttc ggctgcggac 120
cctgccattc cggaggaggt gtggaatatc aaacaaatga ttaagttgac acaggaacat 180
atagaggccc tattggacaa atttggtggg gagcataatc caccatcaat atatctggag 240
gcctatgaag aatacaccag caagctagat gcactccaac aaagagaaca acagttattg 300

```
gaatctctgg ggaacggaac tgatttttct gtttctagct ctgcatcaat ggataccgtt    360

acatcttctt cctcttctag cctttcagtg ctaccttcat ctctttcagt tttcaaaat    420

cccacagatg tggcacggag caaccccaag tcaccacaaa aacctatcgt tagagtcttc    480

ctgcccaaca aacagaggac agtggtacct gcaaggtgtg gagttacagt ccgagacagt    540

ctaaagaaag cactgatgat gagaggtcta atcccagagt gctgtgctgt ttacagaatt    600

caggatggag agaagaaacc aattggttgg gacactgata tttcctggct tactggagaa    660

gaattgcatg tggaagtgtt ggagaatgtt ccacttacaa cacacaactt tgtacgaaaa    720

acgtttttca ccttagcatt ttgtgacttt tgtcgaaagc tgcttttcca gggtttccgc    780

tgtcaaacat gtggttataa atttcaccag cgttgtagta cagaagttcc actgatgtgt    840

gttaattatg accaacttga tttgctgttt gtctccaagt tctttgaaca ccacccaata    900

ccacaggaag aggcgtcctt agcagagact gccctaacat ctggatcatc cccttccgca    960

cccgcctcgg actctattgg gccccaaatt ctcaccagtc cgtctccttc aaaatccatt   1020

ccaattccac agcccttccg accagcagat gaagatcatc gaaatcaatt tgggcaacga   1080

gaccgatcct catcagctcc caatgtgcat ataaacacaa tagaacctgt caatattgat   1140

gacttgatta gagaccaagg atttcgtggt gatggaggat caaccacagg tttgtctgct   1200

acccccccctg cctcattacc tggctcacta actaacgtga aagccttaca gaaatctcca   1260

ggacctcagc gagaaaggaa gtcatcttca tcctcagaag acaggaatcg aatgaaaaca   1320

cttggtagac gggactcgag tgatgattgg gagattcctg atgggcagat tacagtggga   1380

caaagaattg gatctggatc atttggaaca gtctacaagg gaaagtggca tggtgatgtg   1440

gcagtgaaaa tgttgaatgt gacagcacct acacctcagc agttacaagc cttcaaaaat   1500

gaagtaggag tactcaggaa aacacgacat gtgaatatcc tactcttcat gggctattcc   1560

acaaagccac aactggctat tgttacccag tggtgtgagg gctccagctt gtatcaccat   1620

ctccatatca ttgagaccaa atttgagatg atcaaactta tagatattgc acgacagact   1680

gcacagggca tggattactt acacgccaag tcaatcatcc acagagacct caagagtaat   1740

aatatatttc ttcatgaaga cctcacagta aaaataggtg attttggtct agctacagtg   1800

gaatctcgat ggagtgggtc ccatcagttt gaacagttgt ctggatccat tttgtggatg   1860

gcaccagaag tcatcagaat gcaagataaa aatccataca gctttcagtc agatgtatat   1920

gcatttggaa ttgttctgta tgaattgatg actggacagt taccttattc aaacatcaac   1980

aacagggacc agataatttt tatggtggga cgaggatacc tgtctccaga tctcagtaag   2040

gtacggagta actgtccaaa agccatgaag agattaatgg cagagtgcct caaaaagaaa   2100

agagatgaga gaccactctt tccccaaatt ctcgcctcta ttgagctgct ggcccgctca   2160

ttgccaaaaa ttcaccgcag tgcatcagaa ccctccttga atcgggctgg tttccaaaca   2220

gaggatttta gtctatatgc ttgtgcttct ccaaaaacac ccatccaggc agggggatat   2280

ggtgcgtttc ctgtccactg a                                             2301
```

<210> SEQ ID NO 58
<211> LENGTH: 3207
<212> TYPE: DNA
<213> ORGANISM: Homo sapiens

<400> SEQUENCE: 58

```
atgcctccaa gaccatcatc aggtgaactg tggggcatcc acttgatgcc cccaagaatc     60

ctagtagaat gtttactacc aaatggaatg atagtgactt tagaatgcct ccgtgaggct    120
```

```
acattaataa ccataaagca tgaactattt aaagaagcaa gaaaataccc cctccatcaa    180
cttcttcaag atgaatcttc ttacattttc gtaagtgtta cccaagaagc agaaagggaa    240
gaatttttg atgaaacaag acgactttgt gaccttcggc tttttcaacc ctttttaaaa    300
gtaattgaac cagtaggcaa ccgtgaagaa aagatcctca atcgagaaat tggttttgct    360
atcggcatgc cagtgtgtga atttgatatg gttaaagatc cagaagtaca ggacttccga    420
agaaatattc tgaacgtttg taaagaagct gtggatctta gggacctcaa ttcacctcat    480
agtagagcaa tgtatgtcta tcctccaaat gtagaatctt caccagaatt gccaaagcac    540
atatataata aattagataa agggcaaata atagtggtga tctgggtaat agtttctcca    600
aataatgaca agcagaagta tactctgaaa atcaaccatg actgtgtacc agaacaagta    660
attgctgaag caatcaggaa aaaaactcga agtatgttgc tatcctctga acaactaaaa    720
ctctgtgttt tagaatatca gggcaagtat attttaaaag tgtgtggatg tgatgaatac    780
ttcctagaaa aatatcctct gagtcagtat aagtatataa gaagctgtat aatgcttggg    840
aggatgccca atttgatgtt gatggctaaa gaaagcctct attctcaact gccaatggac    900
tgttttacaa tgccatctta ttccagacgc atttccacag ctacaccata tatgaatgga    960
gaaacatcta caaaatccct ttgggttata aatagtgcac tcagaataaa aattctttgt   1020
gcaacctacg tgaatgtaaa tattcgagac attgataaga tctatgttcg aacaggtatc   1080
taccatggag gagaaccctt atgtgacaat gtgaacactc aaagagtacc ttgttccaat   1140
cccaggtgga atgaatggct gaattatgat atatacattc ctgatcttcc tcgtgctgct   1200
cgactttgcc tttccatttg ctctgttaaa ggccgaaagg gtgctaaaga ggaacactgt   1260
ccattggcat ggggaaatat aaacttgttt gattacacag acactctagt atctggaaaa   1320
atggctttga atctttggcc agtacctcat ggactagaag atttgctgaa ccctattggt   1380
gttactggat caaatccaaa taaagaaact ccatgcttag agttggagtt tgactggttc   1440
agcagtgtgg taaagttccc agatatgtca gtgattgaag agcatgccaa ttggtctgta   1500
tcccgagaag caggatttag ctattcccac gcaggactga gtaacagact agctagagac   1560
aatgaattaa gggaaaatga caaagaacag ctcaaagcaa tttctacacg agatcctctc   1620
tctgaaatca ctgagcagga gaaagatttt ctatggagtc acagacacta ttgtgtaact   1680
atccccgaaa ttctacccaa attgcttctg tctgttaaat ggaattctag agatgaagta   1740
gcccagatgt attgcttggt aaaagattgg cctccaatca aacctgaaca ggctatggaa   1800
cttctggact gtaattaccc agatcctatg gttcgaggtt ttgctgttcg gtgcttggaa   1860
aaatatttaa cagatgacaa actttctcag tatttaattc agctagtaca ggtcctaaaa   1920
tatgaacaat atttggataa cttgcttgtg agatttttac tgaagaaagc attgactaat   1980
caaaggattg ggcacttttt cttttggcat ttaaaatctg agatgcacaa taaaacagtt   2040
agccagaggt ttggcctgct tttggagtcc tattgtcgtg catgtgggat gtatttgaag   2100
cacctgaata ggcaagtcga ggcaatggaa aagctcatta acttaactga cattctcaaa   2160
caggagaaga aggatgaaac acaaaaggta cagatgaagt tttagttga gcaaatgagg   2220
cgaccagatt tcatggatgc tctacagggc tttctgtctc ctctaaaccc tgctcatcaa   2280
ctaggaaacc tcaggcttga agagtgtcga attatgtcct ctgcaaaaag gccactgtgg   2340
ttgaattggg agaacccaga catcatgtca gagttactgt ttcagaacaa tgagatcatc   2400
tttaaaaatg gggatgattt acggcaagat atgctaacac ttcaaattat tcgtattatg   2460
gaaaatatct ggcaaaatca aggtcttgat cttcgaatgt taccttatgg ttgtctgtca   2520
```

```
atcggtgact gtgtgggact tattgaggtg gtgcgaaatt ctcacactat tatgcaaatt   2580

cagtgcaaag gcggcttgaa aggtgcactg cagttcaaca gccacacact acatcagtgg   2640

ctcaaagaca agaacaaagg agaaatatat gatgcagcca ttgacctgtt tacacgttca   2700

tgtgctggat actgtgtagc taccttcatt ttgggaattg gagatcgtca caatagtaac   2760

atcatggtga aagacgatgg acagctgttt catatagatt ttggacactt tttggatcac   2820

aagaagaaaa aatttggtta taaacgagaa cgtgtgccat ttgttttgac acaggatttc   2880

ttaatagtga ttagtaaagg agcccaagaa tgcacaaaga caagagaatt tgagaggttt   2940

caggagatgt gttacaaggc ttatctagct attcgacagc atgccaatct cttcataaat   3000

cttttctcaa tgatgcttgg ctctggaatg ccagaactac aatcttttga tgacattgca   3060

tacattcgaa agaccctagc cttagataaa actgagcaag aggctttgga gtatttcatg   3120

aaacaaatga atgatgcaca tcatggtggc tggacaacaa aaatggattg gatcttccac   3180

acaattaaac agcatgcatt gaactga                                       3207
```

<210> SEQ ID NO 59
<211> LENGTH: 189
<212> TYPE: DNA
<213> ORGANISM: Homo sapiens

<400> SEQUENCE: 59

```
gaagcctacg tgatggccag cgtggacaac cacccccacg tgtgccgcct gctgggcatc     60

tgcctcacct ccaccgtgca actcatcacg cagctcatgc ccttcggctg cctcctggac    120

tatgtccggg aacacaaaga caatattggc tcccagtacc tgctcaactg gtgtgtgcag    180

atcgcaaag                                                            189
```

<210> SEQ ID NO 60
<211> LENGTH: 2301
<212> TYPE: DNA
<213> ORGANISM: Homo sapiens

<400> SEQUENCE: 60

```
atggcggcgc tgagcggtgg cggtggtggc ggcgcggagc cgggccaggc tctgttcaac     60

ggggacatgg agcccgaggc cggcgccggc gccggcgccg cggcctcttc ggctgcggac    120

cctgccattc cggaggaggt gtggaatatc aaacaaatga ttaagttgac acaggaacat    180

atagaggccc tattggacaa atttggtggg gagcataatc caccatcaat atatctggag    240

gcctatgaag aatacaccag caagctagat gcactccaac aaagagaaca acagttattg    300

gaatctctgg ggaacggaac tgatttttct gtttctagct ctgcatcaat ggataccgtt    360

acatcttctt cctcttctag cctttcagtg ctaccttcat ctctttcagt ttttcaaaat    420

cccacagatg tggcacggag caaccccaag tcaccacaaa aacctatcgt tagagtcttc    480

ctgcccaaca aacagaggac agtggtacct gcaaggtgtg gagttacagt ccgagacagt    540

ctaaagaaag cactgatgat gagaggtcta atcccagagt gctgtgctgt ttacagaatt    600

caggatggag agaagaaacc aattggttgg gacactgata tttcctggct tactggagaa    660

gaattgcatg tggaagtgtt ggagaatgtt ccacttacaa cacacaactt tgtacgaaaa    720

acgtttttca ccttagcatt ttgtgacttt tgtcgaaagc tgcttttcca gggtttccgc    780

tgtcaaacat gtggttataa atttcaccag cgttgtagta cagaagttcc actgatgtgt    840

gttaattatg accaacttga tttgctgttt gtctccaagt tctttgaaca ccacccaata    900

ccacaggaag aggcgtcctt agcagagact gccctaacat ctggatcatc cccttccgca    960
```

```
cccgcctcgg actctattgg gccccaaatt ctcaccagtc cgtctccttc aaaatccatt   1020
ccaattccac agcccttccg accagcagat gaagatcatc gaaatcaatt tgggcaacga   1080
gaccgatcct catcagctcc caatgtgcat ataaacacaa tagaacctgt caatattgat   1140
gacttgatta gagaccaagg atttcgtggt gatggaggat caaccacagg tttgtctgct   1200
acccccccctg cctcattacc tggctcacta actaacgtga aagccttaca gaaatctcca   1260
ggacctcagc gagaaaggaa gtcatcttca tcctcagaag acaggaatcg aatgaaaaca   1320
cttggtagac gggactcgag tgatgattgg gagattcctg atgggcagat tacagtggga   1380
caaagaattg gatctggatc atttggaaca gtctacaagg gaaagtggca tggtgatgtg   1440
gcagtgaaaa tgttgaatgt gacagcacct acacctcagc agttacaagc cttcaaaaat   1500
gaagtaggag tactcaggaa aacacgacat gtgaatatcc tactcttcat gggctattcc   1560
acaaagccac aactggctat tgttacccag tggtgtgagg gctccagctt gtatcaccat   1620
ctccatatca ttgagaccaa atttgagatg atcaaactta tagatattgc acgacagact   1680
gcacagggca tggattactt acacgccaag tcaatcatcc acagagacct caagagtaat   1740
aatatatttc ttcatgaaga cctcacagta aaaataggtg attttggtct agctacagtg   1800
aaatctcgat ggagtgggtc ccatcagttt gaacagttgt ctggatccat tttgtggatg   1860
gcaccagaag tcatcagaat gcaagataaa aatccataca gctttcagtc agatgtatat   1920
gcatttggaa ttgttctgta tgaattgatg actggacagt taccttattc aaacatcaac   1980
aacagggacc agataatttt tatggtggga cgaggatacc tgtctccaga tctcagtaag   2040
gtacggagta actgtccaaa agccatgaag agattaatgg cagagtgcct caaaaagaaa   2100
agagatgaga gaccactctt tccccaaatt ctcgcctcta ttgagctgct ggcccgctca   2160
ttgccaaaaa ttcaccgcag tgcatcagaa ccctccttga atcgggctgg tttccaaaca   2220
gaggatttta gtctatatgc ttgtgcttct ccaaaaacac ccatccaggc agggggatat   2280
ggtgcgtttc ctgtccactg a                                             2301
```

<210> SEQ ID NO 61
<211> LENGTH: 3633
<212> TYPE: DNA
<213> ORGANISM: Homo sapiens

<400> SEQUENCE: 61

```
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
```

```
aaggacacct gccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggggtgactcc  1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gcgggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
accagcaaca attccaccgt ggcttgcatt gatagaaatg ggctgcaaag ctgtcccatc   3180
```

```
aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                 3633
```

```
<210> SEQ ID NO 62
<211> LENGTH: 62
<212> TYPE: PRT
<213> ORGANISM: Homo sapiens

<400> SEQUENCE: 62

Glu Ala Tyr Val Met Ala Ser Val Asp Asn Pro His Val Cys Arg Leu
1               5                   10                  15

Leu Gly Ile Cys Leu Thr Ser Thr Val Gln Leu Ile Thr Gln Leu Met
            20                  25                  30

Pro Phe Gly Cys Leu Leu Asp Tyr Val Arg Glu His Lys Asp Asn Ile
        35                  40                  45

Gly Ser Gln Tyr Leu Leu Asn Trp Cys Val Gln Ile Ala Lys
    50                  55                  60
```

```
<210> SEQ ID NO 63
<211> LENGTH: 186
<212> TYPE: DNA
<213> ORGANISM: Homo sapiens

<400> SEQUENCE: 63

gaagcctacg tgatggccag cgtggacaac ccccacgtgt gccgcctgct gggcatctgc     60

ctcacctcca ccgtgcaact catcacgcag ctcatgccct tcggctgcct cctggactat    120

gtccgggaac acaaagacaa tattggctcc cagtacctgc tcaactggtg tgtgcagatc    180

gcaaag                                                               186
```

```
<210> SEQ ID NO 64
<211> LENGTH: 186
<212> TYPE: DNA
<213> ORGANISM: Homo sapiens

<400> SEQUENCE: 64

gaagcctacg tgatggccag cgtggacaac ccccacgtgt gccgcctgct gggcatctgc     60

ctcacctcca ccgtgcaact catcatgcag ctcatgccct tcggctgcct cctggactat    120

gtccgggaac acaaagacaa tattggctcc cagtacctgc tcaactggtg tgtgcagatc    180

gcaaag                                                               186
```

```
<210> SEQ ID NO 65
<211> LENGTH: 62
<212> TYPE: PRT
<213> ORGANISM: Homo sapiens

<400> SEQUENCE: 65

Glu Ala Tyr Val Met Ala Ser Val Asp Asn Pro His Val Cys Arg Leu
1               5                   10                  15
```

```
Leu Gly Ile Cys Leu Thr Ser Thr Val Gln Leu Ile Thr Gln Leu Met
            20                  25                  30

Pro Phe Gly Cys Leu Leu Asp Tyr Val Arg Glu His Lys Asp Asn Ile
        35                  40                  45

Gly Ser Gln Tyr Leu Leu Asn Trp Cys Val Gln Ile Ala Lys
    50                  55                  60


<210> SEQ ID NO 66
<211> LENGTH: 62
<212> TYPE: PRT
<213> ORGANISM: Homo sapiens

<400> SEQUENCE: 66

Glu Ala Tyr Val Met Ala Ser Val Asp Asn Pro His Val Cys Arg Leu
1               5                   10                  15

Leu Gly Ile Cys Leu Thr Ser Thr Val Gln Leu Ile Met Gln Leu Met
            20                  25                  30

Pro Phe Gly Cys Leu Leu Asp Tyr Val Arg Glu His Lys Asp Asn Ile
        35                  40                  45

Gly Ser Gln Tyr Leu Leu Asn Trp Cys Val Gln Ile Ala Lys
    50                  55                  60


<210> SEQ ID NO 67
<211> LENGTH: 123
<212> TYPE: DNA
<213> ORGANISM: Homo sapiens

<400> SEQUENCE: 67

cttgtggagc ctcttacacc cagtggagaa gctcccaacc aagctctctt gaggatcttg      60

aaggaaactg aattcaaaaa gatcaaagtg ctgggctccg gtgcgttcgg cacggtgtat     120

aag                                                                   123


<210> SEQ ID NO 68
<211> LENGTH: 123
<212> TYPE: DNA
<213> ORGANISM: Homo sapiens

<400> SEQUENCE: 68

cttgtggagc ctcttacacc cagtggagaa gctcccaacc acgctctctt gaggatcttg      60

aaggaaactg aattcaaaaa gatcaaagtg ctgggctccg gtgcgttcgg cacggtgtat     120

aag                                                                   123


<210> SEQ ID NO 69
<211> LENGTH: 41
<212> TYPE: PRT
<213> ORGANISM: Homo sapiens

<400> SEQUENCE: 69

Leu Val Glu Pro Leu Thr Pro Ser Gly Glu Ala Pro Asn Gln Ala Leu
1               5                   10                  15

Leu Arg Ile Leu Lys Glu Thr Glu Phe Lys Lys Ile Lys Val Leu Gly
            20                  25                  30

Ser Gly Ala Phe Gly Thr Val Tyr Lys
        35                  40


<210> SEQ ID NO 70
<211> LENGTH: 41
<212> TYPE: PRT
<213> ORGANISM: Homo sapiens
```

<400> SEQUENCE: 70

```
Leu Val Glu Pro Leu Thr Pro Ser Gly Glu Ala Pro Asn His Ala Leu
1               5                   10                  15

Leu Arg Ile Leu Lys Glu Thr Glu Phe Lys Lys Ile Lys Val Leu Gly
            20                  25                  30

Ser Gly Ala Phe Gly Thr Val Tyr Lys
        35                  40
```

<210> SEQ ID NO 71
<211> LENGTH: 123
<212> TYPE: DNA
<213> ORGANISM: Homo sapiens

<400> SEQUENCE: 71

```
cttgtggagc ctcttacacc cagtggagaa gctcccaacc aagctctctt gaggatcttg     60

aaggaaactg aattcaaaaa gatcaaagtg ctgggctccg gtgcgttcgg cacggtgtat    120

aag                                                                  123
```

<210> SEQ ID NO 72
<211> LENGTH: 123
<212> TYPE: DNA
<213> ORGANISM: Homo sapiens

<400> SEQUENCE: 72

```
cctgtggagc ctcttacacc cagtggagaa gctcccaacc aagctctctt gaggatcttg     60

aaggaaactg aattcaaaaa gatcaaagtg ctgggctccg gtgcgttcgg cacggtgtat    120

aag                                                                  123
```

<210> SEQ ID NO 73
<211> LENGTH: 41
<212> TYPE: PRT
<213> ORGANISM: Homo sapiens

<400> SEQUENCE: 73

```
Leu Val Glu Pro Leu Thr Pro Ser Gly Glu Ala Pro Asn Gln Ala Leu
1               5                   10                  15

Leu Arg Ile Leu Lys Glu Thr Glu Phe Lys Lys Ile Lys Val Leu Gly
            20                  25                  30

Ser Gly Ala Phe Gly Thr Val Tyr Lys
        35                  40
```

<210> SEQ ID NO 74
<211> LENGTH: 41
<212> TYPE: PRT
<213> ORGANISM: Homo sapiens

<400> SEQUENCE: 74

```
Pro Val Glu Pro Leu Thr Pro Ser Gly Glu Ala Pro Asn Gln Ala Leu
1               5                   10                  15

Leu Arg Ile Leu Lys Glu Thr Glu Phe Lys Lys Ile Lys Val Leu Gly
            20                  25                  30

Ser Gly Ala Phe Gly Thr Val Tyr Lys
        35                  40
```

<210> SEQ ID NO 75
<211> LENGTH: 124
<212> TYPE: DNA
<213> ORGANISM: Homo sapiens

<400> SEQUENCE: 75

```
gtaacagact agctagagac aatgaattaa gggaaaatga caaagaacag ctcaaagcaa     60

tttctacacg agatcctctc tctgaaatca ctgagcagga gaaagatttt ctatggagtc    120

acag                                                                 124


<210> SEQ ID NO 76
<211> LENGTH: 127
<212> TYPE: DNA
<213> ORGANISM: Homo sapiens

<400> SEQUENCE: 76

gtaacagact agctagagac aatgaattaa gggaaaatga caaagaacag ctcaaagcaa     60

tttctacacg agatcctctc tctgaaatca ctgcgcagga gaaagatttt ctatggacca    120

caggtaa                                                              127


<210> SEQ ID NO 77
<211> LENGTH: 40
<212> TYPE: PRT
<213> ORGANISM: Homo sapiens

<400> SEQUENCE: 77

Asn Arg Leu Ala Arg Asp Asn Glu Leu Arg Glu Asn Asp Lys Glu Gln
1               5                   10                  15

Leu Lys Ala Ile Ser Thr Arg Asp Pro Leu Ser Glu Ile Thr Glu Gln
            20                  25                  30

Glu Lys Asp Phe Leu Trp Ser His
        35                  40


<210> SEQ ID NO 78
<211> LENGTH: 41
<212> TYPE: PRT
<213> ORGANISM: Homo sapiens

<400> SEQUENCE: 78

Asn Arg Leu Ala Arg Asp Asn Glu Leu Arg Glu Asn Asp Lys Glu Gln
1               5                   10                  15

Leu Lys Ala Ile Ser Thr Arg Asp Pro Leu Ser Glu Ile Thr Ala Gln
            20                  25                  30

Glu Lys Asp Phe Leu Trp Thr Thr Gly
        35                  40


<210> SEQ ID NO 79
<211> LENGTH: 271
<212> TYPE: DNA
<213> ORGANISM: Homo sapiens

<400> SEQUENCE: 79

gtttcaggag atgtgttaca aggcttatct agctattcga cagcatgcca atctcttcat     60

aaatcttttc tcaatgatgc ttggctctgg aatgccagaa ctacaatctt ttgatgacat    120

tgcatacatt cgaaagaccc tagccttaga taaaactgag caagaggctt tggagtattt    180

catgaaacaa atgaatgatg cacatcatgg tggctggaca acaaaaatgg attggatctt    240

ccacacaatt aaacagcatg cattgaactg a                                   271


<210> SEQ ID NO 80
<211> LENGTH: 271
<212> TYPE: DNA
<213> ORGANISM: Homo sapiens

<400> SEQUENCE: 80
```

```
gtttcaggag atgtgttaca aggcttatct agctattcga cagcatgcca atctcttcat     60

aaatcttttc tcaatgatgc ttggctctgg aatgccagaa ctacaatctt ttgatgacat    120

tgcatacatt cgaaagaccc tagccttaga taaaactgag caagaggctt tggagtattt    180

catgaaacaa atgaatgatg cacttcatgg tggctggaca acaaaaatgg attggatctt    240

ccacacaatt aaacagcatg cattgaactg a                                   271


<210> SEQ ID NO 81
<211> LENGTH: 89
<212> TYPE: PRT
<213> ORGANISM: Homo sapiens

<400> SEQUENCE: 81

Phe Gln Glu Met Cys Tyr Lys Ala Tyr Leu Ala Ile Arg Gln His Ala
1               5                   10                  15

Asn Leu Phe Ile Asn Leu Phe Ser Met Met Leu Gly Ser Gly Met Pro
            20                  25                  30

Glu Leu Gln Ser Phe Asp Asp Ile Ala Tyr Ile Arg Lys Thr Leu Ala
        35                  40                  45

Leu Asp Lys Thr Glu Gln Glu Ala Leu Glu Tyr Phe Met Lys Gln Met
    50                  55                  60

Asn Asp Ala His His Gly Gly Trp Thr Thr Lys Met Asp Trp Ile Phe
65                  70                  75                  80

His Thr Ile Lys Gln His Ala Leu Asn
                85


<210> SEQ ID NO 82
<211> LENGTH: 89
<212> TYPE: PRT
<213> ORGANISM: Homo sapiens

<400> SEQUENCE: 82

Phe Gln Glu Met Cys Tyr Lys Ala Tyr Leu Ala Ile Arg Gln His Ala
1               5                   10                  15

Asn Leu Phe Ile Asn Leu Phe Ser Met Met Leu Gly Ser Gly Met Pro
            20                  25                  30

Glu Leu Gln Ser Phe Asp Asp Ile Ala Tyr Ile Arg Lys Thr Leu Ala
        35                  40                  45

Leu Asp Lys Thr Glu Gln Glu Ala Leu Glu Tyr Phe Met Lys Gln Met
    50                  55                  60

Asn Asp Ala Leu His Gly Gly Trp Thr Thr Lys Met Asp Trp Ile Phe
65                  70                  75                  80

His Thr Ile Lys Gln His Ala Leu Asn
                85
```